(12) United States Patent
Dineen et al.

(10) Patent No.: US 9,346,827 B2
(45) Date of Patent: May 24, 2016

(54) 5-AMINO-OXAZEPINE AND 5-AMINO-THIAZEPANE COMPOUNDS AS BETA SECRETASE ANTAGONISTS AND METHODS OF USE

(75) Inventors: Thomas Dineen, Somerville, MA (US); Matthew Weiss, Boston, MA (US); Vinod F. Patel, Acton, MA (US); Xiao Mei Zheng, Natick, MA (US); Ryan White, Somerville, MA (US)

(73) Assignee: Amgen Inc., Thousand Oaks, CA (US)

( * ) Notice: Subject to any disclaimer, the term of this patent is extended or adjusted under 35 U.S.C. 154(b) by 86 days.

(21) Appl. No.: 13/982,222

(22) PCT Filed: Feb. 6, 2012

(86) PCT No.: PCT/US2012/024029
§ 371 (c)(1),
(2), (4) Date: Oct. 18, 2013

(87) PCT Pub. No.: WO2012/109165
PCT Pub. Date: Aug. 16, 2012

(65) Prior Publication Data
US 2014/0031340 A1   Jan. 30, 2014

Related U.S. Application Data

(60) Provisional application No. 61/440,270, filed on Feb. 7, 2011.

(51) Int. Cl.
| | |
|---|---|
| *A61K 31/553* | (2006.01) |
| *A61K 31/554* | (2006.01) |
| *C07D 498/10* | (2006.01) |
| *C07D 498/20* | (2006.01) |
| *C07D 513/10* | (2006.01) |
| *C07D 513/20* | (2006.01) |

(52) U.S. Cl.
CPC ............ *C07D 498/20* (2013.01); *C07D 498/10* (2013.01); *C07D 513/10* (2013.01)

(58) Field of Classification Search
CPC . A61K 31/553; A61K 31/554; C07D 498/10; C07D 498/20; C07D 513/10; C07D 513/20
USPC .................... 514/211.01, 211.15; 540/543
See application file for complete search history.

(56) References Cited

U.S. PATENT DOCUMENTS

| | | | |
|---|---|---|---|
| 2,683,718 | A | 7/1954 | Clinton et al. |
| 3,185,696 | A | 5/1965 | Tien et al. |
| 5,441,870 | A | 8/1995 | Seubert et al. |
| 5,712,130 | A | 1/1998 | Hajko et al. |
| 5,942,400 | A | 8/1999 | Anderson |
| 6,835,565 | B1 | 12/2004 | Gurney et al. |
| 6,864,290 | B2 | 3/2005 | Schostarez et al. |
| 6,962,934 | B2 | 11/2005 | Warpehoski et al. |
| 6,982,264 | B2 | 1/2006 | John et al. |
| 6,992,103 | B2 | 1/2006 | Faller et al. |
| 7,034,182 | B2 | 4/2006 | Fang et al. |
| 7,067,542 | B2 | 6/2006 | Schostarez et al. |
| 7,074,799 | B2 | 7/2006 | Bakthavatchalam et al. |
| 7,109,217 | B2 | 9/2006 | Coburn et al. |
| 7,115,652 | B2 | 10/2006 | Yang et al. |

(Continued)

FOREIGN PATENT DOCUMENTS

| | | |
|---|---|---|
| EP | 01942105 A1 | 7/2008 |
| EP | 2305672 A1 | 4/2011 |

(Continued)

OTHER PUBLICATIONS

Joachim et al., *Alz. Dis. Assoc. Dis.*, 6:7-34 (1992).
Selkoe, *Neuron*, 6:487 (1991).
Seubert et al., *Nature*, 359:325-327 (1992).
Citron, *Trends in Pharmacological Sciences*, 25(2):92-97 (2004).
Shankar, G.M., *Nature Medicine* (Jun. 22, 2008) online doi 10:1038 nm 1782.
Sinha et al., *Nature*, 402: (1999) (p. 510), 537-540.
Sabbagh, M. et al., *Alz. Dis. Rev.* 3:1-19 (1997).

(Continued)

*Primary Examiner* — Brenda Coleman
(74) *Attorney, Agent, or Firm* — G. Prabhakar Reddy; Bernard P. Friedrichsen; Markus Bergauer

(57) ABSTRACT

The present invention provides a new class of compounds useful for the modulation of beta-secretase enzyme (BACE) activity. The compounds have a general Formula (I); wherein variables $A^1, A^3, A^4, A^5, A^6, A^8, R^2, R^7$, X and Y of Formula (I) are defined herein. The invention also provides pharmaceutical compositions comprising the compounds, and corresponding uses of the compounds and compositions for treatment of disorders and/or conditions related to A-beta plaque formation and deposition, resulting from the biological activity of BACE. Such BACE mediated disorders include, for example, Alzheimer's Disease, cognitive deficits, cognitive impairments, schizophrenia and other central nervous system conditions. The invention further provides compounds of Formulas (II) and sub-formula embodiments of Formula (I) and (II), intermediates and processes and methods useful for the preparation of compounds of Formulas (I)-(II).

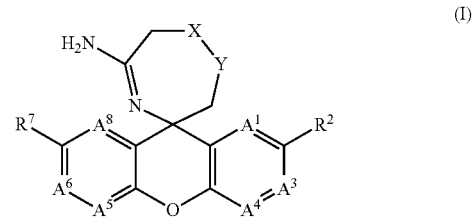

14 Claims, No Drawings

(56) References Cited

U.S. PATENT DOCUMENTS

| | | |
|---|---|---|
| 7,132,568 B2 | 11/2006 | Yang et al. |
| 7,176,242 B2 | 2/2007 | John et al. |
| 7,223,774 B2 | 5/2007 | Aquino et al. |
| 7,244,725 B2 | 7/2007 | John et al. |
| 7,244,755 B2 | 7/2007 | Fisher et al. |
| 7,253,198 B2 | 8/2007 | Demont et al. |
| 7,291,620 B2 | 11/2007 | Coburn et al. |
| 7,312,360 B2 | 12/2007 | TenBrink et al. |
| 7,348,448 B2 | 3/2008 | Nantermet et al. |
| 7,371,853 B2 | 5/2008 | Coburn et al. |
| 7,582,650 B2 | 9/2009 | DeCorte et al. |
| 7,592,348 B2 | 9/2009 | Zhu et al. |
| 8,426,447 B2 | 4/2013 | White et al. |
| 8,497,264 B2 | 7/2013 | Chen et al. |
| 8,883,782 B2 | 11/2014 | Cheng et al. |
| 8,921,363 B2 | 12/2014 | Minatti et al. |
| 8,957,083 B2 | 2/2015 | Minatti et al. |
| 8,962,859 B2 | 2/2015 | Epstein et al. |
| 9,012,446 B2 | 4/2015 | Chen et al. |
| 2003/0109559 A1 | 6/2003 | Gailunas et al. |
| 2005/0038019 A1 | 2/2005 | Beck |
| 2005/0054690 A1 | 3/2005 | Aquino et al. |
| 2005/0282825 A1 | 12/2005 | Malamas et al. |
| 2006/0111370 A1 | 5/2006 | Zhu et al. |
| 2006/0211740 A1 | 9/2006 | Demont et al. |
| 2006/0241133 A1 | 10/2006 | Shearman et al. |
| 2006/0287297 A1 | 12/2006 | DeCorte et al. |
| 2007/0004786 A1 | 1/2007 | Malamas et al. |
| 2007/0027199 A1 | 2/2007 | Malamas et al. |
| 2007/0072925 A1 | 3/2007 | Malamas et al. |
| 2007/0203116 A1 | 8/2007 | Quagliato et al. |
| 2007/0287692 A1 | 12/2007 | Wu et al. |
| 2008/0200445 A1 | 8/2008 | Zhu et al. |
| 2009/0082560 A1 | 3/2009 | Kobayashi et al. |
| 2009/0209529 A1 | 8/2009 | Andreini et al. |
| 2009/0209755 A1 | 8/2009 | Suzuki et al. |
| 2009/0306047 A1 | 12/2009 | Zhu et al. |
| 2010/0075957 A1 | 3/2010 | Tamura et al. |
| 2010/0087429 A1 | 4/2010 | White et al. |
| 2010/0160290 A1 | 6/2010 | Kobayashi et al. |
| 2014/0296226 A1 | 10/2014 | White et al. |
| 2015/0307521 A1 | 10/2015 | White et al. |

FOREIGN PATENT DOCUMENTS

| | | |
|---|---|---|
| WO | 96/14844 A1 | 5/1996 |
| WO | 00/17369 A2 | 3/2000 |
| WO | 01/70671 A2 | 9/2001 |
| WO | 03/002518 A1 | 1/2003 |
| WO | 03/030886 A2 | 4/2003 |
| WO | 2004/000821 A1 | 12/2003 |
| WO | 2004/099376 A2 | 11/2004 |
| WO | 2005/058311 A1 | 6/2005 |
| WO | 2005/097767 A1 | 10/2005 |
| WO | 2006/041404 A1 | 4/2006 |
| WO | 2006/076284 A2 | 7/2006 |
| WO | 2006/083760 A1 | 8/2006 |
| WO | 2006/138230 A3 | 12/2006 |
| WO | 2006/138265 A1 | 12/2006 |
| WO | 2007/005404 A1 | 1/2007 |
| WO | 2007/011810 A1 | 1/2007 |
| WO | 2007/011833 A2 | 1/2007 |
| WO | 2007/038271 A1 | 4/2007 |
| WO | 2007/049532 A1 | 5/2007 |
| WO | 2007/058602 A2 | 5/2007 |
| WO | 2007/114771 A1 | 10/2007 |
| WO | 2007/120096 A1 | 10/2007 |
| WO | 2007/145571 A1 | 12/2007 |
| WO | 2007/149033 A1 | 12/2007 |
| WO | 2008/054698 A2 | 5/2008 |
| WO | 2008/076045 A1 | 6/2008 |
| WO | 2008/076046 A1 | 6/2008 |
| WO | 2008/092785 A1 | 8/2008 |
| WO | 2008/103351 A3 | 8/2008 |
| WO | 2008/108378 A2 | 9/2008 |
| WO | 2008/118379 A2 | 10/2008 |
| WO | 2008/133273 A1 | 11/2008 |
| WO | 2008/133274 A1 | 11/2008 |
| WO | 2008/150217 A1 | 12/2008 |
| WO | 2009/091016 A1 | 1/2009 |
| WO | 2009/134617 A1 | 4/2009 |
| WO | 2009/131974 A1 | 10/2009 |
| WO | 2009/131975 A1 | 10/2009 |
| WO | 2010/010014 A1 | 1/2010 |
| WO | 2010/013794 A1 | 2/2010 |
| WO | 2010/021680 A2 | 2/2010 |
| WO | 2010/030954 A1 | 3/2010 |
| WO | 2010/105179 A2 | 9/2010 |
| WO | 2010/128058 A1 | 11/2010 |
| WO | 2011/020806 A1 | 2/2011 |
| WO | 2011/115928 A1 | 9/2011 |
| WO | 2011/115938 A1 | 9/2011 |
| WO | 2011/123674 A1 | 10/2011 |
| WO | 2011/130741 A1 | 10/2011 |
| WO | 2012/019056 A1 | 2/2012 |
| WO | 2012/040641 A2 | 3/2012 |
| WO | 2012/071279 A1 | 5/2012 |
| WO | 2012/112462 A1 | 8/2012 |
| WO | 2013/044092 A1 | 3/2013 |
| WO | 2014/078314 A1 | 5/2014 |

OTHER PUBLICATIONS

Cole, S.L., Vasser, R., *Molecular Degeneration* 2:22, 2007.
Luo et al., *Nature Neuroscience*, 4:231-232 (2001).
*Clin. Neuropharmacol.* 2007; 30 (pp. 317-325).
*Neurology*, 2006, 66 (pp. 602-604).
Berge et al., J. Pharm. Sci., 66:1 (1977).
Henley, D. B. et al, "Development of Semagacestat (LY450139), a Functional γ-Secretase Inhibitor. For the Treatment of Alzheimer's Disease", *Expert Opin. Pharmacother.* (2009) vol. 10(10) pp. 1657-1664.
Aisen, P .S. "Alzheimer's Disease Therapeutic Research: The Path Forward," Alzheimer's Research & Therapy 1(1):1-6 (2009).
Barrow, J. C. et al., "Discover and X-ray Crystallographic Analysis of a Spiropiperidine Iminohydantoin Inhibitor of #-Secretase," J. Med. Chem. 51(20):6259-6262 (2008).
Hamada, Y. et al., "Recent progress in the drug discovery of non-peptidic BACE1 inhibitors," Expert Opin. Drug Discov. 4(4):391-416 (2009).
Harris, J. A. et al., "Transsynaptic Progression of Amyloid-β-Induced Neuronal Dysfunction within the Entorhinal-Hippocampal Network," Neuron 68:428-441 (2010).
International Preliminary Report on Patentability and Written Opinion for International Patent Application No. PCT/US2013/069697, issued May 19, 2015, pp. 1-7.
International Preliminary Report on Patentability and Written Opinion for International Patent Application No. PCT/US2011/028401, issued Sep. 18, 2012, pp. 1-6.
International Preliminary Report on Patentability and Written Opinion for International Patent Application No. PCT/US2011/061473, issued May 28, 2013, pp. 1-5.
International Preliminary Report on Patentability and Written Opinion for International Patent Application No. PCT/US2012/024029, issued Aug. 13, 2013, pp. 1-7.
International Preliminary Report on Patentability and Written Opinion for International Patent Application No. PCT/US2011/028417, issued Sep. 18, 2012, pp. 1-5.
International Preliminary Report on Patentability and Written Opinion for International Patent Application No. PCT/US2009/056748, issued Mar. 15, 2011, pp. 1-7.
International Preliminary Report on Patentability and Written Opinion for parent PCT Application No. PCT/US2012/056658, issued on Mar. 25, 2014, pp. 1-5.
International Search Report for International Patent Application No. PCT/US2013/069697, mailed Dec. 20, 2013, pp. 1-4.
International Search Report for International Patent Application No. PCT/US2011/028401, mailed Jun. 15, 2011, pp. 1-4.
International Search Report for International Patent Application No. PCT/US2011/061473, mailed Mar. 27, 2012, pp. 1-4.

(56) References Cited

OTHER PUBLICATIONS

International Search Report for International Patent Application No. PCT/US2012/024029, mailed May 4, 2012, pp. 1-3.
International Search Report for International Patent Application No. PCT/US2011/028417, mailed Oct. 5, 2011, pp. 1-4.
International Search Report for International Patent Application No. PCT/US2009/056748, mailed Nov. 11, 2009, pp. 1-3.
International Search Report for parent PCT Application No. PCT/US2012/056658, mailed on Oct. 12, 2012, pp. 1-4.
Lukiw, W. J. "Emerging Amyloid Beta (Aβ) Peptide Modulators for the Treatment of Alzheimer's Disease (AD)," Expert Opin. Emerging Drugs 13(2):255-271 (2008).
Malamas, M. J. et al., "Aminoimidazoles as Potent and Selective Human β-Secretase(BACE1) Inhibitors," J. Med. Chem. 2009 (Page Numbers not Present in Attached Article).
Malamas, M. J. et al., "Novel Pyrrolyl 2-Aminopyridines as Potent and Selective Human β-Secretase (BACE1) Inhibitors," Bioorganic & Medicinal Chemistry Letters 20:2068-2073 (2010).
Malamas, M. S. et al., "Design and Synthesis of 5,5'-Disubstituted Aminohydantoins as Potent and Selective Human β-Secretase (BACE1) Inhibitors," J. Med. Chem.2009 (Page Numbers not Present in Attached Article).
Malamas, M. S. et al., "Di-substituted Pyridinyl Aminohydantoins as Potent and Highly Selective Human β-Secretase (BACE1) Inhibitors," Bioorganic Medicinal Chemistry Letters Accepted Manuscript (2009).
May, P. C. et al., "Robust Central Reduction of Amyloid-β in Humans with an Orally Available, Non-Peptidic β-Secretase Inhibitor," J. Neurosci. 31(46):16507-16516 (2011).
Notice of Allowance mailed Nov. 11, 2015 for U.S. Appl. No. 14/346,252, filed Mar. 20, 2014, pp. 1-5.
Nowak, P. et al., "Discovery and Initial Optimization of 5,5'-Disubstituted Aminohydantoins as Potent β-Secretase (BACE1) Inhibitors," Bioorganic Medicinal Chemistry Letters Accepted Manuscript (2009).
Office Action mailed Apr. 20, 2015 for U.S. Appl. No. 14/346,252, filed Mar. 20, 2014, pp. 1-8.
Office Action mailed Dec. 27, 2013 for U.S. Appl. No. 13/047,734, filed Mar. 14, 2011, pp. 1-14.
Office Action mailed Dec. 30, 2013 for U.S. Appl. No. 13/929,483, filed Jun. 27, 2013, pp. 1-6.
Office Action mailed Jun. 8, 2011 for U.S. Appl. No. 12/558,426, filed Sep. 11, 2009, pp. 1-11.
Office Action mailed May 28, 2014 for U.S. Appl. No. 13/988,745, filed Sep. 5, 2013, pp. 1-5.
Office Action mailed Nov. 28, 2012 for U.S. Appl. No. 13/047,693, filed Mar. 14, 2011, pp. 1-5.
Office Action mailed Sep. 6, 2012 for U.S. Appl. No. 12/558,426, filed Sep. 11, 2009, pp. 1-8.
Patani, G. A. and Lavoie, E. J. "Bioisosterism: A Rational Approach in Drug Design," Chem. Rev. 96:3147-3176 (1996).
Rauk, A, "The Chemistry of Alzheimer's Disease," Chem. Soc. Rev. 38:2698-2715 (2009).
Sabbagh, M. N. "Drug Development for Alzheimer's Disease: Where Are We Now and Where Are We Headed?" Am. J. Geriatr. Pharmacother. 7(3):167-185 (2009).
Saxena, U. "Alzheimer's Disease Amyloid Hypothesis at Crossroads: Where Do We Go from Here?" Expert Opin. Ther. Targets 14(12):1273-1277 (2010).
Town, T. et al., "Blocking TGF-β-Smad2/3 Innate Immune Signaling Mitigates Alzheimer-Like Pathology," Nature Medicine 14(6):681-687 (2008).
Vassar, R. et al., "The β-Secretase Enzyme BACE in Health and Alzheimer's Disease: Regulation, Cell Biology, Function, and Therapeutic Potential," J. Neurosci. 29(41):12787-12794 (2009).
West, A. R. Solid State Chemistry and Its Applications, Wiley, New York, 1988, pp. 358, 365.
Zhou, P. et al. "An Efficient Synthesis of 2-Amino-4-(4-fluoro-3-(2-fluoropyridine-3-yl)phenyl)-4-(4-methoxy-3-methylphenyl)-1-methyl-1H-imidazol-5(4H)-one, a Potent BACE1 Inhibitor," ARKIVOC vi 84-88 (2010).
Zhou, P. et al., "Pyridinyl Aminohydantoins as Small Molecule BACE1 Inhibitors," Bioorganic Medicinal Chemistry Letters 20:2326-2329 (2010).

5-AMINO-OXAZEPINE AND 5-AMINO-THIAZEPANE COMPOUNDS AS BETA SECRETASE ANTAGONISTS AND METHODS OF USE

RELATED APPLICATIONS

This application is a US national stage application under 35 U.S.C. §371 of International Application No. PCT/US2012/024029, having an international filing date of Feb. 6, 2012, which claims the benefit of, and priority to, U. S. Provisional Application No. 61/440,270, filed on Feb. 7, 2011, each specification of which is hereby incorporated herein by reference in its entirety.

FIELD OF THE INVENTION

The invention relates generally to pharmaceutically active compounds, pharmaceutical compositions and methods of use thereof, to treat beta-secretase mediated diseases and conditions, including, without limitation, Alzheimer's disease, plaque formation and related central nervous system (CNS) disorders.

BACKGROUND OF THE INVENTION

Alzheimer's disease (AD) affects greater than 12 million aging people worldwide, and importantly, the number affected continues to grow. AD accounts for the majority of dementia clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to effectively treat AD upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.*, 6:7-34 (1992).

Several lines of evidence indicate that progressive cerebral deposition of A-beta plays a seminal role in the pathogenisis of AD and can precede cognitive symptoms by years or even decades. Selkoe, *Neuron*, 6:487 (1991). Release of A-beta from neuronal cells grown in culture and the presence of A-beta in cerebrospinal fluid (CSF) of both normal individuals and AD patients has been demonstrated. Seubert et al., *Nature*, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide ranging in about 39-42 amino acid residues. A-beta 42 (42 amino acids long) is thought to be the major component of these plaque deposits in the brains of Alzheimer's Disease patients. Citron, *Trends in Pharmacological Sciences*, 25(2):92-97 (2004).

Similar plaques appear in some variants of Lewy body dementia and in inclusion body myositis, a muscle disease. $A\beta$ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the two-molecule, soluble form of the peptide is a causative agent in the development of Alzheimer's and that the two-molecule form is the smallest synaptotoxic species of soluble amyloid beta oligomer. Shankar, G. M., *Nature Medicine* (Jun. 22, 2008) online doi 10:1038 nm 1782.

Several aspartyl proteases, including beta-secretase and gamma-secretase, are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature*, 402:537-554 (1999) (p510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., *Molecular Degeneration* 2:22, 2007. When crossed with transgenic mice that over express APP, the progeny of BACE deficient mice show reduced amounts of A-beta in brain extracts as compares with control animals (Luo et al., *Nature Neuroscience,* 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities. To this end, inhibition of beta secretase activity and a corresponding reduction of A-beta in the brain should provide a therapeutic method for treating AD and other beta amyloid or plaque related disorders.

Consequently, the approach of regulating or reducing the formation of A-beta peptide formation and deposition as a potential treatment for AD has received tremendous attention and belief from both researchers and investors alike. A small molecule gamma-secretase inhibitor, LY450139 ("Semagacestat"), an A-beta lowering agent, is in phase II and Phase III clinical trials for the treatment of Alzheimer's Disease. The pharmacokinetics of semagacestat in plasma, as well as the plasma and cerebral spinal fluid (CSF) A-Beta peptide levels as pharmacodynamic responses to semagacestat administration were evaluated in healthy human subjects in single and multiple doses, and pharmacokinetic and pharmacodynamic changes were also assessed in mild to moderate AD patients in two (2) clinical trials (*Expert Opin. Pharmacother.* (2009), 10 (10); *Clin. Neuropharmacol.* 2007; 30 (pgs 317-325); and *Neurology,* 2006, 66 (pgs 602-624)).

Additional approaches have been taken in attempts to treat AD and plaque-related disorders. One such approach to reduce the formation of plaque on the brain involves the inhibition of and, therefore, the reduction of BACE activity. For example, each of the following PCT publications: WO 07/058602, WO 10/021680, WO 10/105179, WO 06/041404, WO 07/114771, WO 08/076045, WO 08/076046, WO 08/150217, WO 07/038271, WO 09/091016, WO 08/108378, WO 09/134617, WO 05/097767, WO 08/092785, WO 06/138265, WO 08/103351, WO 06/138230, WO 08/200445, WO 06/111370, WO 07/287692, WO 05/058311, EP 01942105, WO 08/133273, WO 08/133274, WO 07/049532, US20070027199, WO 07/038271, US20070072925, US20070203116, US20050282826, WO 08/118379, WO 06/076284, US20070004786, WO 06/083760, WO 07/011810, WO 07/011833, WO 08/054698 and WO10/128058, describe inhibitors of BACE, useful for treating AD and other beta-secretase mediated disorders.

Despite the many efforts and resources directed to researching A-beta lowering agents, there remains a need to identify safe and efficacious treatment agents for AD.

BRIEF DESCRIPTION OF THE INVENTION

The present invention provides a new class of compounds useful for the modulation of beta secretase activity, and as treatment of AD. Particularly, the compounds of the invention are useful for the regulation or reduction of the formation of A-beta peptide and, consequently, the regulation and/or reduction of formation of beta amyloid plaque both on the brain, as well as in the CNS. To this end, the compounds are useful for the treatment of AD and other beta secretase and/or plaque-related and/or mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, hydrates, solvates and pharmaceutically acceptable salts thereof, are generally defined by Formula I

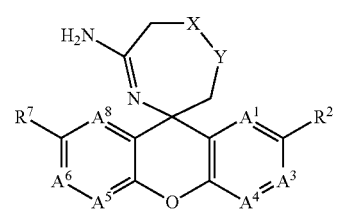

wherein each of $A^1$, $A^3$, $A^4$, $A^5$, $A^6$, $R^2$, $R^7$, X and Y of Formula I are defined below. The invention also provides procedures for making compounds of Formula, and sub-Formulas thereof, as well as intermediates useful in such procedures.

The invention further provides pharmaceutical compositions comprising compounds of the invention, methods for the treatment of beta secretase mediated diseases using both the compounds and compositions of the invention. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, there are provided compounds, including stereoisomers, tautomers, hydrates, solvates and pharmaceutically acceptable salts thereof, which are generally defined by Formula I:

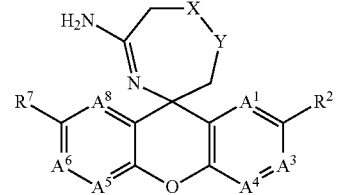

wherein
$A^1$ is $CR^1$ or N;
$A^3$ is $CR^3$ or N;
$A^4$ is $CR^4$ or N;
$A^5$ is $CR^5$ or N;
$A^6$ is $CR^6$ or N;
$A^8$ is $CR^8$ or N, provided that no more than one of $A^1$, $A^3$, $A^4$, $A^5$, $A^6$ and $A^8$ is N;
each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$S(O)_o$$C_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH;

R$^2$ is Cl, Br, C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of R$^9$;

each of R$^3$ and R$^6$, independently, is H, halo, haloalkyl, haloalkoxyl, C$_{1-6}$-alkyl, CN, OH, OC$_{1-6}$-alkyl, S(O)$_o$C$_{1-6}$-alkyl, NHC$_{1-6}$-alkyl or C(O)C$_{1-6}$-alkyl;

R$^7$ is C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NHC(=O)R$^9$, —C(=O)NHR$^9$, —NHS(O)$_2$R$^9$, —S(O)$_2$NHR$^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of R$^9$;

each R$^9$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino, C$_{1-3}$thioalkoxyl, or oxetanyl; and —X—Y— taken together is —CR$^{10}$R$^{10}$—O—, —O—CR$^{10}$R$^{10}$—, —CR$^{10}$R$^{10}$—S— or —S—CR$^{10}$R$^{10}$, wherein each R$^{10}$, independently, is H or F.

In another embodiment of the present invention, the compounds, and solvates, tautomers, hydrates, stereoisomers and pharmaceutically acceptable salts thereof, are defined by Formula I, wherein A$^1$ is CH or CF;
A$^3$ is CH, CF or N;
A$^4$ is CH, CF or N;
A$^5$ is CH;
A$^6$ is CH;
A$^8$ is CH;

R$^2$ is C$_{3-6}$-alkyl, C$_{2-4}$alkynyl, —OC$_{1-6}$alkyl, —SC$_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the C$_{3-6}$-alkyl, C$_{2-4}$alkynyl, —OC$_{1-6}$alkyl, —SC$_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-5 substituents of R$^9$;

R$^7$ is C$_{2-4}$alkynyl, —OC$_{1-6}$alkyl, phenyl, pyridyl, pyrimidyl, pyrazinyl or pyridazinyl, wherein the C$_{2-4}$alkynyl, —OC$_{1-6}$alkyl, pyridyl, pyrimidyl, pyrazinyl and pyridazinyl are optionally substituted, independently, with 1-3 substituents of R$^9$;

each R$^9$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino, C$_{1-3}$thioalkoxyl, or oxetanyl; and —X—Y— taken together is —CR$^{10}$R$^{10}$—O—, —O—CR$^{10}$R$^{10}$—, —CR$^{10}$R$^{10}$—S— or —S—CR$^{10}$R$^{10}$, wherein each R$^{10}$, independently, is H or F.

In another embodiment of the present invention, the compounds, and hydrates, solvates, tautomers, stereoisomers and pharmaceutically acceptable salts thereof, are defined by Formula II

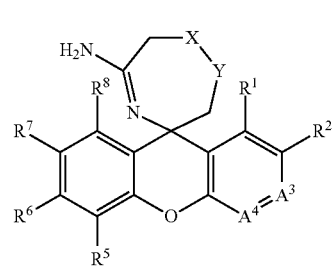

II wherein
$A^3$ is $CR^3$ or N;
$A^4$ is $CR^4$ or N, provided that no more than one of $A^3$ and $A^4$ is N;

each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$S(O)_o$ $C_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH;

$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;

each of $R^3$ and $R^6$, independently, is H, halo, haloalkyl, haloalkoxy, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl)$_2$, —NHC(=O)R$^9$, —C(=O)NHR$^9$, —NHS(O)$_2$R$^9$, —S(O)$_2$NHR$^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl; and —X—Y— taken together is —$CR^{10}R^{10}$—O—, —O—$CR^{10}R^{10}$—, —$CR^{10}R^{10}$—S— or —S—$CR^{10}R^{10}$, wherein each $R^{10}$, independently, is H or F.

In another embodiment of the present invention, the compounds, and solvates, tautomers, stereoisomers and pharmaceutically acceptable salts thereof, are defined by Formula II-A

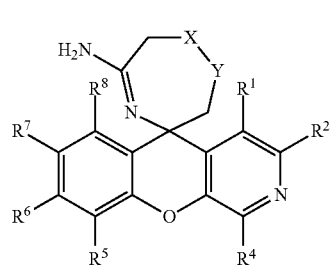

II-A wherein each of $R^2$, $R^4$, $R^5$, $R^6$, $R^7$, $R^8$ and $R^9$ is as defined above with respect to Formula I or Formula II.

In another embodiment of the present invention, the compounds, and hydrates, solvates, tautomers, stereoisomers and pharmaceutically acceptable salts thereof, are defined by Formula III

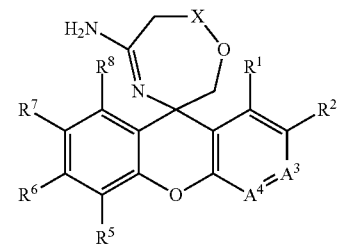

III wherein
$A^3$ is $CR^3$ or N;
$A^4$ is $CR^4$ or N, provided that no more than one of $A^3$ and $A^4$ is N;

each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$S(O)_o$ $C_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH;

$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the $C_{1-6}$-alkyl, $C_{2-4}$alkenyl, $C_{2-4}$alkynyl, —$OC_{1-6}$alkyl, —$SC_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of R$^9$;

each of R$^3$ and R$^6$, independently, is H, halo, haloalkyl, haloalkoxy, C$_{1-6}$-alkyl, CN, OH, OC$_{1-6}$-alkyl, S(O)$_o$C$_{1-6}$-alkyl, NHC$_{1-6}$-alkyl or C(O)C$_{1-6}$-alkyl;

R$^7$ is C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of R$^9$;

each R$^9$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino, C$_{1-3}$thioalkoxyl, or oxetanyl; and —X— is —CR$^{10}$R$^{10}$, wherein each R$^{10}$, independently, is H or F.

In another embodiment of the present invention, the compounds, and hydrates, solvates, tautomers, stereoisomers and pharmaceutically acceptable salts thereof, are defined by Formula IV

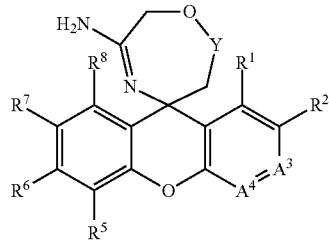

IV wherein

A$^3$ is CR$^3$ or N;

A$^4$ is CR$^4$ or N, provided that no more than one of A$^3$ and A$^4$ is N;

each of R$^1$, R$^4$, R$^5$ and R$^8$, independently, is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH;

R$^2$ is Cl, Br, C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of R$^9$;

each of R$^3$ and R$^6$, independently, is H, halo, haloalkyl, haloalkoxy, C$_{1-6}$-alkyl, CN, OH, OC$_{1-6}$-alkyl, S(O)$_o$C$_{1-6}$-alkyl, NHC$_{1-6}$-alkyl or C(O)C$_{1-6}$-alkyl;

R$^7$ is C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of R$^9$;

each R$^9$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkoxyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$alkoxyl, C$_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$thioalkoxyl, or oxetanyl; and —Y— is —$CR^{10}R^{10}$, wherein each $R^{10}$, independently, is H or F.

The present invention contemplates that the various different embodiments of Formulas I, II, III and IV, and sub-Formulas thereof, described herein, may comprise the following embodiments with respect to individual variables of $A^1$, $A^3$, $A^4$, $A^5$, $A^6$, $A^8$, $R^2$, $R^7$, X and Y where applicable, as described below. Hence, these embodiments with respect to individual variables $A^1$, $A^3$, $A^4$, $A^5$, $A^6$, $A^8$, $R^2$, $R^7$, X and Y, where applicable, may be applied "in conjunction with any of the other {above and below} embodiments" to create various embodiments of general Formulas I, II, III and IV and each sub-formula thereof, which are not literally described herein.

In another embodiment, the invention includes compounds wherein $A^1$ is CH, CF or N, in conjunction with any of the above or below embodiments.

In another embodiment, the invention includes compounds wherein $A^1$ is CH or CF, in conjunction with any of the above or below embodiments.

In another embodiment, the invention includes compounds wherein $A^1$ is CF, in conjunction with any of the above or below embodiments.

In another embodiment, the invention includes compounds wherein $A^1$ is N, in conjunction with any of the above or below embodiments.

In another embodiment, the invention includes compounds wherein $A^3$ is CH, CF or N, in conjunction with any of the above or below embodiments.

In another embodiment, the invention includes compounds wherein $A^3$ is CH or N, in conjunction with any of the above or below embodiments.

In another embodiment, the invention includes compounds wherein $A^3$ is CH or CF, in conjunction with any of the above or below embodiments.

In another embodiment, the invention includes compounds wherein $A^3$ is CF, in conjunction with any of the above or below embodiments.

In another embodiment, the invention includes compounds wherein $A^3$ is N, in conjunction with any of the above or below embodiments.

In another embodiment, the invention includes compounds wherein $A^4$ is CH, CF or N, in conjunction with any of the above or below embodiments.

In another embodiment, the invention includes compounds wherein $A^4$ is CH or CF, in conjunction with any of the above or below embodiments.

In another embodiment, the invention includes compounds wherein $A^4$ is CF or N, in conjunction with any of the above or below embodiments.

In another embodiment, the invention includes compounds wherein $A^4$ is CH or N, in conjunction with any of the above or below embodiments.

In another embodiment, the invention includes compounds wherein $A^4$ is CF, in conjunction with any of the above or below embodiments.

In another embodiment, the invention includes compounds wherein $A^4$ is N, in conjunction with any of the above or below embodiments.

In another embodiment, the invention includes compounds wherein $A^5$ is CH, CF or N, in conjunction with any of the above or below embodiments.

In another embodiment, the invention includes compounds wherein $A^5$ is CH or CF, in conjunction with any of the above or below embodiments.

In another embodiment, the invention includes compounds wherein $A^5$ is N, in conjunction with any of the above or below embodiments.

In another embodiment, the invention includes compounds wherein $A^6$ is $CR^6$ wherein $R^6$ is H, F, Br or

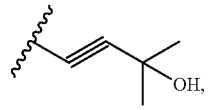 [SMILES: *C#CC(C)(C)O]

or $A^6$ is N, in conjunction with any of the above or below embodiments.

In another embodiment, the invention includes compounds wherein $A^6$ is CH, in conjunction with any of the above or below embodiments.

In another embodiment, the invention includes compounds wherein $A^6$ is N, in conjunction with any of the above or below embodiments.

In another embodiment, the invention includes compounds wherein $A^8$ is $CR^8$ wherein $R^8$ is F, Br or

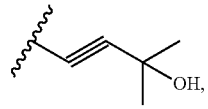 [SMILES: *C#CC(C)(C)O]

in conjunction with any of the above or below embodiments.

In another embodiment, the invention includes compounds wherein $A^8$ is CH, CF or N, in conjunction with any of the above or below embodiments.

In another embodiment, the invention includes compounds wherein $A^8$ is CH or CF, in conjunction with any of the above or below embodiments.

In another embodiment, the invention includes compounds wherein $A^8$ is N, in conjunction with any of the above or below embodiments.

In another embodiment, the invention includes compounds wherein $A^1$ is $CR^1$ or N, $A^3$ is $CR^3$ or N, $A^4$ is $CR^4$ or N, $A^5$ is $CR^5$ or N, $A^6$ is $CR^6$ or N and $A^8$ is $CR^8$ or N, provided that no more than one of $A^1$, $A^3$, $A^4$, $A^5$, $A^6$ and $A^8$ is N, in conjunction with any of the above or below embodiments.

In another embodiment, the invention includes compounds wherein $A^1$ is $CR^1$, $A^3$ is $CR^3$ or N, $A^4$ is $CR^4$ or N, $A^5$ is $CR^5$, $A^6$ is $CR^6$ and $A^8$ is $CR^8$, provided that no more than one of $A^3$ and $A^4$ is N, in conjunction with any of the above or below embodiments.

In another embodiment, the invention includes compounds wherein $A^1$ is $CR^1$, $A^3$ is N, $A^4$ is $CR^4$, $A^5$ is $CR^5$, $A^6$ is $CR^6$ and $A^8$ is $CR^8$, in conjunction with any of the above or below embodiments.

In another embodiment, the invention includes compounds wherein $A^1$ is $CR^1$, $A^3$ is $CR^3$, $A^4$ is N, $A^5$ is $CR^5$, $A^6$ is $CR^6$ and $A^8$ is $CR^8$, in conjunction with any of the above or below embodiments.

In another embodiment, the invention includes compounds wherein $A^1$ is $CR^1$, $A^3$ is $CR^3$, $A^4$ is $CR^4$, $A^5$ is $CR^5$, $A^6$ is $CR^6$ and $A^8$ is $CR^8$, in conjunction with any of the above or below embodiments.

In another embodiment, the invention includes compounds wherein $A^1$ is $CR^1$, $A^3$ is $CR^3$ or N, $A^4$ is $CR^4$ or N, $A^5$ is $CR^5$, $A^6$ is $CR^6$ and $A^8$ is $CR^8$, wherein each of $R^1$, $R^4$, $R^5$ and $R^8$, independently, is H, F, Cl, Br, $CF_3$, $OCF_3$, $C_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH and each of R$^3$ and R$^6$, independently, is H, halo, haloalkyl, haloalkoxyl, C$_{1-6}$-alkyl, CN, OH, OC$_{1-6}$-alkyl, S(O)$_o$C$_{1-6}$-alkyl, NHC$_{1-6}$-alkyl or C(O)C$_{1-6}$-alkyl, provided that no more than one of A$^3$ and A$^4$ is N, in conjunction with any of the above or below embodiments.

In another embodiment, the invention includes compounds wherein A$^1$ is CH or CF, A$^3$ is CH, CF or N, A$^4$ is CH, CF or N, A$^5$ is CH, CF or N, A$^6$ is CH, CF or N, A$^8$ is CH or CF, and R$^9$ is H, CH$_3$, C$_2$H$_5$, propyl, butyl, acetyl or benzyl, in conjunction with any of the above or below embodiments.

In another embodiment, the invention includes compounds wherein R$^1$ is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH, in conjunction with any of the above or below embodiments.

In another embodiment, the invention includes compounds wherein R$^1$ is H, F, Cl, CF$_3$, OCF$_3$, methyl, ethyl, CN, OH, OCH$_3$, SCH$_3$, NHCH$_3$ or C(O)CH$_3$, in conjunction with any of the above or below embodiments.

In another embodiment, the invention includes compounds wherein R$^1$ is H, F, methyl, CN or OH, in conjunction with any of the above or below embodiments.

In another embodiment, the invention includes compounds wherein R$^1$ is H or F, in conjunction with any of the above or below embodiments.

In another embodiment, the invention includes compounds wherein R$^1$ is H, in conjunction with any of the above or below embodiments.

In another embodiment, the invention includes compounds wherein R$^2$ is Cl, Br, C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the C$_{1-6}$-alkyl, C$_{2-4}$alkenyl, C$_{2-4}$alkynyl, —OC$_{1-6}$alkyl, —SC$_{1-6}$alkyl, —NHC$_{1-6}$alkyl, —N(C$_{1-3}$alkyl)$_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of R$^9$, in conjunction with any of the above or below embodiments.

In another embodiment, the invention includes compounds wherein R$^2$ is C$_{1-6}$-alkyl, C$_{2-4}$alkenyl, C$_{2-4}$alkynyl, —OC$_{1-6}$alkyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of R$^9$, in conjunction with any of the above or below embodiments.

In another embodiment, the invention includes compounds wherein R$^2$ is C$_{3-6}$-alkyl, C$_{3-8}$-cycloalkyl, C$_{2-4}$alkynyl, —OC$_{1-6}$alkyl, —SC$_{1-6}$alkyl, phenyl, pyridyl, pyrimidyl, pyrazinyl, pyridazinyl, dihydropyranyl, tetrahydropyranyl, pyrrolidinyl, tetrahydropyrrolyl, piperidinyl, morpholinyl or 8-oxo-3-aza-bicyclo[3.2.1]oct-3-yl, wherein the C$_{3-6}$-alkyl, C$_{3-8}$-cycloalkyl, C$_{2-4}$alkynyl, —OC$_{1-6}$alkyl, —SC$_{1-6}$alkyl, phenyl, pyridyl, pyrimidyl, pyrazinyl, pyridazinyl, dihydropyranyl, tetrahydropyranyl, pyrrolidinyl, tetrahydropyrrolyl, piperidinyl, morpholinyl and 8-oxo-3-aza-bicyclo[3.2.1]oct-3-yl are optionally substituted, independently, with 1-3 substituents of R$^9$, in conjunction with any of the above or below embodiments.

In another embodiment, the invention includes compounds wherein R$^2$ is C$_{2-4}$alkynyl, —OC$_{1-6}$alkyl, pyridyl, pyrimidyl, dihydropyranyl, tetrahydropyranyl, pyrrolidinyl, tetrahydropyrroly or piperidinyl, wherein the C$_{2-4}$alkynyl, —OC$_{1-6}$alkyl, pyridyl, pyrimidyl, dihydropyranyl, tetrahydropyranyl, pyrrolidinyl, tetrahydropyrroly and piperidinyl are optionally substituted, independently, with 1-3 substituents of R$^9$, in conjunction with any of the above or below embodiments.

In another embodiment, the invention includes compounds wherein R$^2$ is C$_{2-4}$alkynyl, —OC$_{1-6}$alkyl, pyridyl, dihydropyranyl, pyrrolidinyl, tetrahydropyrrolyl or piperidinyl, wherein the C$_{2-4}$alkynyl, —OC$_{1-6}$alkyl, pyridyl, dihydropyranyl, pyrrolidinyl, tetrahydropyrrolyl and piperidinyl are optionally substituted, independently, with 1-3 substituents of R$^9$, in conjunction with any of the above or below embodiments.

In another embodiment, the invention includes compounds wherein R$^2$ is C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl or —NH-benzyl, wherein the C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl and —NH-benzyl are optionally substituted, independently, with 1-3 substituents of R$^9$, in conjunction with any of the above or below embodiments.

In another embodiment, the invention includes compounds wherein R$^2$ is Cl, Br, C$_{1-6}$-alkyl, C$_{2-4}$alkenyl, C$_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclobutyl, cyclopentyl or cyclohexyl, wherein the C$_{1-6}$-alkyl, C$_{2-4}$alkenyl, C$_{2-4}$alkynyl and ring are optionally substituted, independently, with 1-3 substituents of R$^9$, in conjunction with any of the above or below embodiments.

In another embodiment, the invention includes compounds wherein R$^3$ is H, halo, haloalkyl, haloalkoxyl, C$_{1-6}$-alkyl, CN, OH, OC$_{1-6}$-alkyl, S(O)$_o$C$_{1-6}$-alkyl, NHC$_{1-6}$-alkyl or C(O)C$_{1-6}$-alkyl, in conjunction with any of the above or below embodiments.

In another embodiment, the invention includes compounds wherein $R^3$ is H, F, Cl, Br, $CF_3$, $OCF_3$, $C_{1-6}$-alkyl, CN, OH, —$OC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH, in conjunction with any of the above or below embodiments.

In another embodiment, the invention includes compounds wherein $R^3$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the invention includes compounds wherein $R^3$ is H, F, methyl, CN or OH, in conjunction with any of the above or below embodiments.

In another embodiment, the invention includes compounds wherein $R^3$ is H or F, in conjunction with any of the above or below embodiments.

In another embodiment, the invention includes compounds wherein $R^3$ is H, in conjunction with any of the above or below embodiments.

In another embodiment, the invention includes compounds wherein $R^4$ is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH, in conjunction with any of the above or below embodiments.

In another embodiment, the invention includes compounds wherein $R^4$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the invention includes compounds wherein $R^4$ is H, F, methyl, CN or OH, in conjunction with any of the above or below embodiments.

In another embodiment, the invention includes compounds wherein $R^4$ is H or F, in conjunction with any of the above or below embodiments.

In another embodiment, the invention includes compounds wherein $R^4$ is H, in conjunction with any of the above or below embodiments.

In another embodiment, the invention includes compounds wherein $R^5$ is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH, in conjunction with any of the above or below embodiments.

In another embodiment, the invention includes compounds wherein $R^5$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the invention includes compounds wherein $R^5$ is H, F, methyl, CN or OH, in conjunction with any of the above or below embodiments.

In another embodiment, the invention includes compounds wherein $R^5$ is H or F, in conjunction with any of the above or below embodiments.

In another embodiment, the invention includes compounds wherein $R^5$ is H, in conjunction with any of the above or below embodiments.

In another embodiment, the invention includes compounds wherein $R^6$ is H, halo, haloalkyl, haloalkoxyl, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl, in conjunction with any of the above or below embodiments.

In another embodiment, the invention includes compounds wherein $R^6$ is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH, in conjunction with any of the above or below embodiments.

In another embodiment, the invention includes compounds wherein $R^6$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the invention includes compounds wherein $R^6$ is H, F, methyl, CN or OH, in conjunction with any of the above or below embodiments.

In another embodiment, the invention includes compounds wherein $R^6$ is H or F, in conjunction with any of the above or below embodiments.

In another embodiment, the invention includes compounds wherein $R^6$ is H, in conjunction with any of the above or below embodiments.

In another embodiment, the invention includes compounds wherein $R^7$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —$NHC(=O)R^9$, —$C(=O)NHR^9$, —$NHS(O)_2R^9$, —$S(O)_2NHR^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$, in conjunction with any of the above or below embodiments.

In another embodiment, the invention includes compounds wherein $R^7$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$, in conjunction with any of the above or below embodiments.

In another embodiment, the invention includes compounds wherein $R^7$ is phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$, in conjunction with any of the above or below embodiments.

In another embodiment, the invention includes compounds wherein $R^7$ is $C_{2-4}$alkynyl, —OC$_{1-6}$alkyl, phenyl, pyridyl, pyrimidyl, pyrazinyl or pyridazinyl, wherein the $C_{2-4}$alkynyl, —OC$_{1-6}$alkyl, pyridyl, pyrimidyl, pyrazinyl and pyridazinyl are optionally substituted, independently, with 1-3 substituents of $R^9$, in conjunction with any of the above or below embodiments.

In another embodiment, the invention includes compounds wherein $R^7$ is $C_{2-4}$alkynyl, —OC$_{1-6}$alkyl, —NHC(=O)R$^9$, —C(=O)NHR$^9$, —NHS(O)$_2$R$^9$, —S(O)$_2$NHR$^9$, phenyl, pyridyl, pyrimidyl, pyrazinyl or pyridazinyl, wherein the $C_{2-4}$alkynyl, —OC$_{1-6}$alkyl, pyridyl, pyrimidyl, pyrazinyl and pyridazinyl are optionally substituted, independently, with 1-3 substituents of $R^9$, in conjunction with any of the above or below embodiments.

In another embodiment, the invention includes compounds wherein $R^7$ is $C_{2-4}$alkynyl, —OC$_{1-6}$alkyl, —NHC(=O)R$^9$, —NHS(O)$_2$R$^9$, phenyl, pyridyl, pyrimidyl, pyrazinyl or pyridazinyl, wherein the $C_{2-4}$alkynyl, —OC$_{1-6}$alkyl, pyridyl, pyrimidyl, pyrazinyl and pyridazinyl are optionally substituted, independently, with 1-3 substituents of $R^9$, in conjunction with any of the above or below embodiments.

In another embodiment, the invention includes compounds wherein $R^7$ is $C_{2-4}$alkynyl, —OC$_{1-6}$alkyl, phenyl, 3-pyridyl, 5-pyrimidyl, pyrazinyl or 2-pyridazinyl, wherein the $C_{2-4}$alkynyl, —OC$_{1-6}$alkyl, 3-pyridyl, 5-pyrimidyl, pyrazinyl and 2-pyridazinyl are optionally substituted, independently, with 1-3 substituents of $R^9$, in conjunction with any of the above or below embodiments.

In another embodiment, the invention includes compounds wherein $R^7$ is a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, said ring optionally substituted, independently, with 1-3 substituents of $R^9$, in conjunction with any of the above or below embodiments.

In another embodiment, the invention includes compounds wherein $R^7$ is a ring selected from phenyl, 3-pyridyl, 5-pyrimidyl or 2-pyridazinyl, said ring optionally substituted, independently, with 1-5 substituents of $R^9$, in conjunction with any of the above or below embodiments.

In another embodiment, the invention includes compounds wherein $R^7$ is phenyl, 3-pyridyl, 5-pyrimidyl or 2-pyridazinyl, each of which is optionally substituted with 1-5 substituents of F, Cl, Br, I, CN, CF$_3$, C$_2$F$_5$, haloalkoxyl, C$_{1-6}$-alkyl, CN, OH, OC$_{1-6}$-alkyl, SC$_{1-6}$-alkyl, oxetanyl or C$_{2-3}$alkynyl, in conjunction with any of the above or below embodiments.

In another embodiment, the invention includes compounds wherein $R^8$ is H, halo, haloalkyl, haloalkoxyl, C$_{1-6}$-alkyl, CN, OH, OC$_{1-6}$-alkyl, S(O)$_o$C$_{1-6}$-alkyl, NHC$_{1-6}$-alkyl or C(O)C$_{1-6}$-alkyl, in conjunction with any of the above or below embodiments.

In another embodiment, the invention includes compounds wherein $R^8$ is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NHC$_{1-6}$-alkyl or —C(O)C$_{1-6}$-alkyl, wherein the C$_{1-6}$-alkyl and C$_{1-6}$-alkyl portion of —OC$_{1-6}$-alkyl, —S(O)$_o$C$_{1-6}$-alkyl, —NHC$_{1-6}$-alkyl and —C(O)C$_{1-6}$-alkyl are optionally substituted with 1-3 substituents of F, oxo or OH, in conjunction with any of the above or below embodiments.

In another embodiment, the invention includes compounds wherein $R^8$ is H, F, Cl, CF$_3$, OCF$_3$, methyl, ethyl, CN, OH, OCH$_3$, SCH$_3$, NHCH$_3$ or C(O)CH$_3$, in conjunction with any of the above or below embodiments.

In another embodiment, the invention includes compounds wherein $R^8$ is H, F, methyl, CN or OH, in conjunction with any of the above or below embodiments.

In another embodiment, the invention includes compounds wherein $R^8$ is H or F, in conjunction with any of the above or below embodiments.

In another embodiment, the invention includes compounds wherein $R^8$ is H, in conjunction with any of the above or below embodiments.

In another embodiment, the invention includes compounds wherein each $R^1$, $R^4$, $R^5$ and $R^8$, independently, is F, Cl, CF$_3$, OCF$_3$, methyl, CN, OH, OCH$_3$, SCH$_3$, NHCH$_3$, oxetanyl or C$_{2-3}$alkynyl, in conjunction with any of the above or below embodiments.

In another embodiment, the invention includes compounds wherein each $R^9$, independently, is F, CF$_3$, CN, CH$_3$, —OCH$_3$, —SCH$_3$, —NHCH$_3$, oxetanyl or C$_{2-3}$alkynyl, in conjunction with any of the above or below embodiments.

In another embodiment, the invention includes compounds wherein each $R^9$, independently, is halo, haloalkyl, CN, OH, NO$_2$, NH$_2$, acetyl, —C(O)NHCH$_3$, oxo, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolyl, pyrrolidinyl, tetrahydropyrrolyl, piperazinyl, oxetanyl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolidinyl, oxetanyl or dioxolyl, is optionally substituted independently with 1-5 substituents of F, Cl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C$_{1-3}$alkylamino-, C$_{1-3}$dialkylamino, C$_{1-3}$thioalkoxyl, or oxetanyl, in conjunction with any of the above or below embodiments.

In another embodiment, the invention includes compounds wherein —X—Y— taken together is —CR$^{10}$R$^{10}$—O—, —O—CR$^{10}$R$^{10}$—, —CR$^{10}$R$^{10}$—S— or —S—CR$^{10}$R$^{10}$, wherein each R$^{10}$, independently, is H or F, in conjunction with any of the above or below embodiments.

In another embodiment, the invention includes compounds wherein —X—Y— is —CR$^{10}$R$^{10}$—O— or —O—CR$^{10}$R$^{10}$—, wherein each R$^{10}$, independently, is H or F, in conjunction with any of the above or below embodiments.

In another embodiment, the invention includes compounds wherein —X—Y— is —CR$^{10}$R$^{10}$—S— or —S—CR$^{10}$R$^{10}$—, wherein each R$^{10}$, independently, is H or F, in conjunction with any of the above or below embodiments.

In another embodiment, the invention includes compounds wherein —X—Y— is —CH$_2$—O— or —O—CH$_2$—, in conjunction with any of the above or below embodiments.

In another embodiment, the invention includes compounds wherein —X—Y— is —CH$_2$—S— or —S—CH$_2$—, in conjunction with any of the above or below embodiments.

In another embodiment, the invention includes compounds wherein —X—Y— is —CHF—O— or —O—CHF—, in conjunction with any of the above or below embodiments.

In another embodiment, the invention includes compounds wherein —X—Y— is —CF$_2$—O— or —O—CF$_2$—, in conjunction with any of the above or below embodiments.

In another embodiment of the present invention, the compounds, and solvates, hydrates, tautomers, stereoisomers and pharmaceutically acceptable salts thereof, are defined by Formula I, wherein each of R$^1$, R$^4$, R$^5$ and R$^8$, independently, is H, F, Cl, CF$_3$, OCF$_3$, methyl, ethyl, CN, OH, OCH$_3$, SCH$_3$, NHCH$_3$ or C(O)CH$_3$;

one of R$^2$ and R$^7$, independently, is phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of R$^9$;

the other of R$^2$ and R$^7$, independently, is C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl or —NH-benzyl, wherein the C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl and —NH-benzyl are optionally substituted, independently, with 1-3 substituents of R$^9$;

each of R$^3$ and R$^6$, independently, is H, halo, haloalkyl, haloalkoxyl, C$_{1-6}$ alkyl, CN, OH, OC$_{1-6}$-alkyl, SC$_{1-6}$-alkyl, NHC$_{1-6}$-alkyl or C(O)C$_{1-6}$-alkyl; and —X—Y— is —CR$^{10}$R$^{10}$—O—, —O—CR$^{10}$R$^{10}$—, —CR$^{10}$R$^{10}$—S— or —S—CR$^{10}$R$^{10}$, wherein each R$^{10}$, independently, is H or F, in conjunction with any of the above or below embodiments.

In another embodiment of the present invention, the compounds, and solvates, hydrates, tautomers, stereoisomers and pharmaceutically acceptable salts thereof, are defined by Formula I, wherein R$^2$ is halo, haloalkyl, haloalkoxyl, C$_{1-6}$-alkyl, C$_{2-4}$alkenyl, C$_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclobutyl, cyclopentyl or cyclohexyl, wherein the C$_{1-6}$-alkyl, C$_{2-4}$alkenyl, C$_{2-4}$alkynyl and ring are optionally substituted, independently, with 1-3 substituents of R$^{10}$;

each of R$^1$, R$^4$, R$^5$ and R$^8$, independently, is H, F, methyl, CN or OH;

each of R$^3$ and R$^6$, independently, is H, F, Cl, CF$_3$, methyl, CN, OH, OCH$_3$, SCH$_3$ or NHCH$_3$;

R$^7$ is a ring selected from phenyl, pyridyl, pyrimidyl, pyridazinyl, pyrazinyl, triazinyl or thiophenyl, said ring optionally substituted, independently, with 1-3 substituents of R$^{10}$; and —X—Y— is —CH$_2$—O— or —O—CH$_2$—, in conjunction with any of the above or below embodiments.

In another embodiment of the present invention, the compounds, and solvates, hydrates, tautomers, stereoisomers and pharmaceutically acceptable salts thereof, are defined by Formula II, wherein R$^1$ is H or F;
A$^3$ is CH, CF or N;
A$^4$ is CH, CF or N;
R$^5$ is H or F;
A$^6$ is CH, CF or N;
R$^8$ is H or F; and
—X—Y— is —CH$_2$—O— or —O—CH$_2$—, in conjunction with any of the above or below embodiments.

In another embodiment of the present invention, the compounds, and solvates, hydrates, tautomers, stereoisomers and pharmaceutically acceptable salts thereof, are defined by Formula II, wherein each of R$^1$, R$^4$, R$^5$ and R$^8$, independently, is H, F, Cl, CF$_3$, OCF$_3$, methyl, ethyl, CN, OH, OCH$_3$, SCH$_3$, NHCH$_3$ or C(O)CH$_3$;

one of R$^2$ and R$^7$, independently, is phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of R$^{10}$;

the other of R$^2$ and R$^7$, independently, is C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl or —NH-benzyl, wherein the C$_{1-6}$-alkyl, C$_{2-4}$alkenyl, C$_{2-4}$alkynyl, CN, —OC$_{1-6}$alkyl, —SC$_{1-6}$alkyl, —NHC$_{1-6}$alkyl, —N(C$_{1-3}$alkyl)$_2$, —NH-phenyl and —NH-benzyl are optionally substituted, independently, with 1-3 substituents of R$^{10}$;

each of R$^3$ and R$^6$, independently, is H, halo, haloalkyl, haloalkoxyl, C$_{1-6}$-alkyl, CN, OH, OC$_{1-6}$-alkyl, SC$_{1-6}$-alkyl, NHC$_{1-6}$-alkyl or C(O)C$_{1-6}$-alkyl; and —X—Y— is —CH$_2$—O—, —O—CH$_2$—, —CH$_2$—S— or —S—CH$_2$—, in conjunction with any of the above or below embodiments.

In another embodiment of the present invention, the compounds, and solvates, hydrates, tautomers, stereoisomers and pharmaceutically acceptable salts thereof, are defined by Formula II, wherein $R^2$ is Cl, Br, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclobutyl, cyclopentyl or cyclohexyl, wherein the $C_{1-6}$-alkyl, $C_{2-4}$alkenyl, $C_{2-4}$alkynyl and ring are optionally substituted, independently, with 1-3 substituents of $R^9$;

each of $R^1$, $R^4$, $R^5$ and $R^8$, independently, is H, F, methyl, CN or OH;

each of $R^3$ and $R^6$, independently, is H, F, Cl, $CF_3$, methyl, CN, OH, $OCH_3$, $SCH_3$ or $NHCH_3$;

$R^7$ is a ring selected from phenyl, pyridyl, pyrimidyl, pyridazinyl, pyrazinyl, triazinyl or thienyl, said ring optionally substituted, independently, with 1-3 substituents of $R^9$; and —X—Y— is —$CH_2$—O— or —O—$CH_2$—, in conjunction with any of the above or below embodiments.

In another embodiment of the present invention, the compounds, and solvates, hydrates, tautomers, stereoisomers and pharmaceutically acceptable salts thereof, are defined by Formula II, wherein $A^3$ is $CR^3$ or N;

$A^4$ is $CR^4$;

$R^2$ is Cl, Br, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclobutyl, cyclopentyl or cyclohexyl, wherein the $C_{1-6}$-alkyl, $C_{2-4}$alkenyl, $C_{2-4}$alkynyl and ring are optionally substituted, independently, with 1-3 substituents of $R^9$;

each of $R^1$, $R^4$, $R^5$ and $R^8$, independently, is H, F, methyl, CN or OH;

each of $R^3$ and $R^6$, independently, is H, F, Cl, $CF_3$, methyl, CN, OH, $OCH_3$, $SCH_3$ or $NHCH_3$;

$R^7$ is a ring selected from phenyl, pyridyl, pyrimidyl, pyridazinyl, pyrazinyl, triazinyl or thienyl, said ring optionally substituted, independently, with 1-3 substituents of $R^9$; and —X—Y— is —$CH_2$—O— or —O—$CH_2$—.

In another embodiment of the present invention, the compounds, and solvates, hydrates, tautomers, stereoisomers and pharmaceutically acceptable salts thereof, are defined by Formula II, wherein $A^3$ is N;

$A^4$ is $CR^4$;

$R^2$ is halo, haloalkyl, haloalkoxyl, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclobutyl, cyclopentyl or cyclohexyl, wherein the $C_{1-6}$-alkyl, $C_{2-4}$alkenyl, $C_{2-4}$alkynyl and ring are optionally substituted, independently, with 1-3 substituents of $R^{10}$;

each of $R^1$, $R^4$, $R^5$ and $R^8$, independently, is H, F, methyl, CN or OH;

$R^6$ is H, F, Cl, $CF_3$, methyl, CN, OH, $OCH_3$, $SCH_3$ or $NHCH_3$;

$R^7$ is a ring selected from phenyl, pyridyl, pyrimidyl, pyridazinyl, pyrazinyl, triazinyl or thiophenyl, said ring optionally substituted, independently, with 1-3 substituents of $R^9$; and —X—Y— is —$CH_2$—O— or —O—$CH_2$—.

In another embodiment of the present invention, the compounds, and solvates, hydrates, tautomers, stereoisomers and pharmaceutically acceptable salts thereof, are defined by Formula II, wherein $A^3$ is $CR^3$;

$A^4$ is $CR^4$ or N;

$R^2$ is halo, haloalkyl, haloalkoxyl, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclobutyl, cyclopentyl or cyclohexyl, wherein the $C_{1-6}$-alkyl, $C_{2-4}$alkenyl, $C_{2-4}$alkynyl and ring are optionally substituted, independently, with 1-3 substituents of $R^{10}$;

each of $R^1$, $R^4$, $R^5$ and $R^8$, independently, is H, F, methyl, CN or OH;

each of $R^3$ and $R^6$, independently, is H, F, Cl, $CF_3$, methyl, CN, OH, $OCH_3$, $SCH_3$ or $NHCH_3$;

$R^7$ is a ring selected from phenyl, pyridyl, pyrimidyl, pyridazinyl, pyrazinyl, triazinyl or thiophenyl, said ring optionally substituted, independently, with 1-3 substituents of $R^9$; and —X—Y— is —$CH_2$—O— or —O—$CH_2$—.

In another embodiment, the invention provides one or more of the compounds, or a pharmaceutically acceptable salt thereof, of Formulas I, II, III and IV, as taught and described herein.

In another embodiment, the invention provides the compound of Formula I, II, II-A, III or IV, or a stereoisomer or pharmaceutically acceptable salt thereof, selected from (5R/S)-7-(2-fluoro-3-pyridinyl)-3-(2-fluoro-4-pyridinyl)-6',7'-dihydrospiro[chromeno[2,3-c]pyridine-5,3'-[1,4]oxazepin]-5'-amine;

(5R)-7-(2-fluoro-3-pyridinyl)-3-(2-fluoro-4-pyridinyl)-6',7'-dihydrospiro[chromeno[2,3-c]pyridine-5,3'-[1,4]oxazepin]-5'-amine;

(5S)-7-(2-fluoro-3-pyridinyl)-3-(2-fluoro-4-pyridinyl)-6',7'-dihydrospiro[chromeno[2,3-c]pyridine-5,3'-[1,4]oxazepin]-5'-amine;

(5S)-7-bromo-3-chloro-6',7'-dihydro spiro[chromeno[2,3-c]pyridine-5,3'-[1,4]oxazepin]-5'-amine;

(5R)-7-bromo-3-chloro-6',7'-dihydrospiro[chromeno[2,3-c]pyridine-5,3'-[1,4]oxazepin]-5'-amine;

(3R/S)-2'-(2,2-dimethylpropoxy)-4'-fluoro-7'-(2-fluoro-3-pyridinyl)-6,7-dihydrospiro[1,4-oxazepine-3,9'-xanthen]-5-amine;

(3S)-2'-(2,2-dimethylpropoxy)-4'-fluoro-7'-(2-fluoro-3-pyridinyl)-6,7-dihydrospiro[1,4-oxazepine-3,9'-xanthen]-5-amine;

(3R)-2'-(2,2-dimethylpropoxy)-4'-fluoro-7'-(2-fluoro-3-pyridinyl)-6,7-dihydrospiro[1,4-oxazepine-3,9'-xanthen]-5-amine; and (5R)-7-(2-fluoro-3-pyridinyl)-3-(2-fluoro-4-pyridinyl)-6',7'-dihydro-2'H-spiro[chromeno[2,3-c]pyridine-5,5'-[1,4]oxazepin]-3'-amine.

All of the possible embodiments described herein for various of the R, X and Y groups of the compounds of Formula I may be applied, as appropriate, to compounds of Formulas II, III and IV, and any sub-formulas thereof.

In another embodiment, the invention provides each of the Examplary compounds, and stereoisomers, tautomers, solvates, pharmaceutically acceptable salts thereof, and related intermediates, described herein.

In another embodiment, the invention provides the exemplified compounds described herein, and stereoisomers and pharmaceutically acceptable salt forms of each thereof.

DEFINITIONS

The following definitions should assist in understanding the invention.

The term "comprising" is meant to be open ended, i.e., all encompassing and non-limiting. It may be used herein synonymously with "having" or "including." Comprising is intended to include each and every indicated or recited component or element(s) while not excluding any other components or elements.

The term "$C_{\alpha-\beta}$alkyl", when used either alone or within other terms such as "haloalkyl" and "alkylamino", embraces linear or branched hydrocarbon radicals having $\alpha$ to $\beta$ number of carbon atoms (such as $C_1$-$C_{10}$; $C_1$-$C_6$; or $C_1$-$C_4$). Unless otherwise specified, one or more carbon atoms of the "alkyl" radical may be substituted, such as with an —OH, CN or cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha-\beta}$alkenyl", when used alone or in combination, embraces linear or branched hydrocarbon radicals having at least one carbon-carbon double bond in a moiety having a number of carbon atoms in the range from $\alpha$ and $\beta$. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha-\beta}$alkynyl", when used alone or in combination, denotes linear or branched hydrocarbon radicals having at least one carbon-carbon triple bond in a moiety having a number of carbon atoms in the range from $\alpha$ and $\beta$. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$-alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include —O-methyl, —O-ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —OR$^7$ where R$^7$ may be defined as a $C_{\alpha-\beta}$-alkyl. Examples of such "alkenyl" radicals include —NH—CH$_2$CH=CH$_2$, —S—CH$_2$CH$_2$CH=CHCH$_3$ and the like. Similar examples exist for such "alkynyl" radicals, as appreciated by those skilled in the art.

The term "$C_{\alpha-\beta}$alkoxyl" or "—OC$_{\alpha-\beta}$alkyl" when used alone or in combination, embraces linear or branched oxygen-containing alkyl radicals each having $\alpha$ to $\beta$ number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy, tert-butoxy and neopentoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "$C_{\alpha-\beta}$-cycloalkyl", also referred to herein as "carbocyclic", when used alone or in combination, denotes a partially or fully saturated ring radical having a number of carbon atoms in the range from $\alpha$ and $\beta$. The "cycloalkyl" may contain one ("monocyclic"), two ("bicyclic") or even three ("tricyclic") rings wherein such rings may be attached together in a fused manner and each formed from carbon atoms. Examples of saturated carbocyclic radicals include saturated 3 to 6-membered monocyclic groups such as cyclopropane, cyclobutane, cyclopentane and cyclohexane. Cycloalkyls may be substituted as described herein.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents. This includes carbocyclics, heterocyclics, aryl and heteroaryl rings.

The term "halo", when used alone or in combination, means halogens such as fluorine (F), chlorine (Cl), bromine (Br) or iodine (I) atoms.

The term "haloalkyl", when used alone or in combination, embraces radicals wherein any one or more of the hydrogen atoms on the alkyl radical is replaced with a halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl (—CF$_3$), chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of heteroaryl radicals include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, aza-quinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The terms "heterocycle" or "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted" refers to a single ring of 3-, 4-, 5-, 6-, 7- or 8-atom membered or a 6-, 7-, 8-, 9-, 10-, 11 or 12-atom membered bicyclic ring system comprising the delineated number of atoms, the atoms being carbon or, where indicated, a heteroatom such as nitrogen (N), oxygen (O) or sulfur (S). Where the number of atoms is not delineated, such as a "monocyclic ring system" or a "bicyclic ring system", the numbers of atoms are 3-8 for a monocyclic and 6-12 for a bicyclic ring. The ring or ring system may contain substitutents thereon, attached at any atom that allows a stable compound to be formed. A bicyclic ring is intended to include fused ring systems as well as spiro-fused rings. This phrase encompasses carbocyclics, heterocyclics, aryl and heteroaryl rings.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, ($CH_3S$—).

The term "Formula I" includes any sub formulas, such as Formulas II, III and IV. Similar with Formulas II, III and IV, in that they include sub-formulas where described.

The term "pharmaceutically-acceptable" when used with reference to a compound of Formulas I-IV is intended to refer to a form of the compound that is safe for administration. For example, a salt form, a solvate, a hydrate, a prodrug or derivative form of a compound of Formulas I-IV, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-IV are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-IV may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-III include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, diisopropylethylamine and trimethylamine. All of these salts may be prepared by conventional means from the corresponding compound of the invention by reacting, for example, the appropriate acid or base with the compound of Formulas I-IV.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "pharmaceutically-acceptable derivative" as used herein, denotes a derivative which is pharmaceutically acceptable.

The compound(s) of Formulas I-IV may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I-IV. The compounds of Formulas I-IV can be synthesized according to the procedures described in the following Schemes 1, 2, 3a, 3b, 4 and 5, wherein the substituents are as defined for Formulas I-IV above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:
ACN, MeCN—acetonitrile
Aq., aq.—aqueous
Ar—argon (gas)
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1) iodide
DCC—dicyclohexylcarbodiimide
DEA—diethylamine
DIC—1,3-diisopropylcarbodiimide
DIEA, DIPEA—diisopropylethylamine
DME—dimethoxyethane
DMF—dimethylformamide
DMAP—4-dimethylaminopyridine
DMSO—dimethylsulfoxide
EDC, EDCI—1-(3-dimethylaminopropyl)-3-ethylcarbodiimide
$Et_2O$—diethyl ether
EtOAc—ethyl acetate
G, gm—gram
h, hr—hour
$H_2$—hydrogen (gas)
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LDA—Lithium diisopropylamide
LiOH—lithium hydroxide
$MgSO_4$—magnesium sulfate
MS—mass spectrum
MeOH—methanol
$N_2$—nitrogen (gas)
$NaCNBH_3$—sodium cyanoborohydride
$Na_2CO_3$—sodium carbonate
$NaHCO_3$—sodium bicarbonate
NaH—sodium hydride
NaI—sodium iodide
$NaBH_4$—sodium borohydride
NaOH—sodium hydroxide
$Na_2SO_4$—sodium sulfate
$NH_4Cl$—ammonium chloride
$NH_4OH$—ammonium hydroxide
$P(t-bu)_3$—tri(tert-butyl)phosphine
Pd/C—palladium on carbon
$Pd(PPh_3)_4$—palladium(0)triphenylphosphine tetrakis
$Pd(dppf)Cl_{12}$—palladium(1,1-bisdiphenylphosphinoferrocene) II chloride
$Pd(PhCN)_2Cl_2$—palladium di-cyanophenyl dichloride
$Pd(OAc)_2$—palladium acetate
$Pd_2(dba)_3$—tris(dibenzylideneacetone) dipalladium
PyBop—benzotriazol-1-yl-oxy-tripyrrolidino-phosphonium hexafluorophosphate
RT, rt—room temperature
RBF, rbf—round bottom flask
TLC, tlc—thin layer chromatography
TBAF—Tetrabutylammonium flouride
TBTU—O-benzotriazol-1-yl-N,N,N,N'-tetramethyluronium tetrafluoroborate
TEA, $Et_3N$—triethylamine
TFA—trifluoroacetic acid
THF—tetrahydrofuran
UV—ultraviolet light

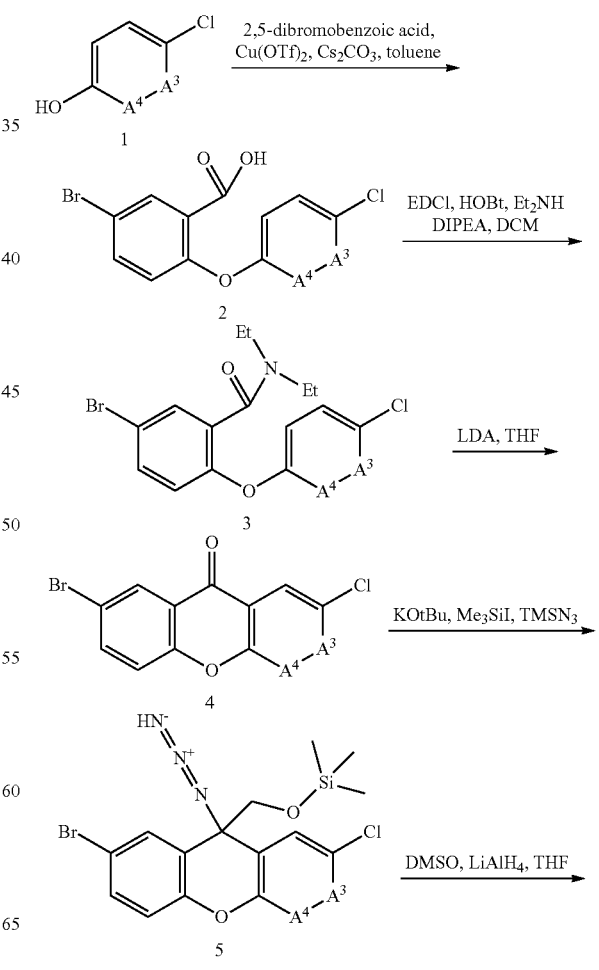

Scheme 1

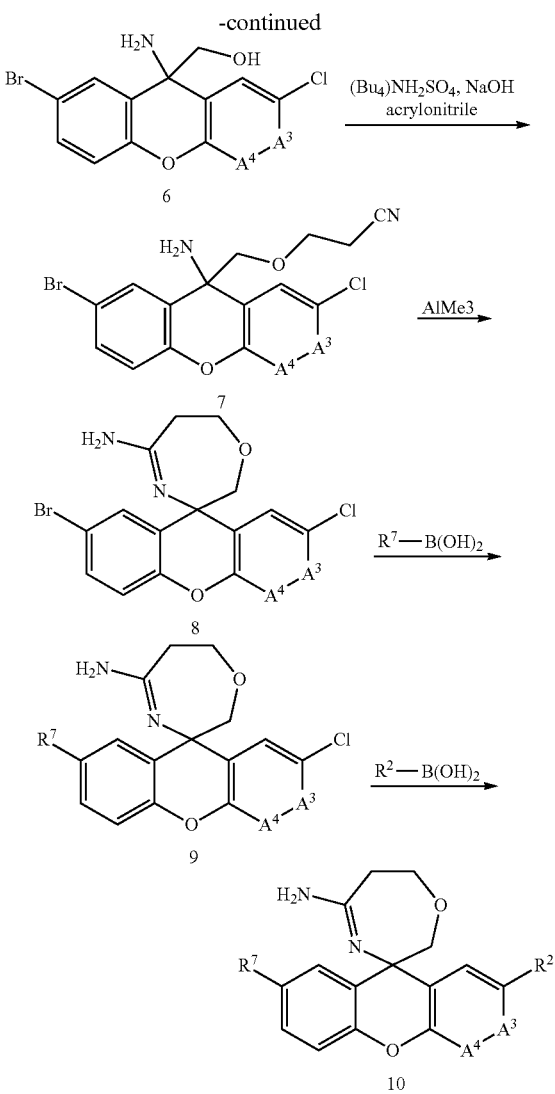

Scheme 1 describes an exemplary method for preparing racemic compounds 10 of Formulas I, II, III and IV, wherein $A^1, A^5, A^6$ and $A^8$ are each CH and either of $A^3$ and $A^4$ maybe $CR^3$ or N or $CR^4$ or N, respectively, and wherein Y is —O— and X is $CH_2$. One can start by reacting chloro-hydroxy-pyridine or chloro-phenol with 2,5-dibromobenzoic acid in the presence of a suitable base, such as cesium carbonate as shown above, to afford the ether linked adduct 2. The carboxylic acid of 2 may then be functionalized to the corresponding amide 3 under suitable conditions, such as those described herein, and treated with a strong base, such as LDA, to provide the corresponding ketone intermediate 4.

The intermediate 4 and similar intermediates may also be prepared in accordance to that described in PCT published patent application WO2010030954, pages 51, Scheme 1, compounds 1-4 and Example 1 on pg 59, lines 17-pg 60, line 10, each section of which is expressly incorporated herein by reference.

Ketone 4 can then be treated with a strong base, such as potassium t-butoxide, in the presence of trimethylsilane and trimethylsilylazide, as described above, to afford the azido-intermediate 5, which is generated in-situ and not isolated. The reactive azide 5 can be treated with a strong base, such as LAH as shown, to provide the corresponding amino-alcohol intermediate 6. The alcohol can then be converted to the corresponding ethyl-cyano ether moiety in compound 7, as described herein. The cyano-ether 7 can be cyclized to close the oxezapine ring and afford intermediate 8, using conventional methods, such as with trimethyl-aluminum, under the conditions shown above and described herein.

Intermediate 8 is an important intermediate as is allows one to prepare desired compounds of the invention with varied substituent groups at each of the $R^2$ and $R^7$ connections. For example, asn as shown above, desired $R^7$ moieties may be installed on intermediate 8 using conventional boronic acid chemistry, such as using Suzuki and similar conditions to attach a desired aromatic ring at $R^7$, to provide intermediate 9. Similarly, intermediate 9 may then be subjected to a second Suzuki or like boronic acid chemistry to afford the compounds of the invention 10.

The boronic acid, or boronic ester, intermediates utilized in steps above may be prepared by methods described in the following references: (1) PCT Int. Patent Appl. No. WO 2005073189, titled "Preparation of fused heteroaryl derivatives as p38 kinase inhibitors" or (2) PCT Int. Patent Appl. No. WO 2006094187, titled "Preparation of phthalazine, aza- and diaza-phthalazine compounds as protein kinase, especially p38 kinase, inhibitors for treating inflammation and related conditions". Also, desired boronic acids may be purchased commercially from vendor catalogs, such as from ASigma-Aldrich Chemicals for instance, or specially made by the vendor or by persons of ordinary skill in the art.

The Suzuki method is a reaction using a borane reagent, such as a boronic acid or ester such as a dioxaborolane, and a suitable leaving group containing reagent, such as the bromo-xanthene 4 (halogens, including bromides and chlorides are suitable halogen leaving groups "LG"). As appreciated to one of ordinary skill in the art, Suzuki reactions also utilize a palladium catalyst. Suitable palladium catalysts include, without limitation, $Pd(PPh_3)_4$, $Pd(OAc)_2$ or $Pd(dppf)Cl_2$. Where LG is a halide, the halide may be an iodide, a bromide or chloride. Chloro-pyridyl rings (where either of $A^3$ or $A^4$=N) undergo Suzuki reactions in the presence of Pd catalysts. Other LGs are also suitable. For example, Suzuki couplings are known to occur with a sulfonate, such as trifluoromethanesulfonate, as the leaving group.

The Suzuki reaction conditions may vary. For example, Suzuki reactions are generally run in the presence of a suitable base such as a carbonate base, bicarbonate or an acetate base, in a suitable solvent such as toluene, acetonitrile, DMF or an aqueous-organic solvent combination or a biphasic system of solvents. Further, the reaction may require heat depending upon the particular bromide 4 and/or boronic acid or ester, as appreciated by those skilled in the art. In addition, where the bromide is an aromatic moiety, such as phenyl, the reaction may be complete in a short period of time with heat.

Other coupling methods are known. For example metal catalyzed coupling chemistry, such Stille, Kumada, Negishi coupling methods, and the like, may be employed to the xanthene cores 4 to prepare desired cyclic products 8. In addition, compounds may possess groups which may need to be protected (and later deprotected), such as a free amino group, to carry out effective coupling reactions to install either $R^2$ or $R^7$ groups to afford the final desired compounds 10, as appreciated by persons of ordinary skill in the art.

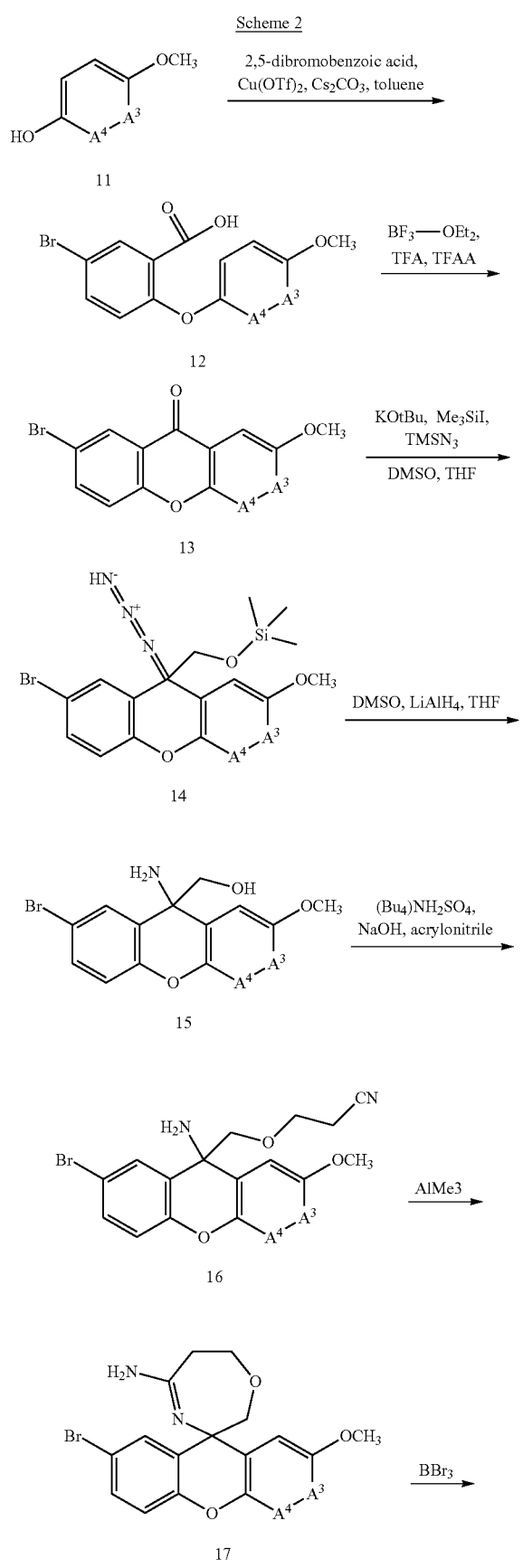

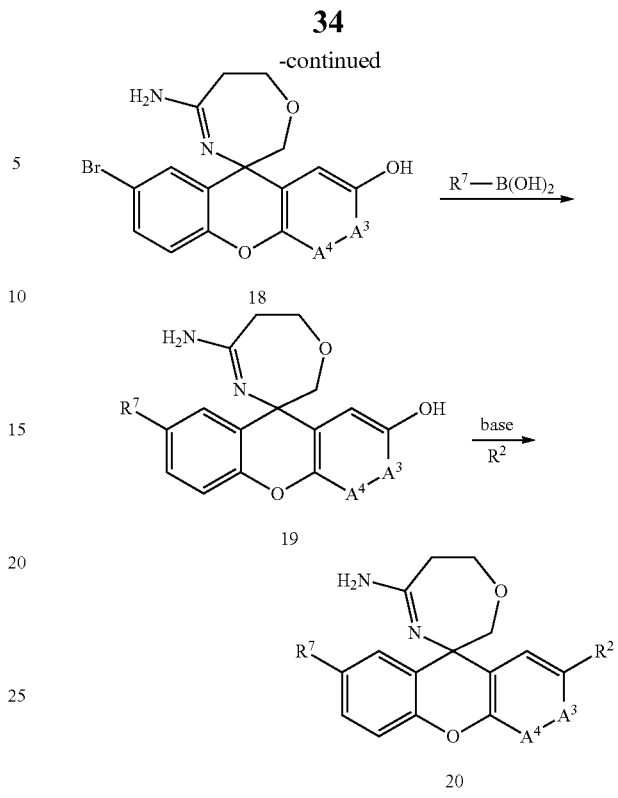

Scheme 2 describes an exemplary method for preparing racemic compounds 20 of Formulas I, II, III and IV, wherein $A^1$, $A^5$, $A^6$ and $A^8$ are each CH and either of $A^3$ and $A^4$ maybe $CR^3$ or N or $CR^4$ or N, respectively, and wherein Y is —O— and X is $CH_2$. One can start by reacting methoxy-hydroxy-pyridine or 4-methoxy-phenol with 2,5-dibromobenzoic acid in the presence of a suitable base, such as cesium carbonate as shown above, to afford the ether linked adduct 12. The carboxylic acid of 12 may then be functionalized to the corresponding amide 13 under suitable conditions, such as those described herein, and treated with a strong base, such as LDA, to provide the corresponding ketone intermediate 14.

The intermediate 13 and similar intermediates may also be prepared in accordance to that described in PCT published patent application WO2010030954, pages 53, Scheme 2, compounds 9-13; Scheme 3b on pg 55, compound 32; Example 1 on pg 59, lines 17-pg 60, line 10; Example 3 on pg 62; and Example 5-7 beginning on pg 65 of WO2010030954, each disclosure of which is expressly incorporated herein by reference.

Ketone 3 can then be treated with a strong base, such as potassium t-butoxide, in the presence of trimethylsilane and trimethylsilylazide, as described above, to afford the azido-intermediate 4, which is generated in-situ and not isolated. The reactive azide 4 can be treated with a strong base, such as LAH as shown, to provide the corresponding amino-alcohol intermediate 5. The alcohol can then be converted to the corresponding ethyl-cyano ether moiety in compound 6, as described herein. The cyano-ether 6 can be cyclized to close the oxezapine ring and afford intermediate 17, using conventional methods, such as with trimethyl-aluminum, under the conditions shown above and described herein. The methoxyl group of intermediate 17 can be reduced to the corresponding hydroxyl group intermediate 18 using known reagents, such as $BBr_3$, under suitable conditions, such as those described herein and in WO2010030954.

Intermediate 18 is an important intermediate as is allows one to prepare desired compounds of the invention with varied substituent groups at each of the $R^2$ and $R^7$ connections. For example, and as shown above, desired $R^7$ moieties may be installed on intermediate 18 using conventional Suzuki coupling methods via coupling at the site of the bromide, or Suzuki-like aromatic-halogen exchange reactions, which reactions generally employ a boronic acid moiety, a palladium catalyst reagent and a base. Other aryl/heteroaryl coupling methods, including Stille and the like under appropriate conditions, may also be employed to provide compounds 19. Similarly, intermediate 19 may then be subjected to a suitable base, such as cesium carbonate, followed by treatment with a desired alkyl-$R^2$ group to afford the O-linked $R^2$ compounds of the invention 20.

Alternatively, the hydroxyl group of compound 19 can be activated into a suitable leaving group ("LG" in scheme 1), such as a triflate, as known in the art and described in the literature, or other suitable O-linked leaving group. The leaving group of intermediate 19 (not shown) can then be reacted with a desired aromatic boronic acid to install the desired $R^2$ group, as shown in scheme 1, to afford the desired compounds 20 of Formulas I-IV.

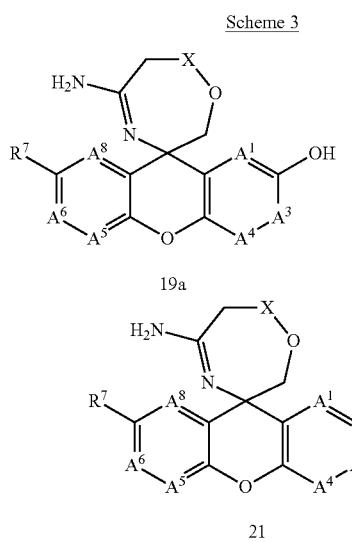

Desired compounds 21 of Formulas I, II, III and IV, and sub-formulas thereof, wherein the $R^2$ group is —OR may be made as generally described in Scheme 3. As shown, $R^7$-hydroxy intermediate 19a can be functionalized as desired, such as by alkylation as shown, by reaction with an alkyl halide 12 in the presence of a suitable base, such as cesium carbonate, in suitable solvents to afford the finally desired product 21.

"LG" in this instance is a "leaving group" which may be a halide such as an iodide, bromide, chloride or fluoride. LG may also be a non-halide moiety such as an alkylsulfonate or other known groups which generally form an electrophilic species ($E^+$). Coupling reactions generally occur more readily in one or a combination of solvents and a base. Suitable solvents include, without limitation, generally non-nucleophilic, anhydrous solvents such as toluene, $CH_2Cl_2$, THF, DMF, N,N-dimethylacetamide and the like. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH and the like, alkoxides such as $NaOCH_3$, and the like. The base itself may also serve as a solvent. These coupling reactions are generally fast and conversion occurs typically in ambient conditions. However, depending upon the particular substrate, such reactions may require heat, as appreciated by those skilled in the art.

37

-continued

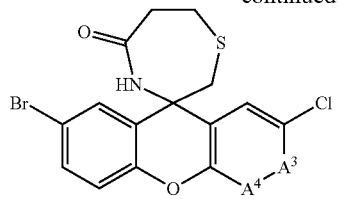

23

1. Lawesson's reagent
2. Me₃OBF₄
3. NH₄Cl, EtOH

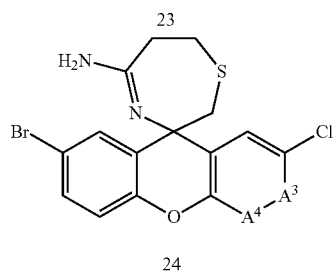

24

Method 1 or 2

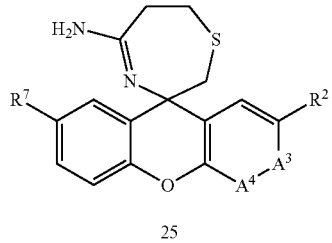

25

Scheme 4 describes an exemplary method for preparing racemic thiazepane compounds 25 of Formulas I, II, III and IV, wherein $A^1$, $A^5$, $A^6$ and $A^8$ are each CH and either of $A^3$ and $A^4$ maybe $CR^3$ or N or $CR^4$ or N, respectively, and wherein Y is —S— and X is $CH_2$. Generally, thiazepane compounds 25 (where either of X or Y is —S— and the other is $CH_2$) may be prepared by the relevant conditions and methods described in K. Shankaran et al. *Bioorg. Med. Chem. Lett.* (2004) 14 (23), 5907-5911.

As shown and described in scheme 1 above, the aminoalcohol intermediate 6 may be used in scheme 4. The amine group of intermediate 6 may be protected using conventional protection groups, such as BOC-anhydride as shown, followed by formation of intermediate 22 by activating the alcohol group in 6 and displacing it with the BOC-protected amine. The cyclic amine may be opened with mercaptoproprionic acid in the presence of a suitable base, such as cesium carbonate, to form the corresponding mercapto linker (not shown). The amine may then be deprotected using a suitable acid, such as HCl, and the acid in the mercapto linker can be activated using conventional activating groups, such as EDC in the presence of a suitable base, to provide the corresponding ring closed lactam 23. Lactam 23 may then be converted to the corresponding primary amine 24 using known methods, such as with Lawesson's Reagent as shown in scheme 4.

Chloro-Bromo-Intermediate 24 is an important intermediate as is allows one to prepare desired compounds of the invention with varied substituent groups at each of the $R^2$ and $R^7$ connections. For example, and as shown above in schemes 1 and 2, desired $R^7$ moieties may be installed on intermediate 24 using conventional boronic acid chemistry, such as using Suzuki and similar conditions to attach a desired aromatic ring at $R^7$, to provide a further intermediate (not shown). Similarly, the latter intermediate may then be subjected to a second Suzuki or like boronic acid chemistry to afford the compounds of the invention 25.

38

Scheme 5

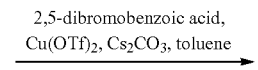

1

2,5-dibromobenzoic acid,
Cu(OTf)₂, Cs₂CO₃, toluene

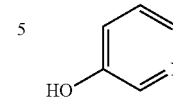

2

EDCl, HOBt, Et₂NH
DIPEA, DCM

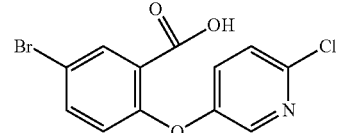

3

LDA, THF

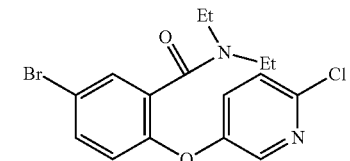

4

1. (S)-2-methylpropane-2-sulfinamide, Ti(OEt)₄
2. (2-tert-butoxy-2-oxoethyl)zinc chloride
3. DIBAL
4. BOC₂O
5. PPh₃, I₂

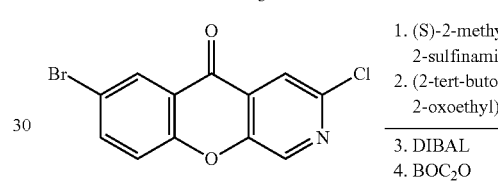

26

1. 2-mercaptoacetic acid, Cs₂CO₃
2. HCl
3. EDC-HCl, NMM

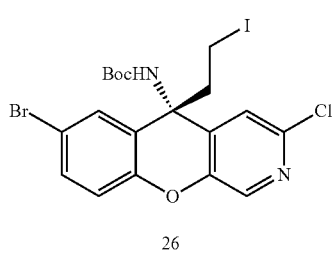

27

1. Lawesson's reagent
2. Me₃OBF₄
3. NH₄Cl, EtOH

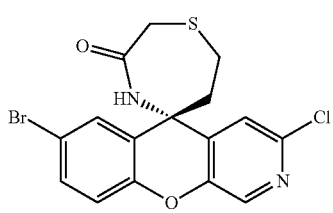

28

Method 1

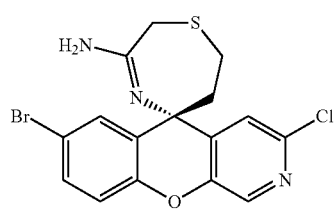

-continued

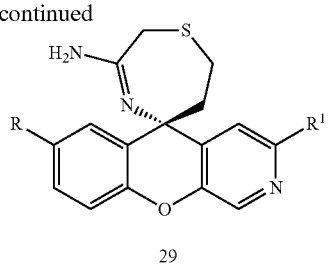

29

Scheme 5 describes an exemplary method for preparing racemic thiazepane compounds 29 of Formulas I, II, III and IV, wherein $A^1$, $A^5$, $A^6$ and $A^8$ are each CH and either of $A^3$ and $A^4$ maybe $CR^3$ or N or $CR^4$ or N, respectively, and wherein X is —S— and Y is $CH_2$. Generally, thiazepane compounds 29 (where either of X or Y is —S— and the other is $CH_2$) may be prepared by the relevant conditions and methods described in K. Shankaran et al. *Bioorg. Med. Chem. Lett.* (2004) 14 (23), 5907-5911.

As shown and described in scheme 1 above, the chloro-bromo-aza-xanthene-ketone intermediate 4 may be used in scheme 5. The ketone group of intermediate 4 may be subjected to reductive amination using the sulfonamide as shown above under suitable conditions, followed by reaction with t-butoxy-2-oxoethyl-zinc-chloride to afford the corresponding t-butyl ester (not shown). The ester may then be reduced down to the corresponding alcohol, using conventional methods, such as using DIBAL. The amine group can then be protected using conventional protection groups, such as BOC-anhydride as shown, followed by a Mitsunobu reaction wherein the primary alcohol can be converted to the corresponding iodide using standard Mitsunobu conditions, such as triphenylphosphine and a source of iodine, to provide intermediate 26. The iodo group can then be reacted with 2-mercaptoacidic acid to install the sulfide linkage ending with an acid group (not shown). The amine may then be deprotected using a suitable acid, such as HCl, and the acid group can be activated, similar to that described in scheme 4 above, and displaced with deprotected amine to afford the ring closed thiazepane lactam 27. Lactam 27 may then be converted to the corresponding primary amine 28 using known methods, such as with Lawesson's Reagent as shown in scheme 4.

Chloro-Bromo-Intermediate 28 is an important intermediate as is allows one to prepare desired compounds of the invention with varied substituent groups at each of the $R^2$ and $R^7$ connections. For example, and as shown above in schemes 1 and 2, desired $R^7$ moieties may be installed on intermediate 28 using conventional boronic acid chemistry, such as using Suzuki and similar conditions to attach a desired aromatic ring at $R^7$, to provide a further intermediate (not shown). Similarly, the latter intermediate may then be subjected to a second Suzuki or like boronic acid chemistry to afford the compounds of the invention 29.

Scheme 6

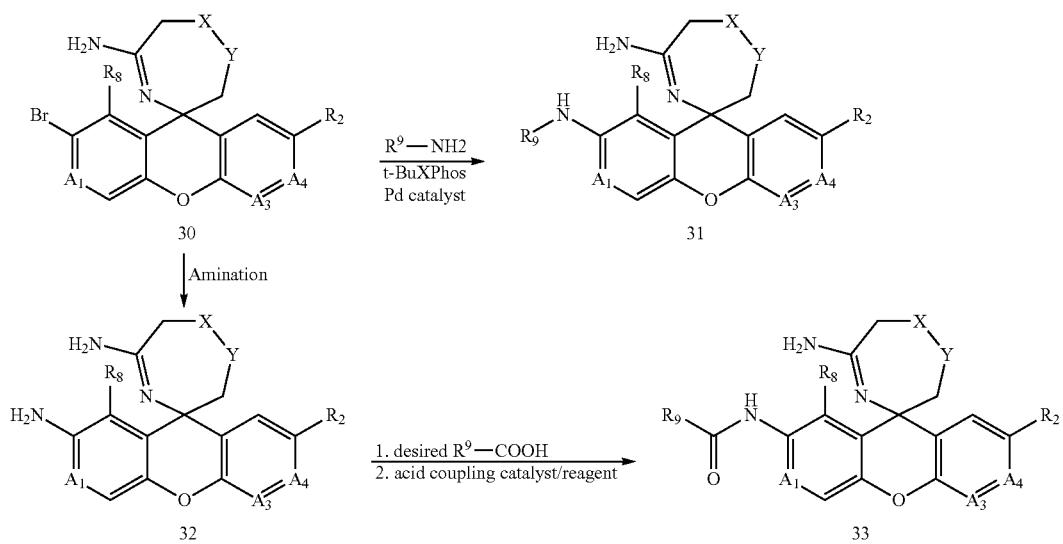

Desired compounds 33 of Formulas I-II, and sub-formulas thereof wherein $R^7$ is an amide or sulfonamide linker to desired $R^9$ groups may be made as generally described in Scheme 6. As shown, desired $R^9$ amines may be coupled directed to the bromide intermediate 30 using XPhos in the presence of a suitable palladium catalyst under suitable conditions to afford desired products 31.

Similarly, compound 30 can be transformed into the corresponding amine 32 using conditions like those described in scheme 1 hereinabove. Compound 32 may then be reacted with a desired acid in the presence of conventional amide coupling conditions to afford desired compound 33. Alternatively the $R^9$-acid may be converted to the corresponding acid-halide, such as a reactive acid-chloride using oxalyl chloride under suitable conditions, and reacted with the amine 32 in the presence of a suitable base and solvent to afford product 33.

EXAMPLES

The Examples, described herein below, represent various exemplary starting materials, intermediates and compounds of Formulas I-IV, which should assist in a better understanding and appreciation of the scope of the present invention and of the various methods that may be used to synthesize compounds of Formulas I-IV. Starting materials and intermediates used in the Examples herein may also be prepared using the procedures described in co-pending U.S. patent application Ser. No. 12/558,426, filed Sep. 11, 2009, which specification and disclosure is hereby incorporated herein by reference in its entirety. It should be appreciated that the general methods above and specific examples below are illustrative only, for the purpose of assistance and of understanding the present invention, and should not be construed as limiting the scope of the present invention in any manner.

Chromatography:

Unless otherwise indicated, crude product-containing residues were purified by passing the crude material or concentrate through either a Biotage or Isco brand silica gel column (pre-packed or individually packed with SiO$_2$) and eluting the product off the column with a solvent gradient as indicated. For example a description of (330 g SiO$_2$, 0-40% EtOAc/Hexane) means the product was obtained by elution from the column packed with 330 gms of silica, with a solvent gradient of 0% to 40% EtOAc in Hexanes.

Preparative HPLC Method:

Unless otherwise indicated, the compounds described herein were purified via reverse phase HPLC using one of the following instruments: Shimadzu, Varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument instrument or an Agilent 1100 series LC/MSD system. Compounds having an isotopic atom, such as bromine and the like, are generally reported according to the detected isotopic pattern, as appreciated by those skilled in the art.

The compounds disclosed and described herein have been named using either (1) the naming convention provided with Chem-Draw Ultra 11.0 software, available in Chem Office, or (2) by the ISIS database software (Advanced Chemistry Design Labs or ACD software).

Example 1

Intermediate A

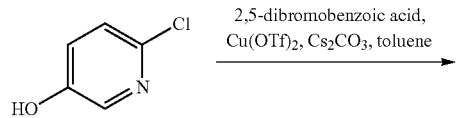

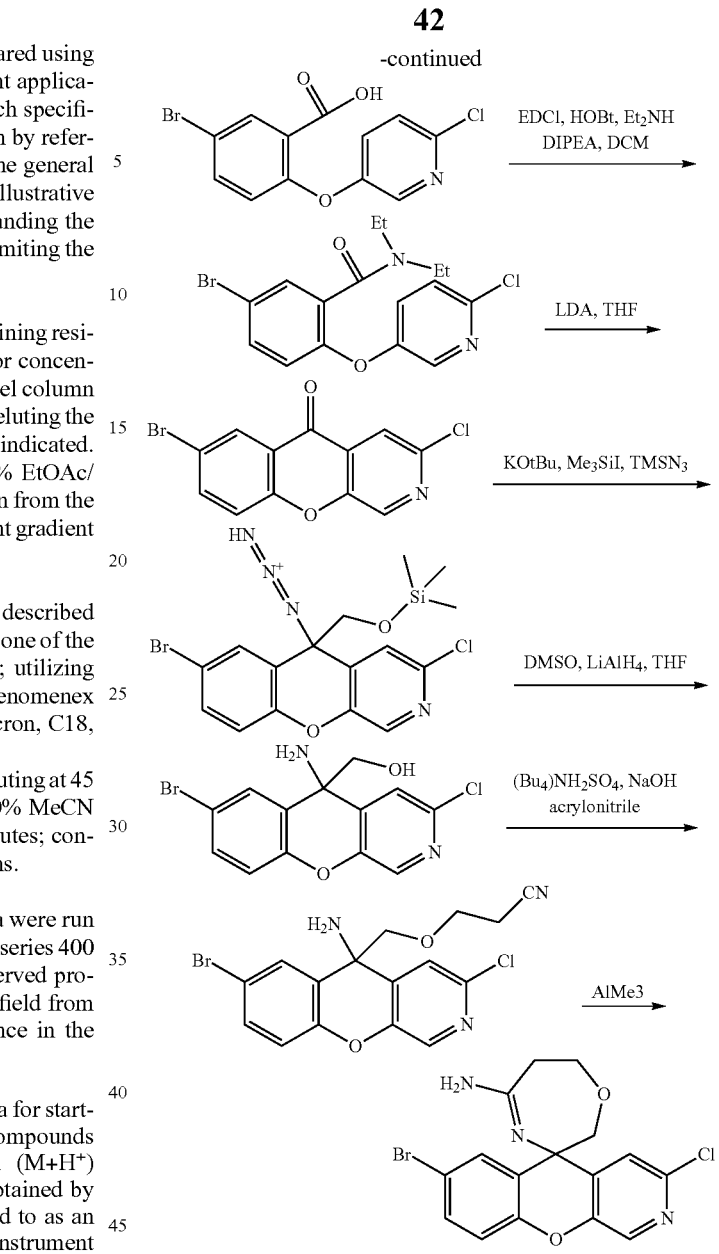

Synthesis of 7-bromo-3-chloro-6',7'-dihydro-2'H-spiro[chromeno[2,3-c]pyridine-5,3'-[1,4]oxazepin]-5'-amine Step 1: A RBF was charged with 2,5-dibromobenzoic acid (1244 g, 4.44 mol), 5-hydroxy-2-chloropyridine (663.3 g, 5.12 mol) and cesium carbonate (2893.3 g, 8.88 mol). The resulting mixture was stirred for 20 minutes under nitrogen atmosphere at which time copper (I) trifloromethanesulfonate toluene complex (59.7 g, 0.115 mol), toluene (9 L) and EtOAc (39 mL) were added in sequence. The resulting suspension was heated to 105° C. for 2 h and cooled to RT. The toluene was decanted and water (8 L) and EtOAc (8 L) were added to the residue. The mixture was stirred until the solids were completely dissolved. The organic layer was separated and the pH of the aqueous layer was adjusted to pH 2~3 with 6N HCl. This mixture was then extracted with EtOAc (3×5 L). The combined organic layers were dried over Na$_2$SO$_4$, filtered and concentrated to give 1.28 kg of 5-bromo-2-(6-chloropyridin-3-yloxy)benzoic acid as brown solid, which was used in next step without further purification.

Step 2: A mixture of 5-bromo-2-(6-chloropyridin-3-yloxy) benzoic acid (1.28 kg, 4.44 mol), diethylamine (461 mL, 4.44 mol), HOBT (600 g, 4.44 mol), DIPEA (1.547 L, 8.88 mol) in anhydrous DCM (8 L) was cooled to 0° C. EDCI (851.2 g, 4.44 mol) was added to the reaction mixture and it was stirred at 0° C. for 30 minutes and then at RT overnight. The reaction mixture was sequentially washed with aqueous $NaHCO_3$, brine and water before being dried over $MgSO_4$. Filtration and concentrated under reduced pressure provided a residue that was purified by silica gel chromatography (5-20% EtOAc in hexane) to provide 950 g of 5-bromo-2-(6-chloropyridin-3-yloxy)-N,N-diethylbenzamide.

Step 3: A solution of 5-bromo-2-(6-chloropyridin-3-yloxy)-N,N-diethylbenzamide (457.5 g, 1.23 mol) in THF (3 L) was cooled to −74 to −78° C. and treated with a solution of LDA (2M in heptane/THF/ethyl benzene, 2.25 L, 4.5 mol. After the addition was complete, the solution was stirred for 30 min at −78° C. The cold bath was removed and then the reaction was quenched with saturated aqueous $NH_4Cl$ (1 L), maintaining the temperature below 10° C. The mixture was added to an addition funnel and the layers were separated. The aqueous layer was extracted with EtOAc (3×2.5 L). The combined organic layers were dried over sodium sulfate, filtered and passed through a pad of silica gel. The filtrate was evaporated, and the residue was triturated with DCM to give 35 g of 7-bromo-3-chloro-5H-chromeno[2,3-c]pyridin-5-one. The mother liquor was evaporated and the solid thus obtained was purified by recrystallization using dichloromethane/hexanes to give 90 g of 7-bromo-3-chloro-5H-chromeno[2,3-c]pyridin-5-one.

Step 4: A 500-mL RBF was charged with 7-bromo-3-chloro-5H-chromeno[2,3-c]pyridin-5-one (12.3789 g, 39.9 mmol), trimethylsulfonium iodide (8.95 g, 43.9 mmol), and DMSO (199 mL). The resulting slurry was stirred vigorously for 5 minutes leading to a tan colored slurry before potassium 2-methylpropan-2-olate (4.92 g, 43.9 mmol) was added in one portion. The resulting reddish orange solution was maintained at RT for 2 hours at which time azidotrimethylsilane (10.49 mL, 80 mmol) was added in one portion. The heterogeneous mixture became homogeneous after 2-3 hours. The solution was maintained at RT overnight before being diluted with ethyl acetate and transferred to a separatory funnel containing saturated $NaHCO_3$ (500 mL). The layers were separated and the aqueous layer was extracted with EtOAc (3×250 mL). The combined organic layers were sequentially washed with water and brine before being dried over sodium sulfate, filtered and concentrated in vacuo to provide an orange oil that was evaporated from DCM (3×250 mL) to provide 5-azido-7-bromo-3-chloro-5-((trimethylsilyloxy)methyl)-5H-chromeno[2,3-c]pyridine as an orange foam that was carried on without further purification. The derived foam was dissolved in THF (250 mL) and cooled to 0° C. at which point LAH (2M in THF) (39.9 mL, 80 mmol) was added at a fast dropwise rate over 5-10 minutes. The reaction immediately became red upon the addition of LAH. The reaction was maintained at 0° C. for 2 hours then allowed to warm to RT for 30 minutes. The reaction was diluted with 150 mL of THF and quenched with by the addition of sodium sulfate decahydrate (38.5 g, 120 mmol), which was added over the course of 5 minutes. After the addition was complete the slurry was stirred at RT for 1.5 hours before being filtered through a pad of celite. The filter pad was washed with THF (5×100 mL, with agitation). The filtrate was concentrated under vacuum to give a brown foam. The foam was concentrated from DCM twise and left under vacuum overnight. The solid was taken up in DCM (75 mL) and heated to boiling for 1 minute. The mixture was cooled to RT, and then placed in the refrigerator for 1 hour. The resulting solid was filtered, washed with DCM (50 mL), and air-dried under a stream of $N_2$ (g) for 1 hour to provide (5-amino-7-bromo-3-chloro-5H-chromeno[2,3-c]pyridin-5-yl)methanol (8.94 g) as a light orange solid.

Step 5: A 200-mL RBF was charged with (5-amino-7-bromo-3-chloro-5H-chromeno[2,3-c]pyridin-5-yl)methanol (5.416 g, 15.86 mmol), tetrabutylammonium hydrogen sulfate (0.269 g, 0.793 mmol), THF (79 mL), and acrylonitrile (5.22 mL, 79 mmol) to give a clear, brown solution. NaOH (2N aq.) (19.82 mL, 39.6 mmol) was added, and the resulting biphasic mixture was stirred for 4 h. The mixture was diluted with water (110 mL) and extracted with EtOAc (3×50 mL). The combined organic extracts were washed with water (100 mL), washed with brine, dried over sodium sulfate, filtered, and concentrated. The crude product was purified by chromatography on silica gel (0-100% EtOAc/Hexane) to afford 3-((5-amino-7-bromo-3-chloro-5H-chromeno[2,3-c]pyridin-5-yl)methoxy)propanenitrile. $^1$H NMR (400 MHz, DMSO-$d_6$) δ=8.28 (d, J=0.4 Hz, 7 H), 7.98 (s, 7 H), 7.88 (d, J=0.4 Hz, 7 H), 7.50 (dd, J=2.5, 8.7 Hz, 8 H), 7.13 (d, J=8.7 Hz, 7 H), 3.61-3.48 (m, 2 H), 3.34 (t, J=6.0 Hz, 2 H), 2.95 (s, 2 H); MS m/z=394.0. Calc'd for $C_{16}H_{14}BrClN_3O_2$: 394.0.

Step 6: A 500-mL RBF was charged with 3-((5-amino-7-bromo-3-chloro-5H-chromeno[2,3-c]pyridin-5-yl)methoxy) propanenitrile (3.967 g, 10.05 mmol) and toluene (100 mL) to give a clear solution. Trimethylaluminum (10.55 mL of a 2M solution in toluene, 21.11 mmol) was added, and the resulting mixture was stirred for 5 min. A reflux condenser was attached, and the mixture was heated to reflux for 1 h. After the mixture had cooled to RT, a saturated aq. Rochelle's salt solution (200 mL) was slowly added. The mixture was stirred vigorously for 48 h and was then diluted with EtOAc (200 mL) and water (300 mL). The layers were separated, and the aq. layer was extracted with EtOAc (2×200 mL). The combined organic extracts were washed with water (200 mL), washed with brine, dried over sodium sulfate, filtered, and concentrated. The residue was taken up in DCM/MeOH and filtered to give 615 mg of the desired product an off-white solid. The filtrate was concentrated, and the residue was purified by chromatography on silica gel (0-10% MeOH/DCM). The product obtained from chromatography was combined with the above solid to give 7-bromo-3-chloro-6',7'-dihydro-2'H-spiro[chromeno[2,3-c]pyridine-5,3'-[1,4]oxazepin]-5'-amine as a cream-colored solid. $^1$H NMR (400 MHz, DMSO-$d_6$) δ=8.37 (d, J=0.4 Hz, 1 H), 7.62-7.43 (m, 2 H), 7.35 (s, 1 H), 7.22 (dd, J=0.5, 8.4 Hz, 1 H), 6.27 (br. s., 2 H), 3.94-3.72

(m, 2H), 3.70-3.47 (m, 2 H), 3.05-2.75 (m, 2 H). MS m/z=394.0. Calc'd for $C_{16}H_{14}BrClN_3O_2$: 394.0.

Example 2

Method 1: Using Intermediate A

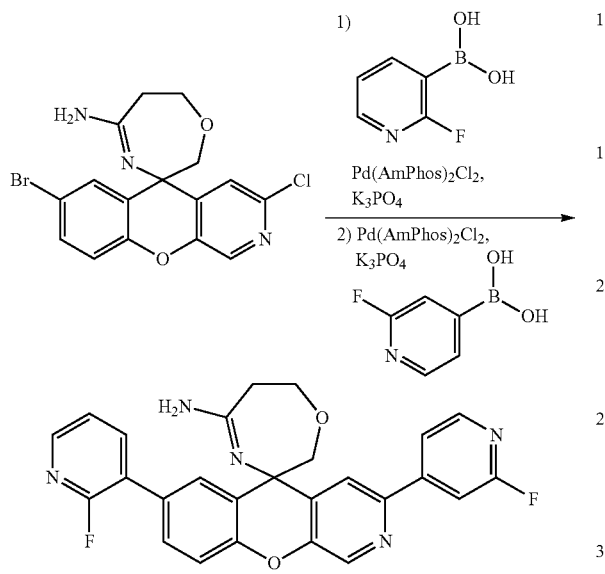

Synthesis of (E)-7-(2-fluoropyridin-3-yl)-3-(2-fluoropyridin-4-yl)-6',7'-dihydro-2'H-spiro[chromeno[2,3-c]pyridine-5,3'-[1,4]oxazepin]-5'-amine Step 1: A vial was charged with (E)-7-bromo-3-chloro-6',7'-dihydro-2'H-spiro[chromeno[2,3-c]pyridine-5,3'-[1,4]oxazepin]-5'-amine (280.9 mg, 0.712 mmol), 2-fluoropyridin-3-ylboronic acid (150 mg, 1.068 mmol), Pd(AmPhos)$_2$Cl$_2$ (25.2 mg, 0.036 mmol), and potassium phosphate (453 mg, 2.135 mmol). The vial was flushed with Ar (g), then 1,4-dioxane (2669 μL) and water (890 μL) were added in sequence. The vial was sealed and heated in a microwave reactor for 20 min at 90° C. The mixture was extracted with EtOAc (3×), and the combined organic extracts were concentrated. The crude product was purified by chromatography on silica gel (0-10% MeOH/DCM) to give (E)-3-chloro-7-(2-fluoropyridin-3-yl)-6',7'-dihydro-2'H-spiro[chromeno[2,3-c]pyridine-5,3'-[1,4]oxazepin]-5'-amine as a white solid.

MS m/z=411.0. Calc'd for $C_{21}H_{17}ClFN_4O_2$: 411.1.

Step 2: A vial was charged with (E)-3-chloro-7-(2-fluoropyridin-3-yl)-6',7'-dihydro-2'H-spiro[chromeno[2,3-c]pyridine-5,3'-[1,4]oxazepin]-5'-amine (142 mg, 0.346 mmol), 2-fluoropyridin-4-ylboronic acid (122 mg, 0.864 mmol), Pd(AmPhos)$_2$Cl$_2$ (12.24 mg, 0.017 mmol), and potassium phosphate (220 mg, 1.037 mmol). The vial was flushed with Ar (g), then dioxane (1296 μL) and water (432 μL) were added in sequence. The vial was sealed and heated in a microwave reactor for 30 min at 110° C. The mixture was extracted with EtOAc (3×), and the combined organic extracts were concentrated. The crude product was purified by chromatography on silica gel (10-100% of a 90:10:1 mixture of DCM/MeOH/NH$_4$OH in DCM) to give (E)-7-(2-fluoropyridin-3-yl)-3-(2-fluoropyridin-4-yl)-6',7'-dihydro-2'H-spiro[chromeno[2,3-c]pyridine-5,3'-[1,4]oxazepin]-5'-amine as a yellow solid. $^1$H NMR (400 MHz, DMSO-d$_6$) δ=8.71 (d, J=0.4 Hz, 1 H), 8.38 (d, J=5.3 Hz, 1 H), 8.26 (td, J=1.5, 4.8 Hz, 1 H), 8.13 (ddd, J=1.9, 7.5, 10.4 Hz, 1 H), 8.07 (s, 1 H), 7.95 (td, J=1.8, 5.2 Hz, 1 H), 7.72 (s, 1 H), 7.69-7.59 (m, 2 H), 7.50 (ddd, J=1.9, 4.9, 7.4 Hz, 1 H), 7.42 (d, J=8.6 Hz, 1 H), 6.16 (br. s., 2 H), 3.86 (t, J=5.6 Hz, 2 H), 3.72 (q, J=12.8 Hz, 2 H), 3.09-2.90 (m, 2 H). MS m/z=472.0. Calc'd for $C_{26}H_{20}F_2N_5O_2$: 472.2. The racemic material (104 mg) was subjected to chiral SFC separation, using 35% MeOH with diethylamine to afford 45 mg of the (R)-enantiomer (peak 1) and 44 mg of the (S)-enantiomer (peak 2) as white solids.

Example 3

Intermediate B

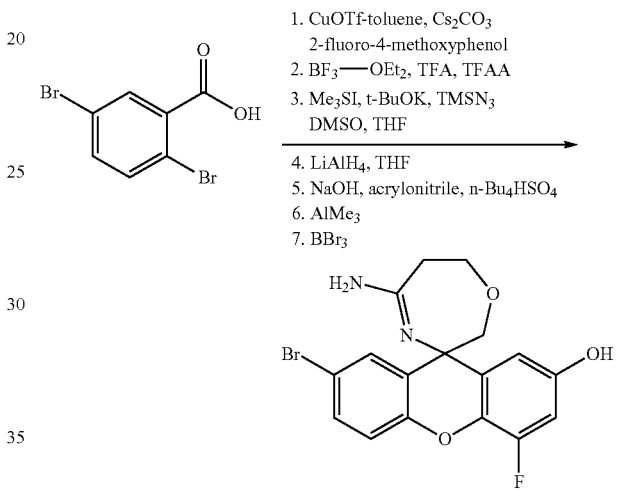

Synthesis of (E)-5-amino-7'-bromo-4'-fluoro-6,7-dihydro-2H-spiro[[1,4]oxazepine-3,9'-xanthen]-2'-ol Step 1: A dry 100 L glass jacketed reactor equipped with an addition funnel, reflux condenser, solids addition system and temperature probe was charged with 2,5-dibromobenzoic acid (2685 g, 9.6 mol) and copper (I) triflate toluene complex (2:1, 50.0 g, 0.2 mol). Toluene (30 L) and EtOAc (20 mL) were then charged, followed by 2-methoxy-4-fluorophenol (1500 g, 10.6 mol). With vigorous stirring cesium carbonate (6258 g, 19.2 mol) was added in portions. The mixture was heated to 90° C. for 4 hours. The mixture was cooled to 35° C. and water (15 L) was added. After 15 minutes of stirring the phases were sping and the aqueous phase was washed with toluene (7.5 L). With stirring, EtOAc (15.0 L) was added to the rich aqueous phase, followed by 6 M HCl (5.6 L) keeping the internal temperature below 30° C. The layers were separated and the organic layers were dried over magnesium sulfate, filtered through a pad of celite and concentration to provide a solid that was re-slurried in 915 mL of EtOAc and 9.2 L of heptanes. Stirring was continued for 1 hour before the solids were filtered and washed with heptanes. The resulting solids were dired to provide 2560 g of 5-bromo-2-(2-fluoro-4-methoxyphenoxy)benzoic acid as a cream colored solid.

Step 2: A dry 100 L glass jacketed reactor equipped with an addition funnel, reflux condenser and temperature probe was charged with 5-bromo-2-(2-fluoro-4-methoxyphenoxy)benzoic acid (2340 g, 6.9 mol). TFA (11.7 L) was carefully added to the solution followed by TFAA (1144 mL). Boron trifluoride diethyl etherate (85 mL, 0.68 mol) was then carefully added to the reaction mixture. The mixture was stirred for 4 hours at which point the reaction was transferred to another 100 L glass reactor containing 35.1 L of water cooled to 0° C. The resulting slurry was allowed to warm to RT and stir for 1 hour. The solids were filtered and washed with water (4.7 L) and 3 N NaOH (2×3.5 L) and water (7 L). The solids were transferred into a 22 L reactor and acetone (4.7 L) was added. The solids were slurried for 1.5 hour and the filtered, washing well with acetone (4.7 L). An additional slurry with acetone (6.4 L@ 45° C.) provided 1310 g of 7-bromo-4-fluoro-2-methoxy-9H-xanthen-9-one as an off white solid.

Step 3: To a suspension of 7-bromo-4-fluoro-2-methoxy-9H-xanthen-9-one (25.00 g, 77 mmol) and trimethylsulfonium iodide (23.68 g, 116 mmol) in DMSO (130 mL) and THF (130 mL) in 1 L RB flask was added potassium tert-butoxide (1M in THF) (116 mL, 116 mmol) dropwise over 10 minutes. Stirring was continued for 15 min at room temperature at which point trimethylsilyl azide (20.54 mL, 155 mmol) was added. The mixture was stirred for additional 40 minutes and then the reaction was quenched by addition of 100 ml of saturated aqueous sodium bicarbonate. After stirring for 10 minutes ethyl acetate (100 ml) and water (100 ml) were added and the layers were split. The organic layer was washed with water (3×100 ml) and brine (100 ml), then dried with $MgSO_4$, concentrated and dried in vacuo. The yellow residue was redissolved in 250 ml THF and cooled in an ice-water bath. Lithium aluminum hydride (1 M in THF) (108 mL, 108 mmol) was added dropwise and the mixture was stirred for 5 minutes at 0° C. before the bath was removed and the mixture was allowed to warm up to room temperature. The flask was re-cooled again in ice-water bath and sodium sulfate decahydrate (21.98 g, 155 mmol) was added in portions (be careful as there is rapid evolution of gas). The mixture was stirred for 5 minutes in the ice bath, and then the bath was removed. After dilution with 100 ml EtOAc, the gelatinous mixture was filtered through the pad of Celite and filter cake was washed with EtOAc (100 ml). The filtrate was concentrated and dried in vacuo. The yellow foam was redissolved in 60 ml DCM and a white solid crystallized immediately. The solid was filtered, washed with DCM (2×10 ml) and dried on air for 1 hr to afford a portion of desired product. The filtrate was concentrated under a stream of $N_2$ gas to ~¼ of the volume and the precipitated solid was filtered, washed quickly with DCM and dried on air to afford additional (9-amino-7-bromo-4-fluoro-2-methoxy-9H-xanthen-9-yl)methanol.

Step 4: A 100-mL RBF was charged with (9-amino-7-bromo-4-fluoro-2-methoxy-9H-xanthen-9-yl)methanol (2.318 g, 6.54 mmol), tetrabutylammonium hydrogen sulfate (0.111 g, 0.327 mmol), THF (32.7 mL), and acrylonitrile (2.154 mL, 32.7 mmol) to give a clear solution. NaOH (8.18 mL of a 2N aq. solution, 16.36 mmol) was added, and the resulting mixture was stirred for 1.5 h. The reaction mixture was diluted with EtOAc (70 mL), washed with water (2×50 mL), washed with brine, dried over sodium sulfate, filtered, and concentrated in vacuo. The crude product was purified by chromatography on silica gel (0-10% MeOH/DCM) to give 3-((9-amino-7-bromo-4-fluoro-2-methoxy-9H-xanthen-9-yl)methoxy)propanenitrile as a yellow solid. $^1$H NMR (400 MHz, DMSO-$d_6$) δ=7.97 (d, J=2.4 Hz, 1 H), 7.45 (dd, J=2.5, 8.7 Hz, 1 H), 7.19 (dd, J=1.7, 2.9 Hz, 1 H), 7.09 (d, J=8.6 Hz, 1 H), 6.96-6.89 (m, 1 H), 3.77 (s, 3 H), 3.64 (t, J=6.0 Hz, 1 H), 3.54-3.42 (m, J=2.1 Hz, 3 H), 3.38-3.23 (m, 2 H), 2.85-2.74 (m, 2 H).

Step 5: A 250-mL round-bottom flask was charged with 3-((9-amino-7-bromo-4-fluoro-2-methoxy-9H-xanthen-9-yl)methoxy)propanenitrile (2.78 g, 6.83 mmol) and toluene (45.5 mL) to give a pale-green solution. Trimethylaluminum (7.17 mL of a 2M solution in toluene, 14.34 mmol) was added, and a reflux condenser was attached. After stirring for 1 min, the flask was heated to 90° C. for 1 h. After this time, the mixture was cooled to RT. Sodium sulfate decahydrate (3.4 g) was added slowly over 5 min, and the mixture was stirred overnight. In the morning, the mixture was diluted with EtOAc (50 mL) and filtered through celite. The filter pad was washed with EtOAc (3×50 mL). The combined filtrates were concentrated to give a pale-yellow solid. The crude product was purified by chromatography on silica gel (0-10% MeOH/DCM) to give (E)-7'-bromo-4'-fluoro-2'-methoxy-6,7-dihydro-2H-spiro[[1,4]oxazepine-3,9'-xanthen]-5-amine as a white solid. $^1$H NMR (400 MHz, DMSO-$d_6$) δ=7.53 (d, J=2.4 Hz, 1 H), 7.47 (dd, J=2.5, 8.6 Hz, 1 H), 7.18 (d, J=8.6 Hz, 1 H), 6.95 (dd, J=2.9, 12.3 Hz, 1 H), 6.69 (dd, J=1.5, 2.9 Hz, 1 H), 6.15 (br. s., 2 H), 3.83-3.69 (m, 5 H), 3.64-3.45 (m, 2 H), 3.00-2.74 (m, 2 H). MS m/z=411.0. Calc'd for $C_{18}H_{17}BrFN_2O_3$: 407.1.

Step 6: A solution of (E)-7'-bromo-4'-fluoro-2'-methoxy-6,7-dihydro-2H-spiro[[1,4]oxazepine-3,9'-xanthen]-5-amine (0.990 g, 2.431 mmol) in DCM (24.31 mL) was cooled in an ice-bath for 5 min. Boron tribromide (0.919 mL, 9.72 mmol) was added dropwise to give a resulting brown mixture. The mixture was stirred for 1 h, at which time a saturated aq. sodium bicarbonate solution (25 mL) was added. The mixture was stirred for 5 min. and concentrated on a rotary evaporator to remove the DCM. The mixture was heated with a heat gun for 5 min, and at this point the solid was scraped from the sides of the flask. The flask was sonicated for 1 min, then reheated for 2 min. The flask was again sonicated for 1 min, then cooled to RT. The solid was filtered. The filter cake was washed twice with water, then air-dried under a stream of $N_2$ (g) for 1.5 h to give (E)-5-amino-7'-bromo-4'-fluoro-6,7-dihydro-2H-spiro[[1,4]oxazepine-3,9'-xanthen]-2'-ol as a light-yellow solid. The solid was used without further purification.

MS m/z=393.0. Calc'd for $C_{17}H_{15}BrFN_2O_3$: 393.0.

Example 4

Method 2: Using Intermediate B

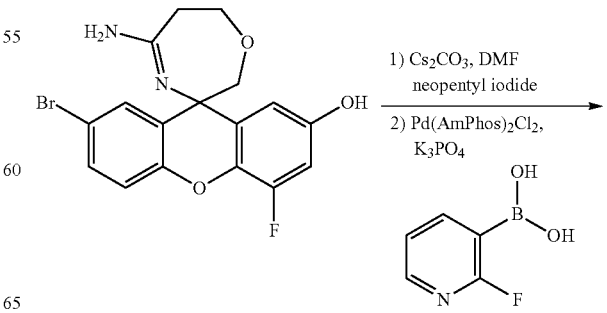

-continued

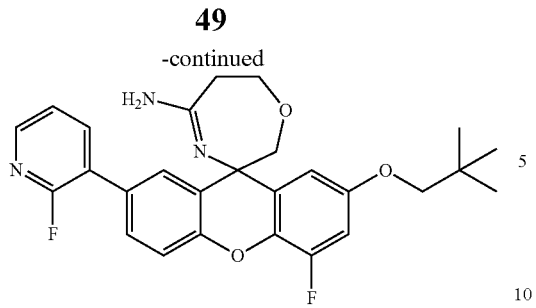

Synthesis of (E)-4'-fluoro-7'-(2-fluoropyridin-3-yl)-2'-(neopentyloxy)-6,7-dihydro-2H-spiro[[1,4]oxazepine-3,9'-xanthen]-5-amine Step 1: A vial was charged with (E)-5-amino-7'-bromo-4'-fluoro-6,7-dihydro-2H-spiro[[1,4]oxazepine-3,9'-xanthen]-2'-ol (222.7 mg, 0.566 mmol), cesium carbonate (738 mg, 2.265 mmol), and DMF (2832 µL) to give a yellow suspension. The resulting mixture was stirred for 10 min, then neopentyl iodide (225 µL, 1.699 mmol) was added. The vial was capped and heated to 100° C. for 2 h. The mixture was diluted with water and extracted with EtOAc (3×). The combined organic extracts were dried over sodium sulfate, filtered, and concentrated. The crude product was purified by chromatography on silica gel (0-10% MeOH/DCM) to give (E)-7'-bromo-4'-fluoro-2'-(neopentyloxy)-6,7-dihydro-2H-spiro[[1,4]oxazepine-3,9'-xanthen]-5-amine as a yellow oil.

MS m/z=463.0. Calc'd for $C_{22}H_{25}BrFN_2O_3$: 463.1.

Step 2: A vial was charged with (E)-7'-bromo-4'-fluoro-2'-(neopentyloxy)-6,7-dihydro-2H-spiro[[1,4]oxazepine-3,9'-xanthen]-5-amine (158 mg, 0.341 mmol), 2-fluoropyridin-3-ylboronic acid (96 mg, 0.682 mmol), potassium phosphate (217 mg, 1.023 mmol), and AmPhos (12.07 mg, 0.017 mmol) were added. The vial was flushed with Ar (g), then 1,4-dioxane (1279 µL) and water (426 µL) were added in sequence. The vial was heated to 90° for 45 min. The mixture was cooled to RT and extracted with EtOAc (3×). The combined organic extracts were concentrated, and the crude product was purified by chromatography on silica gel (10-100% of a 90:10:1 mixture of DCM/MeOH/NH$_4$OH in DCM) to give (E)-4'-fluoro-7'-(2-fluoropyridin-3-yl)-2'-(neopentyloxy)-6,7-dihydro-2H-spiro[[1,4]oxazepine-3,9'-xanthen]-5-amine as a light-yellow solid. $^1$H NMR (400 MHz, DMSO-d$_6$) δ=8.24 (td, J=1.5, 4.8 Hz, 1 H), 8.10 (ddd, J=1.9, 7.5, 10.4 Hz, 1 H), 7.64-7.53 (m, 2 H), 7.49 (ddd, J=1.9, 5.0, 7.3 Hz, 1 H), 7.34 (d, J=8.3 Hz, 1 H), 6.95 (dd, J=2.7, 12.4 Hz, 1 H), 6.81 (dd, J=1.4, 2.7 Hz, 1 H), 6.11 (br. s., 2 H), 3.84-3.69 (m, J=4.2 Hz, 2 H), 3.67-3.54 (m, 4 H), 2.98-2.75 (m, 2 H), 1.06-0.95 (m, 9 H). MS m/z=480.2. Calc'd for $C_{27}H_{28}F_2N_3O_3$: 480.2. The purified racemates (58 mg) were separated using a chiral SFC column, eluting with 55% MeOH with diethylamine, to afford (S)-enantiomer (peak 1) and (R)-enantiomer (peak 2) as white solids.

Example 5

Intermediate C

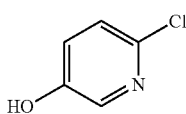

1. 2,5-dibromobenzoic acid, Cu(OTf)$_2$, Cs$_2$CO$_3$, toluene
2. EDCl, HOBt, Et$_2$NH DIPEA, DCM
3. LDA, THF
4. (R)-2-methylpropane-2-sulfinamide, Ti(OEt)$_4$
5. (2-tert-butoxy-2-oxoethyl)zinc (II) chloride
6. DIBAL
7. 2N aq. NaOH, nBu$_4$HSO$_4$, bromoacetonitrile
8. HCl then AlMe$_3$

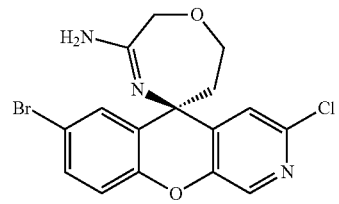

Synthesis of (E)-7-bromo-3-chloro-6',7'-dihydro-2'H-spiro[chromeno[2,3-c]pyridine-5,5'-[1,4]oxazepin]-3'-amine (Example 3A)

Steps 1-3: Steps 1-3 were carried out in accordance with that described in Example 1, Steps 1-3 hereinabove, to provide 90 g of 7-bromo-3-chloro-5H-chromeno[2,3-c]pyridin-5-one.

Step 4: A mixture of 7-bromo-3-chloro-5H-chromeno[2,3-c]pyridin-5-one (5.0 g, 48.3 mmol), (R)-2-methylpropane-2-sulfinamide (5.85 g, 48.3 mmol), and tetraethoxytitanium (10.00 mL, 48.3 mmol) in dry THF (100 mL) was heated at 75° C. for 24 hours. The solution was cooled to RT and slowly poured into a 2 L flask containing 0.35 L of brine and 0.35 L of saturated sodium bicarbonate. The resulting mixture was stirred vigorously for 15 minutes before being filtered through a pad of celite. The pad was washed with EtOAc. The filtrate was poured into a separatory funnel and the aqueous layer was extracted with EtOAc (2×500 mL). The combined organic layers were washed with brine, dried over sodium sulfate, filtered, and concentrated in vacuo to provide an orange solid. This solid was purified by silica gel chromatography using 0-15% Hexane/EtOAC to provide (R,E)-N-(7-bromo-3-chloro-5H-chromeno[2,3-c]pyridin-5-ylidene)-2-methylpropane-2-sulfinamide as an orange solid. M+H=415.0@2.90 min.

Step 5:

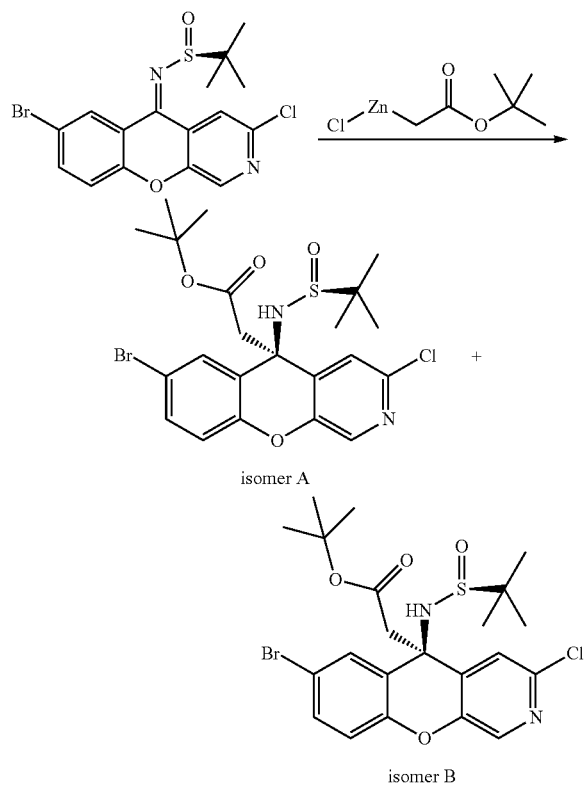

isomer A isomer B

To a solution of (S,Z)-N-(7-bromo-3-chloro-5H-chromeno [2,3-c]pyridin-5-ylidene)-2-methylpropane-2-sulfinamide (3000 mg, 7.25 mmol) in THF (25 mL) was slowly added 2-tert-butoxy-2-oxoethylzinc chloride (0.5 M in diethyl ether, 36.3 mL, 18.13 mmol) in an ice bath. The mixture was stirred at 0° C. for 25 mins, then 80 mL of saturated NH$_4$Cl aqueous solution was added to quench the reaction. The reaction mixture was extracted with EtOAc (2×35 mL). The organic extract was washed with saturated NaCl aqueous solution, dried over MgSO4, filtered and concentrated to give the crude material as an orange solid. The crude material was absorbed onto a plug of silica gel and purified by chromatography through a Redi-Sep pre-packed silica gel column (80 g), eluting with a gradient of 0% to 20% to 50% DCM/MeOH (90/10) in DCM. The fractions which contain mixture were repurified using 40 g Redi-Sep pre-packed silica gel column and eluting with a gradient of 0% to 20% to 50% DCM/MeOH (90/10) in DCM. The desired fractions were collected and concentrated to provide tert-butyl 2-((S)-7-bromo-3-chloro-5-((S)-1,1-dimethylethylsulfinamido)-5H-chromeno [2,3-c]pyridin-5-yl)acetate (isomer A, high Rf), and tert-butyl 2-((R)-7-bromo-3-chloro-5-((S)-1,1-dimethylethylsulfinamido)-5H-chromeno[2,3-c]pyridin-5-yl)acetate (isomer B, low Rf) as off-white solid. Isomer A: $^1$H NMR (400 MHz, DMSO-d$_6$) δ ppm 0.97 (s, 9 H) 1.03 (s, 9 H) 3.42 (s, 2 H) 6.41 (s, 1 H) 7.15 (d, J=8.71 Hz, 1 H) 7.52 (dd, J=8.80, 2.35 Hz, 1 H) 7.79 (s, 1 H) 7.98 (d, J=2.45 Hz, 1 H) 8.37 (s, 1 H). Isomer B: $^1$H NMR (400 MHz, DMSO-d$_6$) δ ppm 0.97 (s, 9 H) 1.04 (s, 9 H) 3.34 (s, 1 H) 3.42 (s, 1 H) 6.35 (s, 1 H) 7.16 (d, J=8.80 Hz, 1 H) 7.54 (dd, J=8.80, 2.45 Hz, 1 H) 7.77 (d, J=2.35 Hz, 1 H) 7.95 (s, 1 H) 8.35 (s, 1 H).

Step 6: A solution of tert-butyl 2-(7-bromo-3-chloro-5-(1,1-dimethylethylsulfinamido)-5H-chromeno[2,3-c]pyridin-5-yl)acetate (isomer A) (720 mg, 1.359 mmol) in dry THF (5.5 mL) was brought to −78° C. and diisobutylaluminum hydride (5.44 mL, 5.44 mmol) was added slowly. The mixture was brought to 0° C. after diisobutylaluminum hydride addition, and stirred at this temperature for 0.5 hr. The reaction mixture was quenched with saturated Rochelle's salt (~40 mL) and stirred at RT for overnight. The organic layer was separated and the aqueous phase was extracted by EtOAc. The combined organics were washed with saturated NaCl aqueous solution, dried over MgSO$_4$, filtered, and concentrated to afford N-(7-bromo-3-chloro-5-(2-hydroxyethyl)-5H-chromeno[2,3-c]pyridin-5-yl)-2-methylpropane-2-sulfinamide as off-white solid that was advanced without further purification.

Step 7: A 100 mL RBF was charged with N-(7-bromo-3-chloro-5-(2-hydroxyethyl)-5H-chromeno[2,3-c]pyridin-5-yl)-2-methylpropane-2-sulfinamide (625 mg, 1.359 mmol), tetrabutylammonium hydrogen sulfate (138 mg, 0.408 mmol), THF (6.80 mL), and bromoacetonitrile (0.852 mL, 12.23 mmol) to give a cloudy, light brown solution. The resulting solution was stirred vigorously for 5 min. Then a 2N aq. solution of sodium hydroxide (13.600 mL, 27.2 mmol) was added in one portion. The solution changed into dark brown color. 3 Hrs later, LCMS showed an incomplete conversion (SM: product=1:1.5). 1 additional molar equivalent of BrCH2CN was added, and the mixture was stirred for 1 hr. The reaction mixture was diluted with water and extracted with EtOAc. The organic extract was washed with saturated NaCl aqueous solution, dried over MgSO4, filtered and concentrated to give the crude material as a brown solid. The crude material was absorbed onto a plug of silica gel and purified by chromatography through a Redi-Sep pre-packed silica gel column (12 g), eluting with a gradient of 25 to 40 to 80% DCM/MeOH/NH4OH (90:10:1) in 40% EtOAc in heptane to yield N-(7-bromo-3-chloro-5-(2-(cyanomethoxy) ethyl)-5H-chromeno[2,3-c]pyridin-5-yl)-2-methylpropane-2-sulfinamide as off-white solid. $^1$H NMR (400 MHz, DMSO-d$_6$) δ ppm 1.06-1.12 (m, 9 H) 2.59 (d, J=9.49 Hz, 2 H) 3.03 (s, 2 H) 4.10 (s, 2 H) 6.52 (s, 1 H) 7.10-7.20 (m, 1 H) 7.51-7.59 (m, 1 H) 7.72-7.80 (m, 1 H) 7.93 (d, J=2.45 Hz, 1 H) 8.33-8.40 (m, 1 H).

Step 8: To a vial was added N-(7-bromo-3-chloro-5-(2-(cyanomethoxy)ethyl)-5H-chromeno[2,3-c]pyridin-5-yl)-2-methylpropane-2-sulfinamide (242 mg, 0.485 mmol) and HCl (4.0M solution in 1,4-dioxane, 0.970 mL, 3.88 mmol) in dioxane (4 mL). The mixture was stirred at RT for 20 mins, then quenched with 5 mL of a saturated aqueous solution of Na$_2$CO$_3$ and extracted into EtOAc. The organic extract was washed with saturated NaCl aqueous solution, dried over MgSO$_4$, filtered and concentrated to give the crude product as orange oil. The crude product was dissolved with 4 mL of toluene and trimethylaluminum solution (2M in toluene, 0.728 mL, 1.455 mmol) was added to the mixture (exothermic after addition). The mixture was heated to 90° C. in oil bath for 10 min, then quenched with Rochelle's salt (12 mL) at 0° C. and stirred overnight at RT. The reaction mixture was diluted with water and extracted with EtOAc (10 mL×2). The organic extract was washed with saturated NaCl aqueous solution, dried over MgSO$_4$, filtered and concentrated to give the crude material as orange oil. It was absorbed onto a plug of silica gel and purified by chromatography through a gold Redi-Sep pre-packed silica gel column (12 g), eluting with a gradient of 30% to 50% to 80% DCM/MeOH/NH4OH (90/10/1) in 40% EtOAc in Heptane to provide (E)-7-bromo-3-chloro-6′,7′-dihydro-2′H-spiro[chromeno[2,3-c]pyridine-5, 5′-[1,4]oxazepin]-3′-amine as off-white solid. $^1$H NMR (400 MHz, DMSO-d$_6$) δ ppm 2.03-2.22 (m, 4 H) 4.42 (s, 2 H) 6.18

(br. s., 2 H) 7.21 (d, J=8.51 Hz, 1 H) 7.39 (s, 1 H) 7.45-7.62 (m, 2 H) 8.36 (s, 1 H). The other stereoisomer is Example 3B in Table 1.

Example 6

Method 1: Using Intermediate C

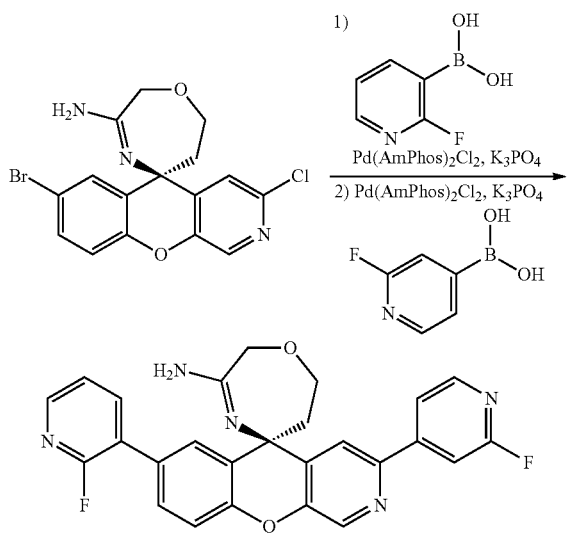

Synthesis of (R,E)-7-(2-fluoropyridin-3-yl)-3-(2-fluoropyridin-4-yl)-6',7'-dihydro-2'H-spiro[chromeno[2,3-c]pyridine-5,5'-[1,4]oxazepin]-3'-amine Step 1: To a vial was added (E)-7-bromo-3-chloro-6',7'-dihydro-2'H-spiro[chromeno[2,3-c]pyridine-5,5'-[1,4]oxazepin]-3'-amine (80 mg, 0.203 mmol), potassium phosphate (129 mg, 0.608 mmol), 2-fluoropyridin-3-ylboronic acid (30.0 mg, 0.213 mmol), 1,1-bis[(di-t-butyl-p-dimethylaminophenyl]palladium(ii) chloride (7.18 mg, 10.14 μmol), dioxane (1014 μL), water (338 μL). The resulting mixture was purged with $N_2$ gas and heated at 90° C. in microwave reactor for 25 mins. It was diluted with water and extracted into EtOAc. The organic extract was washed with saturated NaCl aqueous solution, dried over $MgSO_4$, filtered and concentrated to give the crude material as a orange solid. The crude material was absorbed onto a plug of silica gel and purified by chromatography through a gold Redi-Sep pre-packed silica gel column (12 g), eluting with a gradient of 50% to 80% DCM/MeOH/NH4OH (90/10/1) in 40% EtOAc in Heptane, to provide (E)-3-chloro-7-(2-fluoropyridin-3-yl)-6',7'-dihydro-2'H-spiro[chromeno[2,3-c]pyridine-5,5'-[1,4]oxazepin]-3'-amine as off-white solid.

Step 2: To a vial was added (E)-3-chloro-7-(2-fluoropyridin-3-yl)-6',7'-dihydro-2'H-spiro[chromeno[2,3-c]pyridine-5,5'-[1,4]oxazepin]-3'-amine (50 mg, 0.122 mmol), potassium phosphate (78 mg, 0.365 mmol), 2-fluoropyridin-4-ylboronic acid (34.3 mg, 0.243 mmol), and 1,1-bis[(di-t-butyl-p-dimethylaminophenyl]palladium(ii) chloride (4.31 mg, 6.09 μmol), dioxane (609 μL) and water (203 μL). The reaction mixture was purged with $N_2$ gas and heated at 100° C. in microwave reactor for 15 mins. It was diluted with water and extracted with EtOAc. The organic extract was washed with saturated NaCl aqueous solution, dried over $MgSO_4$, filtered and concentrated in vacuo to give the crude material. The crude was absorbed onto a plug of silica gel and purified by chromatography through a Redi-Sep pre-packed silica gel column (12 g), eluting with a gradient of 25% to 40% to 80% DCM/MeOH (90/10) in DCM, to provide (R,E)-7-(2-fluoropyridin-3-yl)-3-(2-fluoropyridin-4-yl)-6',7'-dihydro-2'H-spiro[chromeno[2,3-c]pyridine-5,5'-[1,4]oxazepin]-3'-amine as off-white solid. MS m/z=472.0. $^1$H NMR (400 MHz, DMSO-$d_6$) δ ppm 2.01-2.14 (m, 1 H) 2.24-2.41 (m, 1 H) 3.39 (dt, J=11.25, 5.62 Hz, 2 H) 4.37-4.47 (m, 1 H) 4.47-4.61 (m, 1 H) 6.13 (br. s., 2 H) 7.41 (d, J=8.31 Hz, 1 H) 7.50 (ddd, J=7.26, 5.01, 1.91 Hz, 1 H) 7.60 (dt, J=8.39, 1.87 Hz, 1 H) 7.67-7.75 (m, 2 H) 7.89-7.95 (m, 1 H) 8.03-8.16 (m, 2 H) 8.25 (dt, J=4.82, 1.50 Hz, 1 H) 8.38 (d, J=5.28 Hz, 1 H) 8.66-8.77 (m, 1 H).

Example 7

Method 3: Using Intermediate C—(S)-enantiomer

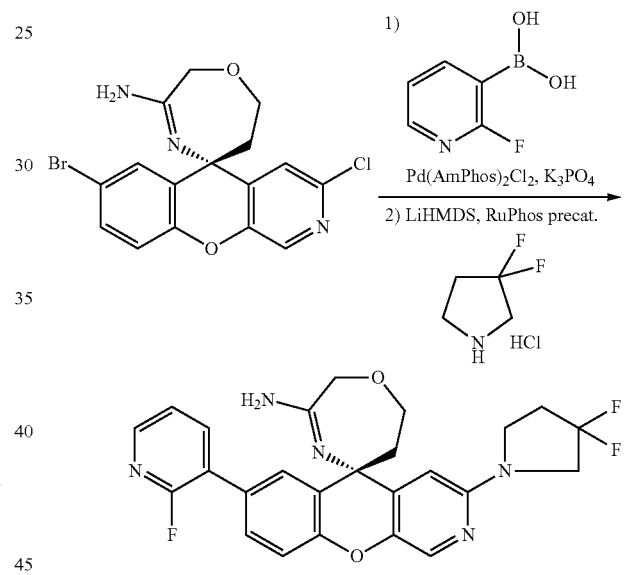

Synthesis of (S)-3-(3,3-difluoropyrrolidin-1-yl)-7-(2-fluoropyridin-3-yl)-6',7'-dihydro-2'H-spiro[chromeno[2,3-c]pyridine-5,5'-[1,4]oxazepin]-3'-amine Step 1: The first step was run in accordance with that described above in Example 6, Step 1 to afford the same product. Yield: 43.1%. $^1$H NMR (400 MHz, DMSO-$d_6$) δ ppm 2.06-2.15 (m, 1 H) 2.15-2.25 (m, 1 H) 3.22-3.40 (m, 2 H) 4.33-4.51 (m, 2 H) 6.13 (br. s., 2 H) 7.37 (d, J=8.41 Hz, 1 H) 7.44 (s, 1 H) 7.49 (ddd, J=7.24, 4.99, 1.86 Hz, 1 H) 7.58 (dt, J=8.44, 1.90 Hz, 1 H) 7.64 (s, 1 H) 8.01-8.11 (m, 1 H) 8.20-8.29 (m, 1 H) 8.39 (s, 1 H).

Step 2: A vial was charged with (S)-3-chloro-7-(2-fluoropyridin-3-yl)-6',7'-dihydro-2'H-spiro[chromeno[2,3-c]pyridine-5,5'-[1,4]oxazepin]-3'-amine (50.0 mg, 0.122 mmol), 3,3-difluoropyrrolidine hydrochloride (36.0 mg, 0.243 mmol), and RuPhos precatalyst (8.87 mg, 0.012 mmol). The vial was flushed with $N_2$ gas, then lithium bis(trimethylsilyl)amide (1M in THF) (608 μl, 0.608 mmol) was added slowly to the mixture. After about 10 mins, the mixture was diluted with saturated aqueous ammonium chloride and extracted with EtOAc. The combined organic extracts were dried over MgSO$_4$, filtered, and concentrated. The residue was purified on a 12 g Redi-Sep Gold silica-gel column eluting with a 90:10:1 mixture of DCM/MeOH/NH$_4$OH in EtOAc to provide (S)-3-(3,3-difluoropyrrolidin-1-yl)-7-(2-fluoropyridin-3-yl)-6',7'-dihydro-2'H-spiro[chromeno [2,3-c]pyridine-5,5'-[1,4]oxazepin]-3'-amine as off white solid. $^1$H NMR (500 MHz, DMSO-d$_6$) δ ppm 2.06 (br. s., 1 H) 2.14 (br. s., 1 H) 2.51-2.61 (m, 2 H) 3.33-3.41 (m, 2 H) 3.58 (t, J=7.59 Hz, 2 H) 3.81 (t, J=13.04 Hz, 2 H) 4.34-4.46 (m, 2 H) 6.00 (br. s., 2 H) 6.57 (s, 1 H) 7.28 (d, J=8.33 Hz, 1 H) 7.48 (t, J=5.34 Hz, 1 H) 7.53 (d, J=8.76 Hz, 1 H) 7.62 (s, 1 H) 8.00-8.07 (m, 1 H) 8.10 (s, 1 H) 8.22 (d, J=4.06 Hz, 1 H).

Example 8

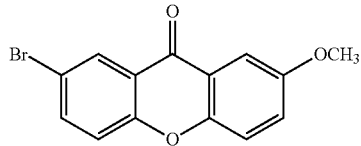

Synthesis of 2-Bromo-7-methoxy-9H-xanthen-9-one

Step 1: 2-(4-Bromophenoxy)-5-methoxybenzoic acid

4-Bromophenol (8.7 g, 50 mmol), Cs$_2$CO$_3$ (16 g, 50 mmol), CuOTf toluene complex (2:1) (0.625 mmol, 5 mol % Cu, 150 mg), ethyl acetate (0.25 ml, 2.5 mmol) were added to a solution of 2-bromo-5-methoxybenzoic acid (11.6 g, 50 mmol) in toluene (40 mL) in a sealed tube. The reaction mixture was purged with N$_2$, and was heated to 110° C. until the aryl halide was consumed as determined by LC-MS (48 h). After cooling to RT, the mixture was filtered through a Celite plug. The Celite plug was washed with EtOAc. The mixture was acidified by 1N HCl, and extracted w/EtOAc. The combined organic phases were washed with brine, dried over anhydrous sodium sulfate, filtered, and concentrated. This residue was purified via column chromatography on silica gel (gradient elution with 0-10% MeOH/DCM) to afford 2-(4-bromophenoxy)-5-methoxybenzoic acid. MS m/z=324.9 [M+H]$^+$. Calc'd for C$_{14}$H$_{11}$BrO$_4$: 323.1.

Step 2: 2-Bromo-7-methoxy-9H-xanthen-9-one

Sulfuric acid (41 ml, 765 mmol) was added to 2-(4-bromophenoxy)-5-methoxybenzoic acid (3750 mg, 12 mmol) at RT. The reaction mixture was stirred at 60° C. for 60 min. LCMS showed complete reaction. The reaction mixture was cooled to RT and poured slowly over stirred mixture of ice and water (100 ml). The tan precipitate was filtered and washed with water (3×30 ml), twice with 30 ml of 0.5N NaOH, and with water again. The residue was recrystallized from 40 ml THF to give the title compound. MS m/z=307.2 [M+H]$^+$. Calc'd for C$_{14}$H$_9$BrO$_3$: 305.1.

Example 9

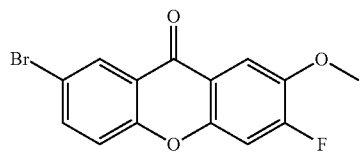 [SMILES: COc1cc2c(=O)c3cc(Br)ccc3oc2cc1F]

Synthesis of 7-Bromo-3-fluoro-2-methoxy-9H-xanthen-9-one

The titled compound was prepared using 2-bromo-4-fluoro-5-methoxybenzoic acid as the starting material, which starting material was prepared as follows:

Step 1: 4-Bromo-2-fluoro-5-methylphenol 2-fluoro-5-methylphenol (23.8 g, 0.19 mol) and bromine (9.7 ml, 0.19 mol) are combined in 50 ml of glacial acetic acid and stirred at RT for one hour. Acetic acid was removed under vacuum. The liquid was diluted with ethyl acetate and washed with water. The organic layer was washed with brine, dried over anhydrous sodium sulfate, filtered and concentrated to afford 4-bromo-2-fluoro-5-methylphenol (38 g, 98% yield) as a colorless liquid. No [M+H] peak by LCMS. 1H NMR (400 MHz, CHLOROFORM-d) δ ppm 1.98 (s, 1 H) 2.22 (s, 3 H) 6.81 (dd, J=9.15, 0.54 Hz, 1 H) 7.17 (d, J=9.88 Hz, 1 H)

Step 2: 1-Bromo-5-fluoro-4-methoxy-2-methylbenzene

4-Bromo-2-fluoro-5-methylphenol (40 g, 0.19 mol), cesium carbonate (75 g, 0.23 mol), and iodomethane (15 ml, 0.23 mol) were combined in 100 ml of DMF and stirred at RT for one hour (exothermic). The solution was diluted with ethyl acetate and filtered. The solution was washed with water twice, dried with anhydrous sodium sulfate, filtered, and concentrated. The product was purified via silica gel column chromatography (RediSep 330 g column) using 0-50% ethyl acetate in hexane to afford 1-bromo-5-fluoro-4-methoxy-2-methylbenzene (38 g, 89% yield) as a colorless liquid. No [M+H] peak by LCMS. 1H NMR (400 MHz, CHLOROFORM-d) δ ppm 2.24 (s, 3 H) 3.76 (s, 3 H) 6.73 (d, J=8.80 Hz, 1 H) 7.13 (d, J=10.56 Hz, 1 H)

Step 3: 2-Bromo-4-fluoro-5-methoxybenzoic acid

Potassium permanganate (53 g, 3.4 mol) was added to a solution of 1-bromo-5-fluoro-4-methoxy-2-methylbenzene (37 g, 1.7 mol) in 75 ml of pyridine and 150 ml of water at 60° C. The solution was stirred at 60° C. degrees for 24 hours. The solution was filtered and the solids were washed with a solution of water/methanol (50:50). The filtrate was concentrated to approximately 100 ml, then acidified (pH 1) with concentrated HCl. The solid was collected by filtration and dried under vacuum to afford 2-bromo-4-fluoro-5-methoxybenzoic acid as an off white solid. MS m/z=248.9 [M+H].

Step 4: 7-Bromo-2-fluoro-3-methoxy-9H-xanthen-9-one

Sulfuric acid (41 ml, 765 mmol) was added to 2-bromo-4-fluoro-5-methoxybenzoic acid (3.75 g, 12 mmol) at RT. The reaction mixture was stirred at 60° C. for 60 min. LCMS showed complete reaction. The reaction mixture was cooled to RT and poured slowly over stirred mixture of ice and water (100 ml). The tan precipitate was filtered and washed with water (3×30 ml), twice with 30 ml of 0.5N NaOH, and with water again. The residue was recrystallized from 40 ml THF to give the title compound. MS m/z=326.2 [M+H]$^+$. Calc'd for $C_{14}H_9FBrO_3$: 325.1.

Example 10

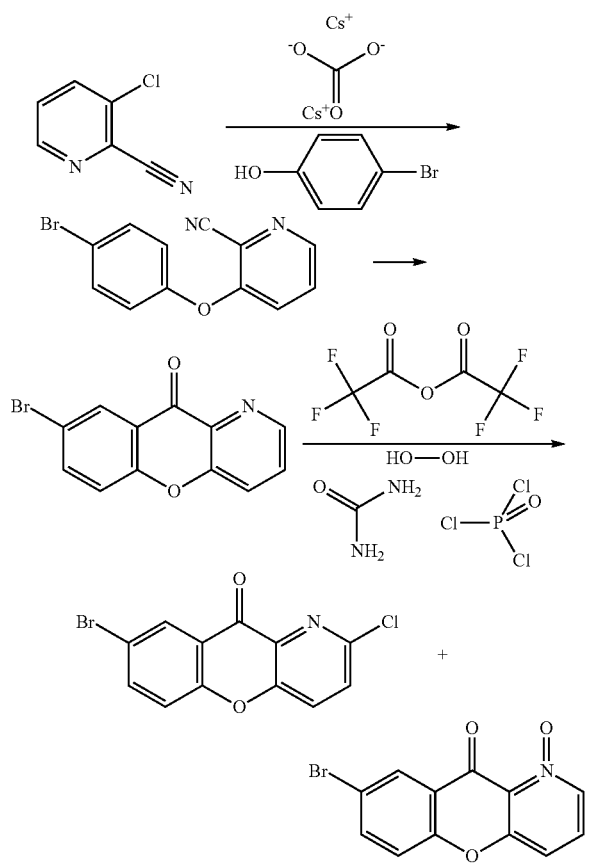

Synthesis of
8-bromo-2-chloro-10H-chromeno[3,2-b]pyridin-10-one

Step 1: A RBF was charged with 3-chloro-2-cyanopyridine (40 g, 289 mmol), 4-bromophenol (49.9 g, 289 mmol) and cesium carbonate (113 g, 346 mmol). The reactants were suspended in 50 mL of DMSO and allowed to stir at 85 C overnight. The reaction was cooled to RT and 600 mL of water was added to it. The reaction was filtered and the solid washed with water, then air dried to provide 3-(4-bromophenoxy)-picolinonitrile as a tan solid.

Step 2: A mixture of 3-(4-bromophenoxy)-picolinonitrile (57 g, 207 mmol) and 300 g of PPA was stirred at 190° C. for 2 h, followed by 180° C. overnight. After cooling to RT, the reaction mixture was poured into 500 g of ice water. After the PH was adjusted to 7 with KOH, the suspension was filtered. The solid was washed with large excess of water, followed by washing with methanol and acetone. The resulting solid was air dried to give 8-bromo-10H-chromeno[3,2-b]pyridin-10-one as a tan solid with >90% purity. The material was carried on to the next step.

Step 3: To a solution of 8-bromo-10H-chromeno[3,2-b]pyridin-10-one (60 g, 217 mmol) and urea peroxide (42.9 g, 456 mmol) in 120 mL of DCM at 0° C. was added dropwise trifluoroacetic anhydride (63.9 mL, 456 mmol). The resulting reaction was stirred for 2 h. The reaction was quenched with 10% $Na_2S_2O_3$, extracted with DCM, dried over $Na_2SO_4$ and evaporated to dryness to give crude 8-bromo-10-oxo-10H-chromeno[3,2-b]pyridine 1-oxide as a pale yellow solid.

Step 4: To a suspension of 8-bromo-10-oxo-10H-chromeno[3,2-b]pyridine 1-oxide in 100 mL of toluene at 0° C. was added dropwise phosphorus oxychloride (35.8 mL, 391 mmol) followed by 2 mL of DMF and the mixture was stiffed at RT overnight. The solvent was evaporated under vacuum and the residue which crashed out of water, was filtered and washed with water, methanol and acetone in sequence. The solid was air dried to give 8-bromo-2-chloro-10H-chromeno[3,2-b]pyridin-10-one as a tan solid.

Example 11

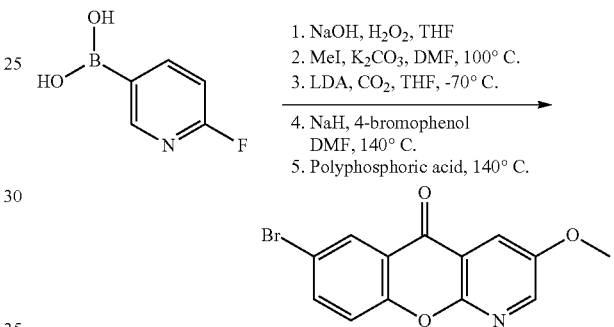

Synthesis of
7-Bromo-3-methoxy-5H-chromeno[2,3-b]pyridin-5-one

Step 1: A three neck 3-L RBF equipped with an overhead stiffed was charged with 6-fluoropyridin-3-ylboronic acid (105 g, 745 mmol) and 1 L of THF. The mixture was cooled to 0° C. and NaOH 6N (373 mL, 2235 mmol) was added. To the resulting mixture was added hydrogen peroxide 30% (126 mL, 4098 mmol), dropwise via an addition funnel over the course of 30 minutes. After stirring at 0° C. for 2 hours the mixture was removed from the ice bath and maintained at RT for 30 minutes. The reaction was acidified to pH 7 with 6 N HCl (ca. 300 mL) and diluted with 500 mL of ether. The aqueous layer was extracted with ether (2×1 L) and the combined organic layers were washed with water (1.5 L) then brine before being dried over sodium sulfate. Filtration and concentration provided a white solid that was dried on high vac overnight to provide 6-fluoropyridin-3-ol.

Step 2: To a solution of 6-fluoropyridin-3-ol (75 g, 663 mmol) in DMF (265 mL, 663 mmol) were added potassium carbonate (59.7 g, 995 mmol) and iodomethane (108 g, 763 mmol). The resulting slurry was heated at 100° C. for 3 hours. The reaction was diluted with water (1000 mL) and poured into a separatory funnel containing diethyl ether (1000 mL). The layers were separated and the aqueous layer was extracted with diethyl ether (4×500 mL). The combined organic layers were washed with water and then brine, dried over sodium sulfate, filtered and concentrated in vacuo to provide a yellow oil. This oil was diluted with 500 mL of DCM and concentrated to provide a yellow oil with a large amount of an off white precipitate. The mixture was filtered and the derived solid was washed well with DCM. The filtrate was concentrate to provide a mixture consisting of a yellow oil and an off white solid. The solid was filtered, washing with DCM. Repeat this procedure again and then concentrated the filtrate to provide a yellow oil. The oil was taken up in 100 mL of ether and flashed through a plug of silica gel with 10:1 hexanes:ether to provide 2-fluoro-5-methoxypyridine as a yellow oil.

Step 3: To a solution of DIPA (54.0 mL, 385 mmol) in THF (1101 mL, 385 mmol) at −60° C. was added BuLi, 2.5 M in hexanes (154 mL, 385 mmol) over 5 minutes such that the internal temperature was maintained below −60° C. After stirring for 45 minutes at −65° C. a solution of 2-fluoro-5-methoxypyridine (49 g, 385 mmol) in 200 mL of THF was added over the course of 2 minutes maintaining an internal temperature <−65° C. The reaction was stirred at −70° C. for 1.5 hours then reaction was poured into a 3 L flask containing 1200 g of crushed dry ice. The reaction was allowed to warm to 0° C. and then poured into 1000 mL of water. The organics were removed under reduced pressure and the aqueous layer was acidified with 1100 mL of 2 N HCl. The resulting thick white slurry was stirred for 1 hour then filtered to provide 2-fluoro-5-methoxynicotinic acid as a white solid.

Step 4: To a slurry of sodium hydride (60% dispersion) (21.74 g, 543 mmol) in DMF (351 mL, 175 mmol) at 0° C. was added 4-bromophenol (60.7 g, 351 mmol) over the course of 5 minutes. Stirred at 0° C. for two minutes then removed from the ice bath and stirred for an additional 5 minutes at room temperature. Added 2-fluoro-5-methoxynicotinic acid (30 g, 175 mmol) portionwise over 10 minutes and heated the resulting slurry at 140° C. After cooling to RT the mixture was then poured onto 1 kg of ice and was quenched with acetic acid (50.2 mL, 877 mmol) and then 75 mL of 6 N HCl. Stirred vigorously for 1 hour, leading to the formation of a red slurry containing a very fine white precipitate. The slurry was filtered to provide 2-(4-bromophenoxy)-5-methoxynicotinic acid.

Step 5: A 2 L RBF charged with polyphosphoric acid (115% H$_3$PO$_4$) (300 g, 89 mmol) was heated to 140° C. at which point 2-(4-bromophenoxy)-5-methoxynicotinic acid (29 g, 89 mmol) was introduced. The thick viscous mixture is slowly stirred while heating at 140° C. After heating for 2.5 hours the solution was cooled to 100° C. and then poured onto 1 kg of ice, leading to the formation of a yellow taffy mixture. The slurry was vigorously stirred for 1 hour leading to the formation of a fine white precipitate. Filtration of this mixture proceeded slowly to provide an off white solid. This solid was washed well with DCM. The filtrate, which contained the desired product, was washed with brine and concentrated to provide 7-bromo-3-methoxy-5H-chromeno[2,3-b]pyridin-5-one as an off-white solid.

Example 12

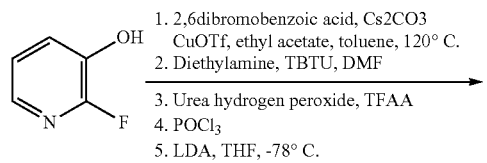

1. 2,6dibromobenzoic acid, Cs2CO3 CuOTf, ethyl acetate, toluene, 120° C.
2. Diethylamine, TBTU, DMF
3. Urea hydrogen peroxide, TFAA
4. POCl$_3$
5. LDA, THF, -78° C.

-continued

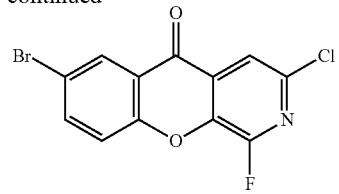

Synthesis of 7-Bromo-3-chloro-1-fluoro-5H-chromeno[2,3-c]pyridin-5-one

Step 1: A 500 mL RBF was charged with 2-fluoro-3-hydroxypyridine (3487 mg, 30.8 mmol), 2,5-dibromobenzoic acid (8630 mg, 30.8 mmol), copper (I) trifluoromethanesulfonate toluene complex (2:1) (399 mg, 0.771 mmol) and cesium carbonate (2.01E+04 mg, 61.7 mmol). To this was added 100 mL of toluene and the mixture was azeotroped to remove about 20 mL of toluene under reduced pressure. Reaction mixture was then flushed with N2 and was heated to 120° C. for 2 hours. LC-MS analysis showed formation of the desired product along with significant impurities. The reaction mixture was cooled to RT and concentrated to give a gummy residue. The residue was taken up in ethyl acetate (100 mL) and water (75 mL). The aqueous layer was neutralized with 1N HCl to pH ~2.0-3.0. The aqueous layer was extracted with ethyl acetate (2×150 mL), separated, dried over anhydrous sodium sulfate, and concentrated to yield the crude product as a brown solid which was used directly in the next step.

Step 2: A mixture of crude 5-bromo-2-(2-fluoropyridin-3-yloxy)benzoic acid (8.00 g, 25.6 mmol), diethylamine (6.63 mL, 64.1 mmol) and TBTU (8.23 g, 25.6 mmol) in 8 mL of DMF was stirred overnight. The reaction was quenched with Sat. NaHCO3, extracted with EA/H=2:1, washed with brine, dried over Na2 SO4, filtered and evaporated to dryness. CC (DCM to DCM/EA 100:5 to 100:10 to 100:20 to 3:1) gave 5-bromo-N,N-diethyl-2-(2-fluoropyridin-3-yloxy)benzamide as a yellow solid.

Step 3: To a solution of 5-bromo-N,N-diethyl-2-(2-fluoropyridin-3-yloxy)benzamide (1.4 g, 3.81 mmol) and urea peroxide (1.076 g, 11.44 mmol) in 10 mL of DCM at 0 C was added dropwise trifluoroacetic anhydride (1.601 mL, 11.44 mmol) and the resulting reaction was stirred overnight. LCMS showed only less than 50% of desired conversion. The mixture was evaporated to dryness, quenched with Sat. NaHCO$_3$, extracted with EA, dried over Na$_2$SO$_4$, filtered and evaporated to dryness. CC (DCM to DCM/EA=3:1 to DCM/MeOH=100:2 to 100:5 to 100:10) gave 3-(4-bromo-2-(diethylcarbamoyl)phenoxy)-2-fluoropyridine 1-oxide as an off-white solid.

Step 4: To a solution of 3-(4-bromo-2-(diethylcarbamoyl)phenoxy)-2-fluoropyridine 1-oxide (420 mg, 1.096 mmol) in 15 mL of DCM was added dropwise phosphorus oxychloride (301 μL, 3.29 mmol) followed by 2 drops of DMF. After stirring at rt for 1 h, the reaction was quenched with sat. NaHCO$_3$, extracted into EtOAc, dried over Na$_2$SO$_4$, filtered and concentrated under reduced pressure. The crude was purified by column chromatography (DCM to DCM/EtOAc gradient beginning from 10:1 to 5:1 to 3:1) gave 5-bromo-2-(6-chloro-2-fluoropyridin-3-yloxy)-N,N-diethylbenzamide as a colorless gum.

Step 5: To a solution of 5-bromo-2-(6-chloro-2-fluoropyridin-3-yloxy)-N,N-diethylbenzamide (120 mg, 0.299 mmol) in 5 mL of dry THF at 78° C. was added dropwise lithium diisopropylamide, 2.0 m heptane/tetrahydrofuran/ ethylbenzene (158 μL, 1.195 mmol) (0.6 mL of 2M solution) and the reaction was stirred at −78° C. for 3 h. The reaction was quenched at −78° C. with sat. NH₄Cl and was allowed to warm up to RT. The reaction was extracted with ETOAc, dried over Na₂SO₄, filtered and evaporated to dryness. The crude was purified by column chromatography (1:1 hexane/DCM to 100% DCM) to give the titled compound, 7-bromo-3-chloro-1-fluoro-5H-chromeno[2,3-c]pyridin-5-one, as an offwhite solid. MS (M+1): 328.

The following compounds in Table I are additional representative examples of compounds of Formulas I, II, III and IV, and sub-formulas thereof, provided by the present invention. The methods used to prepare the exemplary compounds are included in Table 1, and correspond to those described in the Examples 1-7 herein above. The methods used to prepare the exemplary compounds 11-28 shown in Table 1 are as described in the Example No. ("Eg") so indicated and herein above. Table I further provides the mass and biological data (average nM IC₅₀'s for the enzyme and cell assays, provided) for each compound, where available.

TABLE I

| Example | Compound Structure | Compound Name | Observed MW | Method | BACE 1 FRET assay (uM) | HEK cell assay (uM) |
|---|---|---|---|---|---|---|
| 2 | 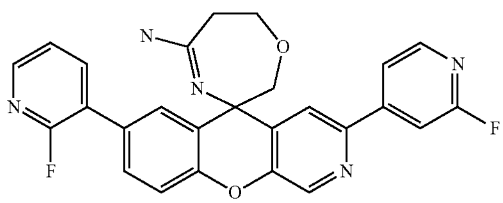 [SMILES: NC1=NC2(COCC1)c1cc(-c3cccnc3F)ccc1Oc1cnc(-c3ccnc(F)c3)cc12] | (5R/S)-7-(2-fluoro-3-pyridinyl)-3-(2-fluoro-4-pyridinyl)-6',7'-dihydrospiro-[chromeno-[2,3-c]pyridine-5,3'-[1,4]oxazepin]-5'-amine | 472 | 1 | 0.001 | 0.003 |
| 13 | 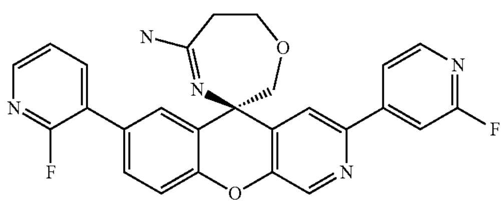 [SMILES: NC1=N[C@]2(COCC1)c1cc(-c3cccnc3F)ccc1Oc1cnc(-c3ccnc(F)c3)cc12] | (5R)-7-(2-fluoro-3-pyridinyl)-3-(2-fluoro-4-pyridinyl)-6',7'-dihydrospiro[chromeno-[2,3-c]-pyridine-5,3'-[1,4]oxazepin]-5'-amine | 472 | 1 | 0.139 | 0.078 |
| 14 | 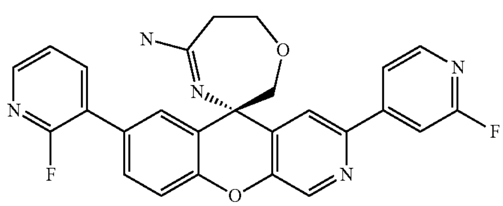 [SMILES: NC1=N[C@@]2(COCC1)c1cc(-c3cccnc3F)ccc1Oc1cnc(-c3ccnc(F)c3)cc12] | (5S)-7-(2-fluoro-3-pyridinyl)-3-(2-fluoro-4-pyridinyl)-6',7'-dihydrospiro[chromeno-[2,3-c]-pyridine-5,3'-[1,4]oxazepin]-5'-amine | 472 | 1 | 0.0005 | 0.001 |
| 3B | 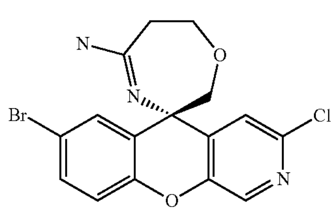 [SMILES: NC1=N[C@@]2(COCC1)c1cc(Br)ccc1Oc1cnc(Cl)cc12] | (5S)-7-bromo-3-chloro-6',7'-dihydrospiro-[chromeno[2,3-c]-pyridine-5,3'-[1,4]oxazepin]-5'-amine | 394 | | 3.826 | 0.892 |
| 3A | 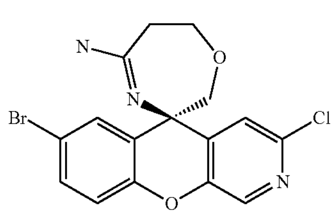 [SMILES: NC1=N[C@]2(COCC1)c1cc(Br)ccc1Oc1cnc(Cl)cc12] | (5R)-7-bromo-3-chloro-6',7'-dihydrospiro-[chromeno[2,3-c]pyridine-5,3'-[1,4]oxazepin]-5'-amine | 394 | | 9.228 | 6.374 |

TABLE I-continued

| Example | Compound Structure | Compound Name | Observed MW | Method | BACE 1 FRET assay (uM) | HEK cell assay (uM) |
|---------|-------------------|---------------|-------------|--------|------------------------|---------------------|
| 4 | 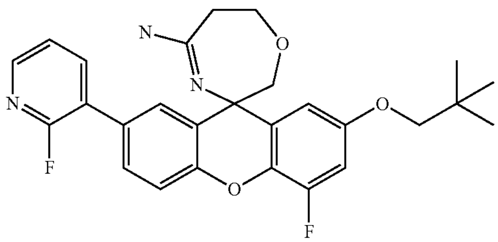 [SMILES: CC(C)(C)COc1cc(F)c2c(c1)C1(COCCC(N)=N1)c1cc(-c3cccnc3F)ccc1O2] | (3R/S)-2'-(2,2-dimethylpropoxy)-4'-fluoro-7'-(2-fluoro-3-pyridinyl)-6,7-dihydrospiro[1,4-oxazepine-3,9'-xanthen]-5-amine | 480 | 2 | 0.001 | 0.012 |
| 15 | 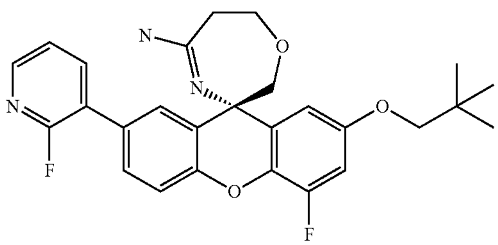 [SMILES: CC(C)(C)COc1cc(F)c2c(c1)[C@]1(COCCC(N)=N1)c1cc(-c3cccnc3F)ccc1O2] | (3S)-2'-(2,2-dimethylpropoxy)-4'-fluoro-7'-(2-fluoro-3-pyridinyl)-6,7-dihydrospiro[1,4-oxazepine-3,9'-xanthen]-5-amine | 480 | 2 | 0.0005 | 0.007 |
| 16 | 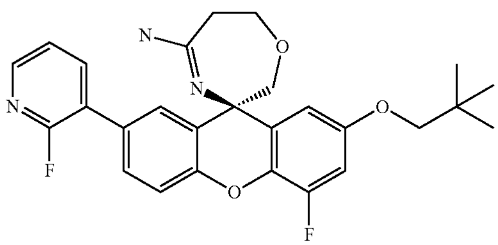 [SMILES: CC(C)(C)COc1cc(F)c2c(c1)[C@@]1(COCCC(N)=N1)c1cc(-c3cccnc3F)ccc1O2] | (3R)-2'-(2,2-dimethylpropoxy)-4'-fluoro-7'-(2-fluoro-3-pyridinyl)-6,7-dihydrospiro[1,4-oxazepine-3,9'-xanthen]-5-amine | 480 | 2 | 0.285 | 0.300 |
| 17 | 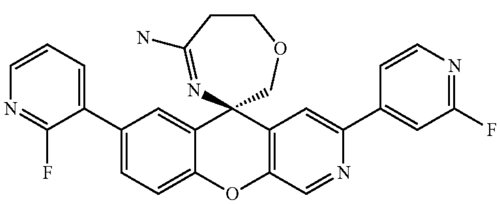 [SMILES: NC1=N[C@]2(COCC1)c1cc(-c3cccnc3F)ccc1Oc1cnc(-c3ccnc(F)c3)cc12] | (5R)-7-(2-fluoro-3-pyridinyl)-3-(2-fluoro-4-pyridinyl)-6',7'-dihydro-2'H-spiro[chromeno[2,3-c]pyridine-5,5'-[1,4]oxazepin]-3'-amine | 472 | 1 | 0.369 | 0.689 |
| 18 | 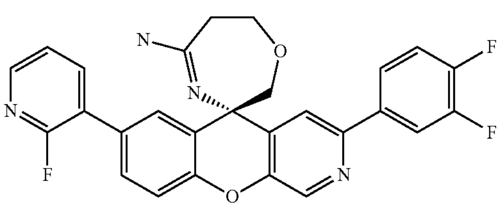 [SMILES: NC1=N[C@@]2(COCC1)c1cc(-c3cccnc3F)ccc1Oc1cnc(-c3ccc(F)c(F)c3)cc12] | (S)-3-(3,4-difluorophenyl)-7-(2-fluoropyridin-3-yl)-6',7'-dihydro-2'H-spiro[chromeno[2,3-c]pyridine-5,5'-[1,4]oxazepin]-3'-amine | 489 | 1 | 0.002 | 0.019 |
| 19 | 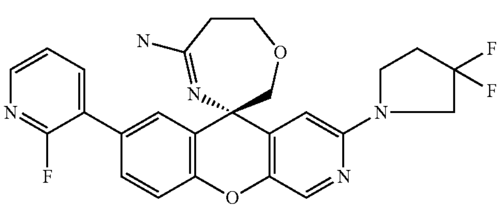 [SMILES: NC1=N[C@@]2(COCC1)c1cc(-c3cccnc3F)ccc1Oc1cnc(N3CCC(F)(F)C3)cc12] | (S)-3-(3,3-difluoropyrrolidin-1-yl)-7-(2-fluoropyridin-3-yl)-6',7'-dihydro-2'H-spiro[chromeno[2,3-c]pyridine-5,5'-[1,4]oxazepin]-3'-amine | 482 | 3 | 0.003 | 0.004 |

The following compounds in Table 2 are additional representative examples of Formulas I-IV provided by the present invention.

TABLE 2

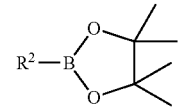

| Ex. No. | R² | A³ | A⁴ | R⁷ | X | Y |
|---|---|---|---|---|---|---|
| 20 | 3,6-dihydro-2H-pyran-3-yl | CH | N | 2-Fluoropyridin-3-yl | CH₂ | —O— |
| 21 | 2,2-dimethylpropanenitrile-oxyl | CH | N | 2-Fluoropyridin-3-yl | CH₂ | —O— |
| 22 | 3-methyl-e-oxetane-methoxyl | CH | CH | 2-Fluoropyridin-3-yl | —O— | CH₂ |
| 23 | 3-methyl-1H-pyrazolyl- | CH | CH | 2-Fluoropyridin-3-yl- | —O— | CH₂ |
| 24 | 3,6-dihydro-2H-pyran-4-yl | CH | N | 2-Fluoropyridin-3-yl | —O— | CH₂ |
| 25 | 2-F-pyrrolidin-1-yl | CH | N | 2-Fluoropyridin-3-yl | —O— | CH₂ |
| 26 | 3,6-dihydro-2H-pyran-4-yl | CH | N | 2-Fluoropyridin-3-yl | CH₂ | —O— |
| 27 | 2,3-dimethyl-3,6-dihydro-2H-pyran-4-yl | CF | N | 2-Fluoropyridin-3-yl | CH₂ | —O— |
| 28 | 3-methyl-3-oxetanyl-ethynyl | CF | N | 2-Fluoropyridin-3-yl | —O— | CH₂ |
| 29 | 3,6-dihydro-2H-pyran-3-yl | CF | N | 2-Fluoropyridin-3-yl | —O— | CH₂ |
| 30 | 2,2-dimethylpropanenitrile-oxyl | CF | N | 2-Fluoropyridin-3-yl | CH₂ | —O— |
| 31 | 3-methyl-e-oxetane-methoxyl | CF | N | 2-Fluoropyridin-3-yl | CH₂ | —O— |
| 32 | 3-methyl-1H-pyrazolyl- | CF | N | 2-Fluoropyridin-3-yl | —O— | CH₂ |
| 33 | 3,6-dihydro-2H-pyran-4-yl | CF | N | 2-Fluoropyridin-3-yl | —O— | CH₂ |
| 34 | 2-F-pyrrolidin-1-yl | CF | N | 2-Fluoropyridin-3-yl | CH₂ | —O— |
| 35 | 3,6-dihydro-2H-pyran-4-yl | CF | N | pyridin-3-yl | CH₂ | —O— |
| 36 | 2,3-dimethyl-3,6-dihydro-2H-pyran-4-yl | CF | N | 2-Fluoropyridin-3-yl | —O— | CH₂ |
| 37 | 3-methyl-3-oxetanyl-ethynyl | CF | N | 2-Fluoropyridin-3-yl | —O— | CH₂ |
| 38 | 3,6-dihydro-2H-pyran-3-yl | CF | N | 2-Fluoropyridin-3-yl | CH₂ | —O— |
| 39 | 2,2-dimethylpropanenitrile-oxyl | CF | N | 2-Fluoropyridin-3-yl | CH₂ | —O— |

The present invention also provides methods for making compounds of Formulas I-IV, and sub-formulas therein. For example, the compounds in Table 2 and additional examples may be made by the following methods, as similarly described in the literature references mentioned below.

In one embodiment of the invention, there is provided a method of making a compound of Formula I, the method comprising the step of reacting a compound 20

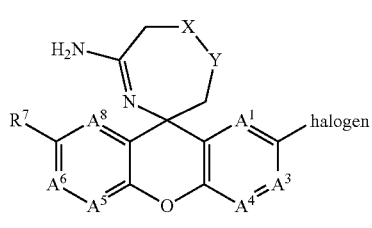

wherein $A^1$, $A^3$, $A^4$, $A^5$, $A^6$, $A^8$, $R^7$, X and Y of Formula I are as defined herein and halogen is either a bromine (Br) or chlorine (Cl), with a compound having the structure $$R^2\text{—}B\begin{array}{c}O\\|\\O\end{array}\hspace{-0.5em}\begin{array}{c}\end{array}$$

or $R^2$—$B(OH)_2$, wherein $R^2$ is as defined herein, to make a compound of Formula I.

In another embodiment of the invention, there is provided a method of making a compound of Formula I-A, the method comprising the step of reacting a compound 20

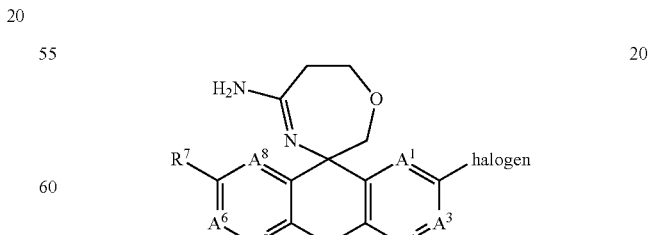

wherein $A^1$, $A^3$, $A^4$, $A^5$, $A^8$, $R^7$ and $R^9$ of Formula I-A are as defined herein and halogen is either a bromine (Br) or chlorine (Cl), with a compound having the structure

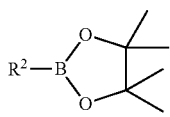

or R²—B(OH)₂, wherein R² is as defined herein, to make a compound of Formula I-A.

In another embodiment of the invention, there is provided a method of making a compound of Formula I-B, the method comprising the step of reacting a compound 20

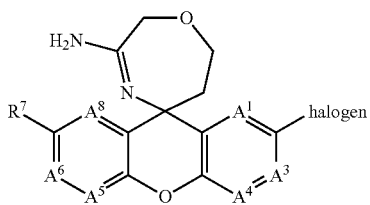

wherein A¹, A³, A⁴, R⁷, W, X, Y and Z of Formula I-B are as defined herein and halogen is either a bromine (Br) or chlorine (Cl), with a compound having the structure

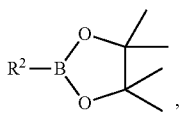

R²—B(OH)₂ or wherein R² is as defined herein, to make a compound of Formula I-B.

In another embodiment of the invention, there is provided a method of making a compound of Formula II, the method comprising the step of reacting a compound 20

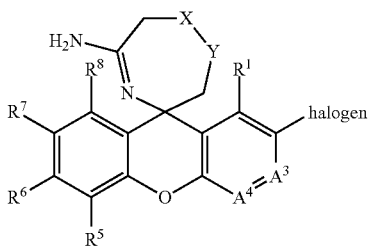

wherein A³, A⁴, R¹, R⁵, R⁶, R⁷, R⁸, X and Y of Formula II are as defined herein and halogen is either a bromine (Br) or chlorine (Cl), with a compound having the structure

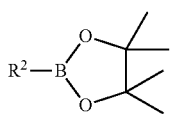

or R²—B(OH)₂, wherein R² is as defined herein, to make a compound of Formula II.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2$^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group, such as the basic amine group(s) in compounds of the invention herein, may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H+ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I-IV, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$ (deuterium), $^3H$ (tritium), $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Deuterated ($^2H$), Tritiated ($^3H$) and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

BIOLOGICAL EVALUATION

The compounds of the invention may be modified by appending appropriate functionalities to enhance selective biological properties. The pharmacokinetic and pharmacodynamic properties of a compound relate, directly and indirectly, to the ability of the compound to be effective for its intended use.

Although the pharmacological properties of the compounds of the invention (Formulas I-IV) vary with structural change, in general, activity possessed by compounds of Formulas I-IV may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE FRET (Fluorescence Resonance Energy Transfer) Assay

The assay buffer used in this screen is 0.05 M acetate, pH 4.2, 10% DMSO final, 100 uM genapol (which is a nonionic detergent, below its Critical Micelle Concentration). The Beta Secretase enzyme (0.2 nM) is pre-incubated for one hour with inhibitors, typically in about 1 uL of DMSO according to a serial dilution, are added thereto. This assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm). Where available, the in-vitro BACE FRET enzyme data for each of the Examples is provided in Table I.

In Vitro BACE Cell-Based Assay

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ40 levels were determined using a sandwich ELISA. The $IC_{50}$ of the compound was calculated from the percent of control or percent inhibition of Aβ40 as a function of the concentration of the test compound.

The sandwich ELISA to detect Aβ40 was performed in 96 well microtiter plates, which were pre-treated with goat anti-rabbit IgG (Pierce). The capture and detecting antibody pair that were used to detect Aβ40 from cell supernatants were affinity purified pAb40 (Biosource) and biotinylated 6E10 (Signet Labs Inc.), respectively. The optimal concentration for the pAb40 antibody was 3 μg/ml in Superblock/TBS (Pierce) that was supplemented with 0.05% Tween 20 (Sigma). Optimal concentration for the detection antibody 6E10-biotinylated was 0.5 μg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer). Where available, the in-vitro BACE cell based data for each of the Examples is provided in Table I.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, *Journal of Neurochemistry,* 76, 173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics,* 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of A-beta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, amyloid beta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2
 IV: 5% EtOH, 45% Propylene glycol in 5% Dextrose The compounds of the invention may be shown to reduce the formation and/or deposition of amyloid beta peptide in the cerebrospinal fluid (CSF) as well as in the brain of a mouse or rat at both 10 mpk (mpk=mg compound per kg animal) and 30 mpk dosing concentrations after 4 hrs.

Indications

De Meyer et al re-affirm the believed role which the accumulation of beta-amyloid protein (A-beta) in cerebral spinal fluid (CSF) in a subject plays in the progression of symptoms, initially revealed as mild cognitive impairment, which ultimately leads to AD. *Arch Neurol.* 67(8):949-956, 2010. Amyloid-b (Ab) peptides generated from amyloid precursor protein (APP) by proteolytic cleavage, such as by aspartyl protease enzymes including beta-secreatase (BACE) and gamma-secretase, likely play a causal role in AD pathogenesis (Tanzi and Bertram, *Cell.* (120): 545-555, 2005; Walsh and Selkoe, *Neuron*, (44): 181-193, 2004). Although the precise mechanisms of Ab toxicity are unclear, oligomeric forms of Ab may contribute to cognitive decline by altering synaptic structure and function (Palop and Mucke, *Nat. Neuroscience*, (13): 812-818, 2010; Selkoe, *Behavioral Brain Res.*, (192): 106-113, 2008; Shankar et al., *Nat. Medicine* (14): 837-842, 2008). Transgenic mouse models that overexpress mutant APP and produce high levels of Ab show amyloid plaque deposition, synaptic deficits, learning and memory impairments, and other behavioral abnormalities (Games et al., *Nature*, (373): 523-527, 1995; Gotz et al., *Molecular Psychiatry* (9): 664-683, 2004; Hsia et al., *Proc. Natl. Academy of Science* USA (96): 3228-3233, 1999; Hsiao et al., *Science* (274): 99-102, 1996, citing Harris et al, *Neuron* (68): 428-441, 2010).

The compounds of the invention have been shown to modulate, and specifically inhibit the activity of the beta-secretase enzyme, thereby reducing the A-beta peptide fragments believed to be responsible for Alzheimer's Disease (AD). Bapineuzamab, a monoclonal amino-terminus specific anti-amyloid antibody is presently in Phase III clinical trials for the treatment of AD. *Alzheimer's Research & Therapy*, 1:2, 2009. Each of the known genetic causes of AD is linked to A-beta. Dementia, Down's Syndrome to APP over-production, are all believed to be linked to the deposition of A-beta on the brain. With methods for identifying brain amyloid deposition, positron emission scanning (PET) and CSF measurements of Ab42, identification of AD suffering individuals needing treatment is becoming easier amd more common. It is firmly believed that by reducing the formation of A-beta, one can begin to pre-treat AD. Vassar et al, *Journal of Neuroscience*, 29 (41):12787-12794, 2009. One published pathway for treatment of AD is inhibition of beta-secretase. Tirrell, *Bloomberg News, The Boston Globe*. Jan. 7, 2010.

The US biotech company CoMentis is developing an orally bioavailable small molecule CTS-21166, a highly potent, highly selective and efficacious brain-penetrating beta-secretase inhibitor. CoMentis successfully completed a Phase I study of CTS-21166 in healthy volunteers in 2008. Results indicated that CTS-21166 was safe, well-tolerated and pharmacodynamically active at all dose levels. All clinical subjects administered CTS-21166 showed area-under-curve (AUC) reduction in plasma A-Beta40 reductions ranging from 40-75%. Because of the urgent need for AD treatment, Phase II studies for CTS-2166 are planned, or ongoing, for AD patients. In preclinical studies, CTS-21166 exhibits excellent efficacy, selectivity, brain penetration and pharmacologic activity.

Accordingly, compounds of the invention, i.e., compounds of Formulas I, II, III and IV, are useful for, but not limited to, the prevention or treatment of beta-secretase related diseases, including Alzheimer's disease. The compounds of the invention have the ability to modulate the activity of beta secretase enzyme, thereby regulating the production of amyloid beta (Abeta peptide) and reducing the formation and deposition of Abeta peptide in both the cerebral spinal fluid as well as in the brain, resulting in a decrease of amyloid plaque on the brain. In one embodiment of the invention, there is provided a method of treating a disorder related to a beta-secretase enzyme in a subject, the method comprising administering to the subject an effective dosage amount of a compound of Formulas I, II, III, IV, and sub-formulae thereof. In another embodiment, there is provided a method of reducing production of amyloid beta, and of reducing plaque formation on the brain. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I-IV. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Accordingly, the compounds of the invention would be useful in therapy as CNS agents in treating neurological disorders and related conditions in subjects.

Besides being useful for human treatment, the compounds of the invention may be useful for veterinary treatment of companion animals, exotic animals and farm animals, including mammals, rodents, and the like. For example, animals including horses, dogs, and cats may be treated with compounds provided herein.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an "effective amount" of a compound of the invention or an "effective dosage amount" of a compound of the invention. An "effective dosage amount" of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I-IV with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I-IV with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I, II and III may also be administered sequentially with other known medicinal agents. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula I

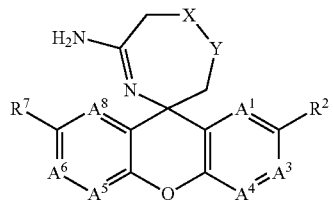

I or a stereoisomer, tautomer, hydrate, solvate or pharmaceutically acceptable salt thereof, wherein $A^1$ is $CR^1$ or N;
$A^3$ is $CR^3$ or N;
$A^4$ is $CR^4$ or N;
$A^5$ is $CR^5$ or N;
$A^6$ is $CR^6$ or N;
$A^8$ is $CR^8$ or N, provided that no more than one of $A^1$, $A^3$, $A^4$, $A^5$, $A^6$ and $A^8$ is N;
each of $R^9$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$NHC_{1-6}$-alkyl and —$C(O)C_{1-6}$-alkyl are optionally substituted with 1-3 substituents of F, oxo or OH;
$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;
each of $R^3$ and $R^6$, independently, is H, halo, haloalkyl, haloalkoxyl, $C_{1-6}$-alkyl, CN, OH, $OC_{1-6}$-alkyl, $NHC_{1-6}$-alkyl or $C(O)C_{1-6}$-alkyl;
$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NHC(=O)$R^9$, —C(=O)NH$R^9$, —NHS(O)$_2R^9$, —S(O)$_2$NH$R^9$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;
each $R^9$, independently, is halo, haloalkyl, CN, OH, $NO_2$, $NH_2$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl; and
—X—Y— is —$CR^{10}R^{10}$—O—, —O—$CR^{10}R^{10}$—, —$CR^{10}R^{10}$—S— or —S—$CR^{10}R^{10}$, wherein each $R^{10}$, independently, is H or F.

2. The compound of claim 1, or a stereoisomer or pharmaceutically acceptable salt thereof, wherein each of $R^1$, $R^4$, $R^5$ and $R^8$, independently, is H, F, Cl, $CF_3$, $OCF_3$, methyl, ethyl, CN, OH, $OCH_3$, $NHCH_3$ or $C(O)CH_3$;

one of $R^2$ and $R^7$, independently, is $C_{2-4}$alkynyl, $-OC_{1-6}$alkyl, $-SC_{1-6}$alkyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, or cyclohexyl, wherein the $C_{2-4}$alkynyl, $-OC_{1-6}$alkyl, $-SC_{1-6}$alkyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

the other of $R^2$ and $R^7$, independently, is phenyl, pyridyl, pyrimidyl, pyrazinyl or pyridazinyl, wherein the phenyl, pyridyl, pyrimidyl, pyrazinyl and pyridazinyl are optionally substituted, independently, with 1-3 substituents of $R^9$; and each of $R^3$ and $R^6$, independently, is H, halo, haloalkyl, haloalkoxyl, $C_{1-6}$-alkyl, CN, OH, $OC_{1-6}$-alkyl, $NHC_{1-6}$-alkyl or $C(O)C_{1-6}$-alkyl.

3. The compound of claim 1, or a stereoisomer or pharmaceutically acceptable salt thereof, wherein $R^2$ is Cl, Br, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza[3,5]-spironon-7-yl, cyclopentyl or cyclohexyl, wherein the $C_{1-6}$-alkyl, $C_{2-4}$alkenyl, $C_{2-4}$alkynyl and ring are optionally substituted, independently, with 1-3 substituents of $R^9$;

each of $R^1$, $R^4$, $R^5$ and $R^8$, independently, is H, F, methyl, CN or OH;

each of $R^3$ and $R^6$, independently, is H, F, Cl, $CF_3$, methyl, CN, OH, $OCH_3$ or $NHCH_3$;

$R^7$ is a ring selected from phenyl, pyridyl, pyrimidyl, pyridazinyl, pyrazinyl, or thienyl, said ring optionally substituted, independently, with 1-3 substituents of $R^9$; and —X—Y— is $-CH_2-O-$, $-O-CH_2-$, $-CH_2-S-$ or $-S-CH_2-$.

4. A compound of claim 1 having a Formula II:

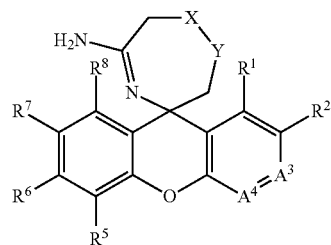

II or a stereoisomer, tautomer, hydrate, solvate or pharmaceutically acceptable salt thereof, wherein $A^3$ is $CR^3$ or N;

$A^4$ is $CR^4$ or N, provided that no more than one of $A^3$ and $A^4$ is N;

each of $R^1$, $R^4$, $R^5$ and $R^8$, independently, is H, F, Cl, Br, $CF_3$, $OCF_3$, $C_{1-6}$-alkyl, CN, OH, $-OC_{1-6}$-alkyl, $-NHC_{1-6}$-alkyl or $-C(O)C_{1-6}$-alkyl, wherein the $C_{1-6}$-alkyl and $C_{1-6}$-alkyl portion of $-OC_{1-6}$-alkyl, $-NHC_{1-6}$-alkyl and $-C(O)C_{1-6}$-alkyl are optionally substituted with 1-3 substituents of F, oxo or OH;

$R^2$ is Cl, Br, $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or $-Si(CH_3)_3$, wherein the $C_{1-6}$-alkyl, $C_{2-4}$alkenyl, $C_{2-4}$alkynyl, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $NHC_{1-6}$-alkyl or $C(O)C_{1-6}$-alkyl;

$R^7$ is $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-NHC(=O)R^9$, $-C(=O)NHR^9$, $-NHS(O)_2R^9$, $-S(O)_2NHR^9$, $-NH$-phenyl, $-NH$-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, $-OC_{1-6}$alkyl, $-SC_{1-6}$alkyl, $-NHC_{1-6}$alkyl, $-N(C_{1-3}$alkyl$)_2$, $-NH$-phenyl, $-NH$-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-5 substituents of $R^9$;

each $R^9$, independently, is halo, haloalkyl, CN, OH, $NO_2$, $NH_2$, acetyl, $-C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, phenyl, pyridyl, pyrimidyl, pyrazinyl, pyridazinyl, pyrazolyl, isoxazolyl, thiazolyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl; and —X—Y— is —$CR^{10}R^{10}$—O—, —O—$CR^{10}R^{10}$—, —$CR^{10}R^{10}$—S— or —S—$CR^{10}R^{10}$, wherein each $R^{10}$, independently, is H or F.

5. The compound of claim 1 or a stereoisomer, tautomer or pharmaceutically acceptable salt thereof, wherein
$R^1$ is H or F;
$A^3$ is CH, CF or N;
$A^4$ is CH, CF or N;
$R^5$ is H or F;
$A^6$ is CH, CF or N;
$R^8$ is H or F; and
—X—Y— is —$CH_2$—O— or —O—$CH_2$—.

6. The compound of claim 1 or a stereoisomer or pharmaceutically acceptable salt thereof, wherein
each of $R^1$, $R^4$, $R^5$ and $R^8$, independently, is H, F, Cl, $CF_3$, $OCF_3$, methyl, ethyl, CN, OH, $OCH_3$, $NHCH_3$ or C(O)$CH_3$;
one of $R^2$ and $R^7$, independently, is $C_{2-4}$alkynyl, —$OC_{1-6}$alkyl, —$SC_{1-6}$alkyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, or cyclohexyl, wherein the $C_{2-4}$alkynyl, —$OC_{1-6}$alkyl, —$SC_{1-6}$alkyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, thienyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;
the other of $R^2$ and $R^7$, independently, is phenyl, pyridyl, pyrimidyl, pyrazinyl or pyridazinyl, wherein the phenyl, pyridyl, pyrimidyl, pyrazinyl and pyridazinyl are optionally substituted, independently, with 1-3 substituents of $R^9$;
each of $R^3$ and $R^6$, independently, is H, halo, haloalkyl, haloalkoxyl, $C_{1-6}$-alkyl, CN, OH, $OC_{1-6}$-alkyl, $NHC_{1-6}$-alkyl or $C(O)C_{1-6}$-alkyl; and
—X—Y— is —$CH_2$—O— or —O—$CH_2$—.

7. The compound of claim 1 or a stereoisomer or pharmaceutically acceptable salt thereof, wherein $R^7$ is a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, piperidinyl, piperazinyl, morpholinyl, said ring optionally substituted, independently, with 1-3 substituents of $R^9$.

8. The compound of claim 1 or a stereoisomer or pharmaceutically acceptable salt thereof, wherein
$R^2$ is Cl, Br, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl and ring are optionally substituted, independently, with 1-3 substituents of $R^9$;
each of $R^1$, $R^4$, $R^5$ and $R^8$, independently, is H, F, methyl, CN or OH;
each of $R^3$ and $R^6$, independently, is H, F, Cl, $CF_3$, methyl, CN, OH, $OCH_3$, or $NHCH_3$;
$R^7$ is a ring selected from phenyl, pyridyl, pyrimidyl, pyridazinyl, pyrazinyl, or thienyl, said ring optionally substituted, independently, with 1-3 substituents of $R^9$; and
—X—Y— is —$CH_2$—O— or —O—$CH_2$—.

9. The compound of claim 1 or a stereoisomer or pharmaceutically acceptable salt thereof, wherein
$A^3$ is N;
$A^4$ is $CR^4$;
$R^2$ is Cl, Br, —$OC_{1-6}$alkyl, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the —$OC_{1-6}$alkyl, $C_{1-6}$-alkyl, $C_{2-4}$alkenyl, $C_{2-4}$alkynyl and ring are optionally substituted, independently, with 1-3 substituents of $R^9$;
each of $R^1$, $R^4$, $R^5$ and $R^8$, independently, is H, F, methyl, CN or OH;
$R^6$ is H, F, Cl, $CF_3$, methyl, CN, OH, $OCH_3$, or $NHCH_3$;
$R^7$ is a ring selected from phenyl, pyridyl, pyrimidyl, pyridazinyl, or pyrazinyl, said ring optionally substituted, independently, with 1-3 substituents of $R^9$; and
—X—Y— is —$CH_2$—O— or —O—$CH_2$—.

10. The compound of claim 4, or a stereoisomer or pharmaceutically acceptable salt thereof, wherein
$A^3$ is $CR^3$;
$A^4$ is $CR^4$ or N;
$R^2$ is Cl, Br, —$OC_{1-6}$alkyl, $C_{1-6}$-alkyl, $C_{2-4}$alkenyl, $C_{2-4}$alkynyl, or a ring selected from phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the —$OC_{1-6}$alkyl, $C_{1-6}$-alkyl, $C_{2-4}$alkenyl, $C_{2-4}$alkynyl and ring are optionally substituted, independently, with 1-3 substituents of $R^9$;
each of $R^1$, $R^4$, $R^5$ and $R^8$, independently, is H, F, methyl, CN or OH;
each of $R^3$ and $R^6$, independently, is H, F, Cl, $CF_3$, methyl, CN, OH, $OCH_3$, or $NHCH_3$;
$R^7$ is a ring selected from phenyl, pyridyl, pyrimidyl, pyridazinyl, or pyrazinyl said ring optionally substituted, independently, with 1-3 substituents of $R^9$; and
—X—Y— is —$CH_2$—O— or —O—$CH_2$—.

11. A compound or a stereoisomer or pharmaceutically acceptable salt thereof, wherein the compound is selected from (5R/S)-7-(2-fluoro-3-pyridinyl)-3-(2-fluoro-4-pyridinyl)-6',7'-dihydrospiro[chromeno[2,3-c]pyridine-5,3'-[1,4]oxazepin]-5'-amine;

(5R)-7-(2-fluoro-3-pyridinyl)-3-(2-fluoro-4-pyridinyl)-6',7'-dihydrospiro[chromeno[2,3-c]pyridine-5,3'-[1,4]oxazepin]-5'-amine;

(5S)-7-(2-fluoro-3-pyridinyl)-3-(2-fluoro-4-pyridinyl)-6',7'-dihydrospiro[chromeno[2,3-c]pyridine-5,3'-[1,4]oxazepin]-5'-amine;

(5S)-7-bromo-3-chloro-6',7'-dihydrospiro[chromeno[2,3-c]pyridine-5,3'-[1,4]oxazepin]-5'-amine;

(5R)-7-bromo-3-chloro-6',7'-dihydrospiro[chromeno[2,3-c]pyridine-5,3'-[1,4]oxazepin]-5'-amine;

(3R/S)-2'-(2,2-dimethylpropoxy)-4'-fluoro-7'-(2-fluoro-3-pyridinyl)-6,7-dihydrospiro[1,4-oxazepine-3,9'-xanthen]-5-amine;

(3S)-2'-(2,2-dimethylpropoxy)-4'-fluoro-7'-(2-fluoro-3-pyridinyl)-6,7-dihydrospiro[1,4-oxazepine-3,9'-xanthen]-5-amine;

(3R)-2'-(2,2-dimethylpropoxy)-4'-fluoro-7'-(2-fluoro-3-pyridinyl)-6,7-dihydrospiro[1,4-oxazepine-3,9'-xanthen]-5-amine; or (5R)-7-(2-fluoro-3-pyridinyl)-3-(2-fluoro-4-pyridinyl)-6',7'-dihydro-2'H-spiro[chromeno[2,3-c]pyridine-5,5'-[1,4]oxazepin]-3'-amine.

12. A pharmaceutical composition comprising a compound according to claim 1 and a pharmaceutically acceptable excipient.

13. A method of treating Alzheimer's disease, cognitive impairment or a combination thereof in a subject, the method comprising administering to the subject an effective dosage amount of a compound of claim 1.

14. A process for preparing a compound of claim 1, the process comprising the step of reacting a compound 20

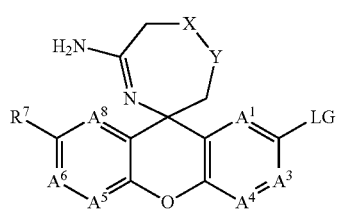

wherein $A^1$, $A^3$, $A^4$, $A^5$, $A^6$, $A^8$, $R^7$, X and Y of compound 20 are as defined in claim 1 and leaving group (LG) is Cl or Br, with a compound having the structure

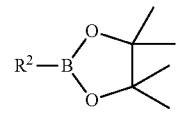

or $R^7$—$B(OH)_2$, wherein $R^2$ is as defined in claim 1 to prepare the compound of claim 1.

* * * * *